(12) United States Patent
Masubuchi et al.

(10) Patent No.: US 8,663,897 B2
(45) Date of Patent: *Mar. 4, 2014

(54) FLUORINE-CONTAINING SULFONATES HAVING POLYMERIZABLE ANIONS AND MANUFACTURING METHOD THEREFOR, FLUORINE-CONTAINING RESINS, RESIST COMPOSITIONS, AND PATTERN-FORMING METHOD USING SAME

(75) Inventors: Takashi Masubuchi, Fujimino (JP); Kazunori Mori, Iruma-gun (JP); Yuji Hagiwara, Kawagoe (JP); Satoru Narizuka, Saitama (JP); Kazuhiko Maeda, Tokyo (JP)

(73) Assignee: Central Glass Company, Limited, Ube-shi (JP)

( * ) Notice: Subject to any disclaimer, the term of this patent is extended or adjusted under 35 U.S.C. 154(b) by 166 days.

This patent is subject to a terminal disclaimer.

(21) Appl. No.: 13/121,315

(22) PCT Filed: Oct. 8, 2009

(86) PCT No.: PCT/JP2009/067567
§ 371 (c)(1),
(2), (4) Date: Mar. 28, 2011

(87) PCT Pub. No.: WO2010/044372
PCT Pub. Date: Apr. 22, 2010

(65) Prior Publication Data
US 2011/0177453 A1    Jul. 21, 2011

(30) Foreign Application Priority Data
Oct. 17, 2008    (JP) ................. 2008-268476

(51) Int. Cl.
| G03F 7/004 | (2006.01) |
| G03F 7/30 | (2006.01) |
| C07C 303/32 | (2006.01) |
| C07C 309/20 | (2006.01) |
| C08F 220/24 | (2006.01) |
| G03F 7/039 | (2006.01) |

(52) U.S. Cl.
CPC .............. G03F 7/0397 (2013.01); G03F 7/30 (2013.01); C07C 303/32 (2013.01); C07C 309/20 (2013.01); C08F 220/24 (2013.01); Y10S 430/108 (2013.01); Y10S 430/111 (2013.01)
USPC ........ 430/270.1; 430/330; 430/907; 430/910; 526/243; 526/321; 526/325; 526/100; 526/102; 526/109; 526/110; 526/113

(58) Field of Classification Search
CPC ........ G03F 7/0397; G03F 7/30; C07C 303/32; C07C 309/20; C08F 220/24
USPC ............ 430/270.1, 326, 330, 905, 910; 562/100, 102, 109, 110, 113; 526/243, 526/321, 325
See application file for complete search history.

(56) References Cited

U.S. PATENT DOCUMENTS

| 5,945,250 | A | 8/1999 | Aoai et al. | |
| 7,871,752 | B2 | 1/2011 | Hasegawa et al. | |
| 8,057,985 | B2 * | 11/2011 | Ohashi et al. | 430/270.1 |
| 8,105,748 | B2 | 1/2012 | Ohashi et al. | |
| 8,222,448 | B2 * | 7/2012 | Jodry et al. | 560/150 |
| 2008/0026331 | A1 | 1/2008 | Hasegawa et al. | |
| 2008/0071113 | A1 | 3/2008 | Matsunaga et al. | |
| 2008/0102407 | A1 | 5/2008 | Ohsawa et al. | |
| 2009/0069521 | A1 | 3/2009 | Nagai et al. | |
| 2010/0055608 | A1 * | 3/2010 | Ohashi et al. | 430/270.1 |

(Continued)

FOREIGN PATENT DOCUMENTS

| CA | 2049772 A1 | 2/1992 |
| JP | 4-230645 A | 8/1992 |

(Continued)

OTHER PUBLICATIONS

International Search Report with English language translation dated Jan. 13, 2010 (four (4) pages).

(Continued)

Primary Examiner — John Chu
(74) Attorney, Agent, or Firm — Crowell & Moring LLP

(57) ABSTRACT

According to the present invention, there is provided a polymerizable fluorine-containing sulfonic acid onium salt of the following general formula (2) and a resin obtained by polymerization thereof. It is possible by the use of this sulfonate resin of the present invention to provide a resist composition with high resolution, board depth of focus tolerance (DOF), small line edge roughness (LER) and high sensitivity.

[Chem. 120]

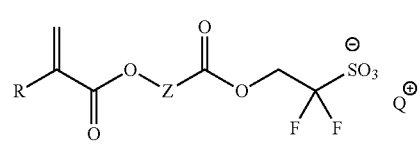

(2)

In the formula, Z represents a substituted or unsubstituted $C_1$-$C_6$ straight or branched alkylene group, or a divalent moiety in which substituted or unsubstituted $C_1$-$C_6$ straight or branched alkylene groups are bonded in series to a divalent group obtained by elimination of two hydrogen atoms from an alicyclic or aromatic hydrocarbon; R represents a hydrogen atom, a halogen atom, or a $C_1$-$C_3$ alkyl or fluorine-containing alkyl group; and $Q^+$ represents a sulfonium cation or an iodonium cation.

24 Claims, No Drawings

(56) References Cited

U.S. PATENT DOCUMENTS

| | | | |
|---|---|---|---|
| 2010/0063232 A1 | 3/2010 | Nagai et al. | |
| 2010/0099042 A1 | 4/2010 | Ohashi et al. | |
| 2011/0015431 A1* | 1/2011 | Jodry et al. | 560/232 |

FOREIGN PATENT DOCUMENTS

| | | |
|---|---|---|
| JP | 2002-214774 A | 7/2002 |
| JP | 2004-4561 A | 1/2004 |
| JP | 2004-117959 A | 4/2004 |
| JP | 3613491 B2 | 11/2004 |
| JP | 2005-84365 A | 3/2005 |
| JP | 2006-178317 A | 7/2006 |
| JP | 2007-197718 A | 8/2007 |
| JP | 2008-133448 A | 6/2008 |
| JP | 2009-275155 A | 11/2009 |
| TW | 200815484 A | 4/2008 |
| TW | 201022199 A | 6/2010 |
| WO | WO 96/41842 A1 | 12/1996 |
| WO | WO 2006/121096 A1 | 11/2006 |
| WO | WO 2008/056795 A1 | 5/2008 |
| WO | WO 2009/038148 A1 | 3/2009 |

OTHER PUBLICATIONS

Form PCT/ISA/237 dated Jan. 13, 2010 (four (4) pages).
Taiwanese Office Action (six (6) pages).

* cited by examiner

FLUORINE-CONTAINING SULFONATES HAVING POLYMERIZABLE ANIONS AND MANUFACTURING METHOD THEREFOR, FLUORINE-CONTAINING RESINS, RESIST COMPOSITIONS, AND PATTERN-FORMING METHOD USING SAME

TECHNICAL FIELD

The present invention relates to novel fluorine-containing sulfonates having polymerizable anions, a manufacturing method therefor, fluorine-containing resins, resist compositions and a pattern-forming method using the same. More specifically, the present invention relates to a resist composition suitable as a chemically amplified resist material, which is useful for fine processing using high energy radiation, such as near-ultraviolet radiation, far-ultraviolet radiation, extreme ultraviolet (EUV) radiation, soft X-ray, X-ray or γ-ray produced by an excimer laser e.g. KrF excimer laser, ArF excimer laser or $F_2$ excimer laser or synchrotron radiation, or charged particle beam e.g. electron beam, a novel fluorine-containing resin for use in the resist composition, a novel fluorine-containing sulfonate for synthesis of the fluorine-containing resin and a manufacturing method therefor.

BACKGROUND ART

In recent years, there has been a rapid advance toward finer pattern rules for high integration and high speed performance of LSI devices. The application of shorter-wavelength exposure light sources is seen as one factor behind the advance to the finer pattern rules. For example, the wavelength reduction from mercury-lamp i line (365 nm) to KrF excimer laser radiation (248 nm) enables mass production of 64-Mbit DRAM (Dynamic Random Access Memory) (with a processing size of 0.25 μm or smaller). Further, the application of lithography process using ArF excimer laser radiation (193 nm) has been thoroughly studied for production of DRAM with an integration of 256M and of 1G or higher. In particular, the combination of ArF lithography process with a high NA lens (NA≥0.9) is being studied for production of 65-nm node devices. For production of next-generation 45-nm node devices, ArF immersion lithography process is being developed and put into use. Furthermore, double-exposure/double-patterning process based on ArF lithography and extreme ultraviolet (EUV) lithography process appear promising for 45-nm or smaller design rules.

As resist materials suitable for exposure to such short-wavelength radiation, attention is given to "chemically amplified resist compositions". The chemically amplified resist composition is a pattern forming material that contains an acid generator (hereinafter referred to as a "photoacid generator") capable of generating an acid by irradiation with high energy radiation (hereinafter referred to as "exposure") and forms a resist pattern according to a photomask shape by causing a change in the developer solubility of exposed portions of the resist film through a reaction using the acid generated by exposure as a catalyst and thereby dissolving the exposed portions of the resist film.

It is required that the photoacid generator of the chemically amplified resist material has the characteristics that: the photoacid generator shows a high transparency to high energy radiation and a high acid generation quantum yield; and the generated acid shows a sufficiently high acidity, a sufficiently high boiling point and an adequate diffusion distance (referred to as "diffusion length") in the resist film.

In the case of an ionic photoacid generator, the structure of the anionic moiety of the photoacid generator is an important factor for the acidity, boiling point and diffusion length of the generated acid. In the case of an ordinary, sulfonyl- or sulfonate-containing nonionic photoacid generator, the structure of the sulfonyl moiety of the photoacid generator is an important factor for the acidity, boiling point and diffusion length of the generated acid. For example, a photoacid generator having a trifluoromethanesulfonyl structure is capable of generating an acid of sufficiently high acidity so that the photoresist has sufficiently high resolution, but is disadvantageous in that the photoresist has high photomask dependence due to the low boiling point and long diffusion length of the generated acid. A photoacid generator having a sulfonyl structure with a large organic group bonded thereto, such as 10-camphorsulfonyl structure, is capable of generating an acid of sufficiently high boiling point and adequately short diffusion length so that the photoresist has low photomask dependence, but is disadvantageous in that the photoresist does not has sufficient resolution due to the insufficient acidity of the generated acid.

For these reasons, the chemically amplified resist composition for exposure to ArF eximer laser radiation generally uses a photoacid generator that generates a perfluoroalkanesulfonic acid of high acidity. However, the stability (non-degradability) of the perfluorooctanesulfonic acid and its derivatives due to C—F bonds as well as the biological concentration and accumulation of the perfluorooctanesulfonic acid and its derivatives due to hydrophobic and lipophilic natures have become problems. The above-mentioned problems are being raised against perfluoroalkanesulfonic acids of 5 or more carbon atoms. The U.S. Environmental Protection Agency has thus proposed a rule to regulate the use of these compounds.

Under the above circumstances, alkoxycarbonylfluoroalkanesulfonic acid onium salts such triphenylsulfonium methoxycarbonyldifluoromethanesulfonate (Patent Document 1), (4-methylphenyl)diphenylsulfonyl t-butoxycarbonyldifluoromethanesulfonate (Patent Document 2) and triphenylsulfonium (adamantane-1-ylmethyl)oxycarbonyldifluoromethanesulfonate (Patent Document 3) have been developed as acid generators that generate a partially- or fully-fluorinated, lower-carbon-number alkanesulfonic acid of sufficient acidity, adequate boiling point diffusion length and less environmental load.

In response to the demand for higher integration, there arises a need for not only the photoacid generator but also the photosensitive resin composition as the resist composition to address the requirement for higher resolution. The requirements for broader depth of focus tolerance (DOF) and smaller pattern line edge roughness (LER) are also increasing as finer patterning techniques progress. It is thus an urgent task to develop a resist composition that satisfies the requirements of high resolution, broad DOF, small LER, high sensitivity, good substrate adhesion and high etching resistance with the progress of the finer patterning techniques in the semiconductor industry.

In view of the foregoing, there have been reported a resin containing acroyloxyphenyldiphenylsulfonate as a copolymerization component for sensitivity improvement (Patent Document 4) and a base resin in which the above monomer is incorporated as a copolymerization component for LER improvement in polyhydroxystyrene (Patent Document 5). Each of these resins cannot however satisfy the above requirements as the cationic moiety is bonded to the base resin so that the sulfonic acid generated by irradiation with high energy radiation is the same as those generated from conventional photoacid generators. There has also been reported a sulfonate having an anionic moiety such as polystyrenesulfonic acid incorporated in its polymer chain for sensitivity and LER improvements (Patent Document 6). This sulfonate generates an arenesulfonic acid or alkylsulfonic acid derivative that is low in acidity and thus not enough to cleave an acid labile group, notably an acid labile group of a chemically amplified photoresist for use with ArF laser radiation.

Further, liquid immersion exposure is known in which each of a photoresist film applied to and formed on a resist wafer and a lens of a projection exposure system comes into contact with a liquid immersion medium such as water. In this exposure process, the pattern resolution of the photoresist film may be lowered by immersion of the liquid immersion medium into the photoresist film. There is also a problem that the surface of the lens may become dirty by elution of the photoresist component into the liquid immersion medium.

Fine processing using high energy radiation, such as extreme ultraviolet (EUV) radiation or charged particle radiation e.g. electron beam radiation, appears promising as the exposure process later than ArF lithography. In this fine processing process, exposure has to be carried out under vacuum (under reduced pressure) and thus causes volatilization of the sulfonic acid generated from the photoacid generator so that the resist pattern may not be formed with a good pattern shape and that the exposure system may be damaged by the volatilized sulfonic acid.

In order to solve the above problems, there have been developed sulfonates each having an anionic moiety incorporated in its polymer side and capable of generating a partially- or fully-fluorinated, lower-carbon-number alkanesulfonic acid (see Patent Documents 7 to 10). However, these sulfonates are produced from expensive raw materials by complicated production procedures and thus still have some problems left for industrial use.

Prior Art Documents
Patent Documents

Patent Document 1: Japanese Laid-Open Patent Publication No. 2004-117959

Patent Document 2: Japanese Laid-Open Patent Publication No. 2002-214774

Patent Document 3: Japanese Laid-Open Patent Publication No. 2004-004561

Patent Document 4: Japanese Laid-Open Patent Publication No. 4-230645

Patent Document 5: Japanese Laid-Open Patent Publication No. 2005-084365

Patent Document 6: Japanese Patent No. 3613491

Patent Document 7: International Publication No. WO 2006/121090 (PCT/JP/2006/309446).

Patent Document 8: Japanese Laid-Open Patent Publication No. 2006-178317

Patent Document 9: Japanese Laid-Open Patent Publication No. 2007-197718

Patent Document 10: Japanese Laid-Open Patent Publication No. 133448

SUMMARY OF THE INVENTION

Problems to be Solved by the Invention

It is accordingly an object of the present invention to provide a photoacid generator for preparation of a positive or negative photoresist composition that is capable of forming a comprehensively good pattern shape because of the characteristics of high resolution, broad depth of focus tolerance (DOF), small line edge roughness (LER) and high sensitivity. It is also an object of the present invention to provide a specific monomer suitable for synthesis of such a photoacid generator, a production method therefor, and a pattern forming method suitable for use with the resist composition.

Means for Solving the Problems

As a result of extensive researches made to achieve the above objects, the present inventors have found that a positive or negative resist composition of high resolution, broad depth of focus tolerance (DOF), small line edge roughness (LER) and high sensitivity can be prepared from either a resin having an acid labile group to function as a positive resist resin or a resin having a cross-linking site to function as a negative resist resin (hereinafter also referred to as a "base resin"), a photoacid generator and a solvent (and additionally a cross-linking agent in the case of the negative resist type) by the use of a resin having a specific fluorine-containing sulfonate structure in its side chain as the photo acid generator. A polymeric photoacid generator, in which a moiety having the function of a chemically amplified photoacid generator is fixed to the polymer side chain so that the diffusion length of the resulting photoacid would be substantially limited, is expected to show broad DOF and small LER. However, these advantages of the polymeric photoacid generator have not yet been sufficiently exerted. The present inventors have found that it is possible to adjust the ease of diffusion of the generated photoacid and the diffusion length of the generated photoacid by controlling the chemical structure of the linking group between the main chain and the acid moiety of the polymeric photoacid generator and the length of the side chain of the polymeric photoacid generator. The present inventors have also found a monomer suitable for synthesis of the resin having such a specific fluorine-containing sulfonate structure and a production method therefor. The present invention is based on these findings.

Namely, the present invention has the following features.

[1] A polymerizable fluorine-containing sulfonic acid or sulfonate having a structure of the following general formula (1):

[Chem. 1]

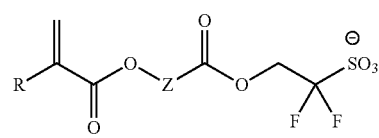

(1)

where Z represents a substituted or unsubstituted $C_1$-$C_6$ straight or branched alkylene group, or a divalent moiety in which substituted or unsubstituted $C_1$-$C_6$ straight or branched alkylene groups are bonded in series to a divalent group obtained by elimination of two hydrogen atoms from an alicyclic or aromatic hydrocarbon; and R represents a hydrogen atom, a halogen atom, or a $C_1$-$C_3$ alkyl or fluorine-containing alkyl group.

[2] A polymerizable fluorine-containing sulfonic acid onium salt of the following general formula (2):

[Chem. 2]

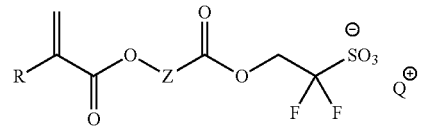

(2)

where Z and R have the same definitions as in the general formula [1]; and Q⁺ represents a sulfonium cation of the following general formula (a) or the following general formula (b), or an iodonium cation of the following general formula (c),

[Chem. 3]

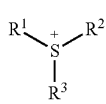
(a)

where $R^1$, $R^2$ and $R^3$ each independently represents a substituted or unsubstituted $C_1$-$C_{20}$ straight, branched or cyclic alkyl, alkenyl or oxoalkyl group, or a substituted or unsubstituted $C_6$-$C_{18}$ aryl, aralkyl or aryloxoalkyl group; and two or more of $R^1$, $R^2$ and $R^3$ may be bonded to each other to form a ring with a sulfur atom in the formula,

[Chem. 4]

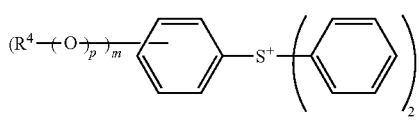
(b)

where $R^4$—$(O)_p$— are independent of each other; $R^4$ represents a substituted or unsubstituted $C_1$-$C_{20}$ straight, branched or cyclic alkyl or alkenyl group, or a substituted or unsubstituted $C_6$-$C_{14}$ aryl group; m represents an integer of 1 to 5; p represents 0 or 1; and $R^4$ may contain a carbonyl group, a hydroxyl group, an ester bond, a lactone ring, an amino group, an amide group or an ether bond as a substituent group,

[Chem. 5]

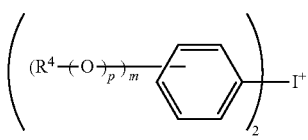
(c)

where $R^4$—$(O)_p$— are independent of each other; $R^4$ represents a substituted or unsubstituted $C_1$-$C_{20}$ straight, branched or cyclic alkyl or alkenyl group, or a substituted or unsubstituted $C_6$-$C_{14}$ aryl group; m represents an integer of 1 to 5; p represents 0 or 1; and $R^4$ may contain a carbonyl group, a hydroxyl group, an ester bond, a lactone ring, an amino group, an amide group or an ether bond as a substituent group.

[3] A polymerizable fluorine-containing sulfonate compound of the following general formula (3):

[Chem. 6]

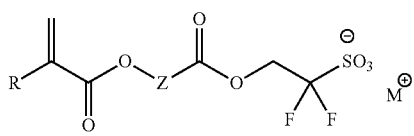
(3)

where Z and R have the same definitions as in the general formula (1); and M⁺ represents one of a lithium ion, a sodium ion, a potassium ion and ammonium ions.

[4] A resin having a repeating unit of the following general formula (4):

[Chem. 7]

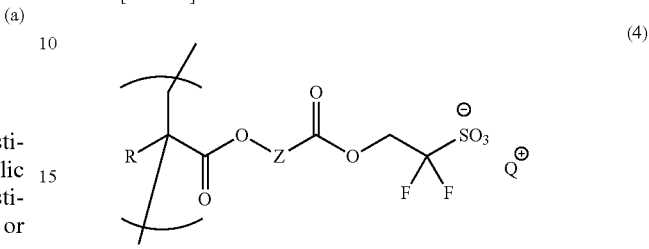
(4)

where Z and R have the same definitions as in the general formula (1); and Q⁺ has the same definition as in the general formula (2).

[5] A resin having a repeating unit of the following general formula (5):

[Chem. 8]

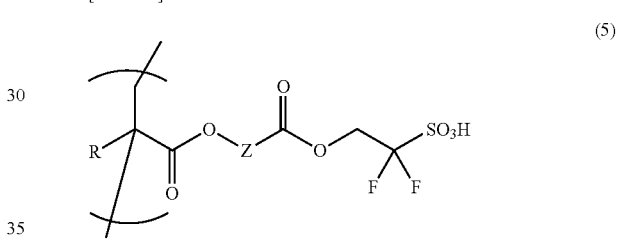
(5)

where Z and R have the same definitions as in the general formula (1).

[6] The resin according to Inventive Feature [4] or [5], further having at least one selected from the group consisting of repeating units formed by cleavage of polymerizable double bonds of olefins, fluorine-containing olefins, acrylic esters, methacrylic esters, fluorine-containing acrylic esters, fluorine-containing methacrylic esters, norbornene compounds, fluorine-containing norbornene compounds, styrenic compounds, fluorine-containing styrenic compounds, vinyl ethers and fluorine-containing vinyl ethers.

[7] The resin according to Inventive Feature [4] or [5], further having a repeating unit of the following general formula (6):

[Chem. 9]

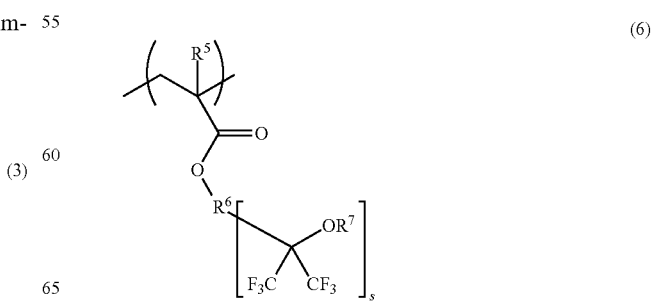
(6)

where $R^5$ represents a hydrogen atom, a halogen atom, or a $C_1$-$C_3$ alkyl or fluorine-containing alkyl group; $R^6$ represents a substituted or unsubstituted, straight, branched or cyclic structure-containing alkylene group, a substituted or unsubstituted divalent aromatic group, or a divalent organic moiety in which a plurality of substituted or unsubstituted, straight, branched or cyclic structure-containing alkylene and/or substituted or unsubstituted divalent aromatic groups are bonded to each other, and may be partially fluorinated; $R^7$ represents a hydrogen atom, a substituted or unsubstituted $C_1$-$C_{25}$ straight, branched or cyclic aliphatic hydrocarbon group, or a substituted or unsubstituted $C_1$-$C_{25}$ aromatic hydrocarbon group, a part of which may contain a fluorine atom, an ether bond or a carbonyl group; and s represents an integer of 1 or 2.

[8] The resin according to Inventive Feature [4] or [5], further having a repeating unit of the following general formula (7):

[Chem. 10]

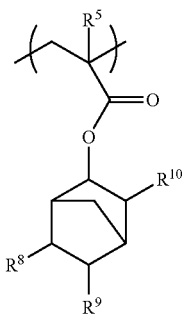

(7)

where $R^5$ represents a hydrogen atom, a halogen atom, or a $C_1$-$C_3$ alkyl or fluorine-containing alkyl group; either one of $R^8$, $R^9$ and $R^{10}$ represents a $CF_3C(CF_3)(OH)CH_2$— group; and the other two of $R^8$, $R^9$ and $R^{10}$ each represent a hydrogen atom.

[9] The resin according to Inventive Feature [4] or [5], further having a repeating unit of the following general formula (8):

[Chem. 11]

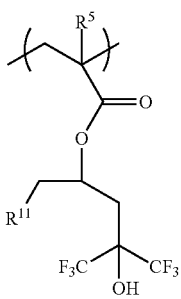

(8)

where $R^5$ represents a hydrogen atom, a halogen atom, or a $C_1$-$C_3$ alkyl or fluorine-containing alkyl group; and $R^{11}$ represents a $C_1$-$C_4$ alkyl or fluorine-containing alkyl group.

[10] The resin according to Inventive Feature [4] or [5], further having a repeating unit of the following general formula (9):

[Chem. 12]

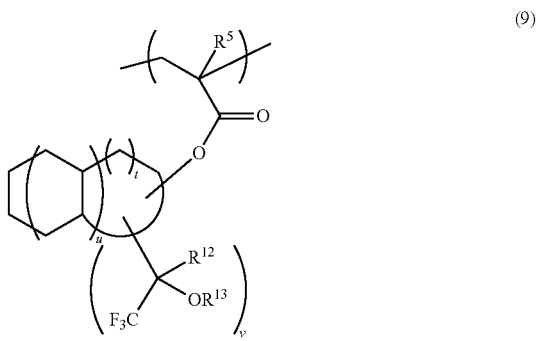

(9)

where $R^5$ represents a hydrogen atom, a halogen atom, or a $C_1$-$C_3$ alkyl or fluorine-containing alkyl group; $R^{12}$ represents a methyl group or a trifluoromethyl group; $R^{13}$ represents a hydrogen atom, a substituted or unsubstituted $C_1$-$C_{25}$ straight, branched or cyclic aliphatic hydrocarbon group, or a substituted or unsubstituted $C_1$-$C_{25}$ aromatic hydrocarbon group, a part of which may contain a fluorine atom, an ether bond or a carbonyl group; u represents an integer of 0 to 2; t and v each independently represent an integer of 1 to 8 and satisfy a relationship of $v \leq t+2$; and, when v is 2 to 8, $R^{12}$ and $R^{13}$ may be the same or different.

[11] The resin according to Inventive Feature [4] or [5], further having a repeating unit of the following general formula (10):

[Chem. 13]

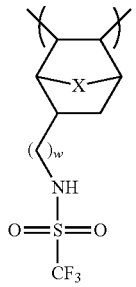

(10)

where X represents either of —$CH_2$—, —O— and —S—; and w represents an integer of 2 to 6.

[12] The resin according to Inventive Feature [4] or [5], further having a repeating unit of the following general formula (11):

[Chem. 14]

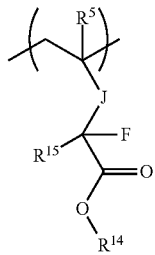

(11)

where $R^5$ represents a hydrogen atom, a halogen atom, or a $C_1$-$C_3$ alkyl or fluorine-containing alkyl group; $R^{15}$ represents a fluorine atom, or a fluorine-containing alkyl group; J represents a divalent linking group; and $R^{14}$ represents a hydrogen atom, a substituted or unsubstituted $C_1$-$C_{25}$ straight, branched or cyclic aliphatic hydrocarbon group, or a substituted or unsubstituted $C_1$-$C_{25}$ aromatic hydrocarbon group, a part of which may contain a fluorine atom, an ether bond or a carbonyl group.

[13] A resist material, comprising at least the resin according to any one of Inventive Features [4] to [12] and a solvent.

[14] The resist material according to Inventive Feature [13], wherein the resin has an acid labile group so that the resist material functions as a chemically amplified positive resist material.

[15] The resist material according to Inventive Feature [13] or [14], wherein the resist material further comprises a resin having an acid labile group and functions as a chemically amplified positive resist material.

[16] The resist material according to Inventive Feature [13], wherein the resin has an alcoholic hydroxyl group or a carboxyl group so that the resist material functions as a chemically amplified negative resist material.

[17] The resist material according to Inventive Feature [13] or [16], wherein the resist material further comprises a resin having an alcoholic hydroxyl group or a carboxyl group and functions as a chemically amplified negative resist material.

[18] A pattern forming method, comprising: applying the resist material according to any one of Inventive Features [13] to [17] to a substrate; after heat treating the applied resist material, exposing the applied resist material to high energy radiation of 300 nm or less wavelength through a photomask; and, after heat treating the exposed resist material as needed, developing the exposed resist material with a developer.

[19] The pattern formation method according to Inventive Feature [18], wherein the exposing is performed by immersion lithography using ArF excimer laser radiation of 193 nm wavelength and allowing insertion of water or any other liquid of higher refractive index than that of the air between the substrate to which the resist material is applied and projector lens.

[20] A compound of the following formula (12):

[Chem. 15]

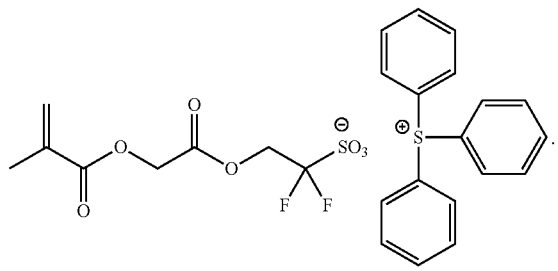

(12)

[21] A compound of the following formula (13):

[Chem. 16]

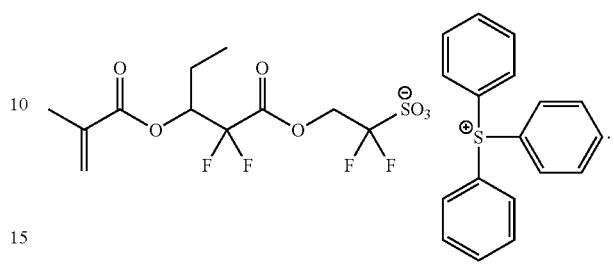

(13)

[22] A compound of the following formula (14):

[Chem. 17]

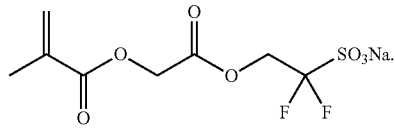

(14)

[23] A compound of the following formula (15):

[Chem. 18]

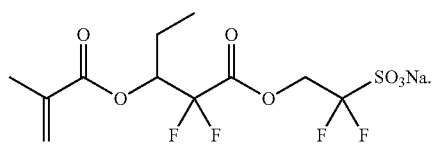

(15)

[24] A method for producing the polymerizable fluorine-containing sulfonate of the above general formula (3), comprising performing esterification of a carboxylic acid derivative of the following general formula (16) and a 1,1-difluoro-2-hydroxyethanesulfonate of the following general formula (17):

[Chem. 19]

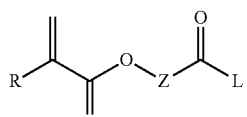

(16)

[Chem. 20]

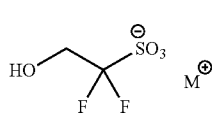

(17)

where Z and R have the same definitions as in the general formula (1); L represents a hydroxyl group or a halogen atom; and $M^+$ has the same definition as in the general formula (3).

[25] A method for producing the polymerizable fluorine-containing sulfonic acid onium salt of the above general formula (2), comprising performing onium salt exchange reaction of the polymerizable fluorine-containing sulfonate of the above general formula (3) with a monovalent onium salt of the following general formula (18):

[Chem. 21]

$$Q^+Y^- \quad (18)$$

where $Y^-$ represents a monovalent anion; and $Q^+$ has the same definition as in the general formula (2).

In particular, it is possible that the resist composition prepared using the resin having the repeating unit of the general formula (4) according to the present invention, which can be obtained by homopolymerization or copolymerization of the polymerizable fluorine-containing sulfonic acid onium salt of the general formula (2) shows high sensitivity to high energy radiation as the sulfonic acid salt functioning as a photoacid generator has two α-position fluorine atoms and generates a very strong sulfonic acid so as to efficiently cleave an acid lable group of the base resin in the case of the positive resist composition or efficiently form a cross-linking moiety in the base resin in the case of the negative resist type. It is further possible by the introduction of the acid labile group or cross-linking moiety into the resin having the repeating unit of the general formula (4) according to the present invention that the resist material prepared using such a resin eliminates the need to use any additional base resin, controls the ease of diffusion and diffusion length of the photoacid, shows broad DOF and small LER and enables pattern forming with good shape stability. The polymerizable fluorine-containing sulfonic acid onium salt of the general formula (2) can be easily obtained by esterification of the carboxylic acid derivative of the general formula (16) and the 1,1-difluoro-2-hydroxyethane-sulfonate of the general formula (17) and then by onium salt exchange reaction the resulting polymerizable fluorine-containing sulfonate compound of the general formula (3) with the monovalent onium salt of the general formula (18). The sulfonate resin having the repeating unit of the general formula (4) according to the present invention can be produced efficiently from the polymerizable fluorine-containing sulfonic acid onium salt of the general formula (2).

BEST MODES FOR CARRYING OUT THE INVENTION

Hereinafter, preferred embodiments of the present invention will be described below in detail. It is however to be understood that: the following embodiments are illustrative and are not intended to limit the present invention thereto; and various changes and modifications can be made on the following embodiments, without departing from the scope of the present invention, based on the ordinary knowledge of one skilled in the art.

A material relationship of the present invention is indicated in SCHEME (1).

SCHEME (1)

[Chem. 22]

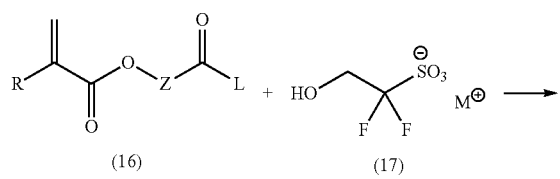

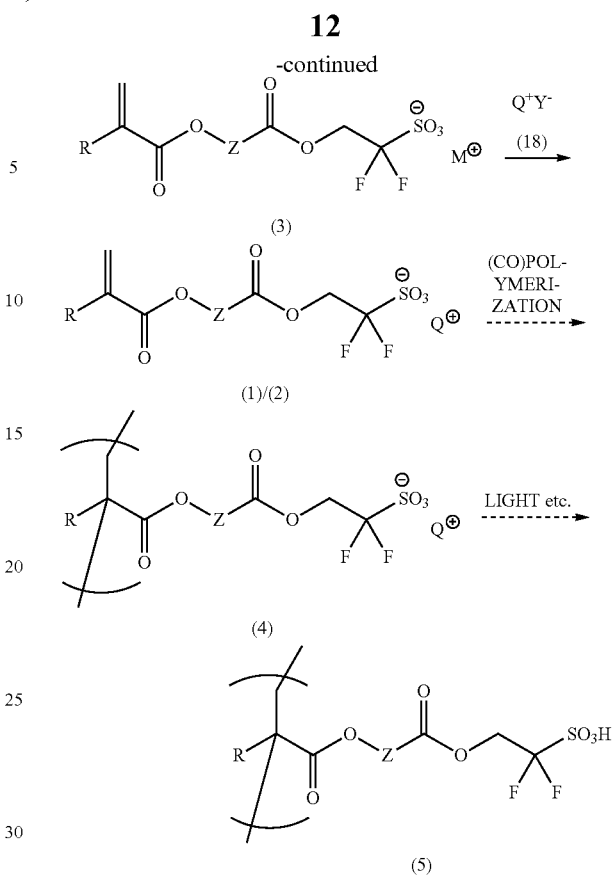

[Polymerizable Fluorine-Containing Sulfonic Acid and Sulfonate]

A polymerizable fluorine-containing sulfonic acid or sulfonate having a structure of the general formula (1) according to the present invention can be formed by esterification of a carboxylic acid derivative of the general formula (16) and a 1,1-difluoro-2-hydroxyethanesulfonate of the general formula (17) as shown in SCHEME (1).

[Chem. 23]

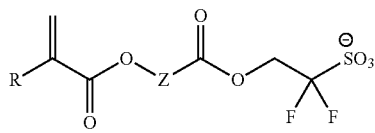

In the general formula (1), R represents a hydrogen atom, a halogen atom, or a $C_1$-$C_3$ alkyl or fluorine-containing alkyl group.

Examples of the halogen atom are fluorine, chlorine, bromine and iodine. Examples of the $C_1$-$C_3$ alkyl group are methyl, ethyl, n-propyl and i-propyl. Examples of the $C_1$-$C_3$ fluorine-containing alkyl group are fluoromethyl, difluoromethyl, trifluoromethyl, 2-fluoroethyl, 2,2-difluoroethyl, 2,2,2-trifluoroethyl, pentafluoroethyl, 1-methyl-2,2,2-trifluoroethyl, 1-(trifluoromethyl)-2,2,2-trifluoroethyl and 1-(trifluoromethyl)-1,2,2,2-tetrafluoroethyl. Among others, hydrogen, fluorine, methyl group and trifluoromethyl are preferred as R.

In the general formula (1), Z represents a substituted or unsubstituted $C_1$-$C_6$ straight or branched alkylene group, or a divalent moiety in which substituted or unsubstituted C₁-C₆ straight or branched alkylene groups are bonded in series to a divalent group obtained by elimination of two hydrogen atoms from an alicyclic or aromatic hydrocarbon. Examples of the unsubstituted $C_1$-$C_6$ straight or branched alkylene group are methylene, ethylene, 1,2- or 1,3-propylene, 1,2-, 1,3- or 1,4-butylene, pentamethylene, 2,2-dimethyl-1,3-propylene and hexamethylene.

As a substituent group of the alkylene group, there can be used: halogen atoms such as fluorine, chlorine, bromine and iodine; hydroxyl group; thiol group; aryl groups; and organic groups containing hetero atoms such as halogen, oxygen, nitrogen, sulfur, phosphorus and silicon. The can also be used a keto group in which two hydrogen atoms on the same carbon atom of the alkylene group are replaced with one oxygen atom. These substituent groups can be present in any number as long as it is structurally possible.

Examples of the $C_1$-$C_6$ straight or branched alkylene group substituted with the above substituent group are phenylmethylene, methoxymethylene, methylthiomethylene, ethoxymethylene, phenoxymethylene, methoxycarbonylmethylene, ethoxycarbonylmethylene, acetylmethylene, fluoromethylene, difluoromethylene, chloromethylene, dichloromethylene, trifluoroacetylmethylene, trichloroacetylmethylene, pentafluorobenzoylmethylene, aminomethylene, cyclohexylaminomethylene, diphenylphosphinomethylene, trimethylsilylmethylene, hydroxymethylene, hydroxyethylene and hydroxycarbonylmethylene.

The divalent moiety in which the alkylene groups are bonded in series to the divalent group obtained by elimination of two hydrogen atoms from the alicyclic or aromatic hydrocarbon is represented by —$(CR^{21}R^{22})_n$—B—$(CR^{21}R^{22})_l$— where B is a cyclic group selected from divalent alicyclic and aromatic hydrocarbon groups; l and n each independently represents an integer of 0 to 10, preferably 0 or 1. It is more preferable that either one of l and n is 0. The definition of the after-mentioned linking group W is applicable to $R^{21}$, $R^{22}$, l and n. Any of the substituted or unsubstituted alkylene groups mentioned above can suitably be used as $R^{21}$ and $R^{22}$. The cyclic group B can be a divalent group obtained by elimination of two hydrogen atoms from the alicyclic hydrocarbon such as substituted or unsubstituted norbornane, adamantane, cyclohexane or cyclopentane, or a substituted or unsubstituted phenylene group. As a substituent group, there can be used: alkyl groups such as methyl, ethyl, n-propyl and i-propyl; and fluorine-containing alkyl groups such as fluoromethyl, difluoromethyl, trifluoromethyl, 2-fluoroethyl, 2,2-difluoroethyl, 2,2,2-trifluoroethyl, pentafluoroethyl, 1-methyl-2,2,2-trifluoroethyl, 1-(trifluoromethyl)-2,2,2-trifluoroethyl and 1-(trifluoromethyl)-1,2,2,2-tetrafluoroethyl. Among others, preferred are methyl and trifluoromethyl.

The following are specific examples of the structure represented by the general formula (1) of the polymerizable fluorine-containing sulfonic acid or sulfonate. The present invention is not however limited to these examples.

[Chem. 24]

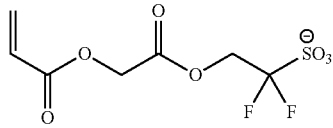

-continued

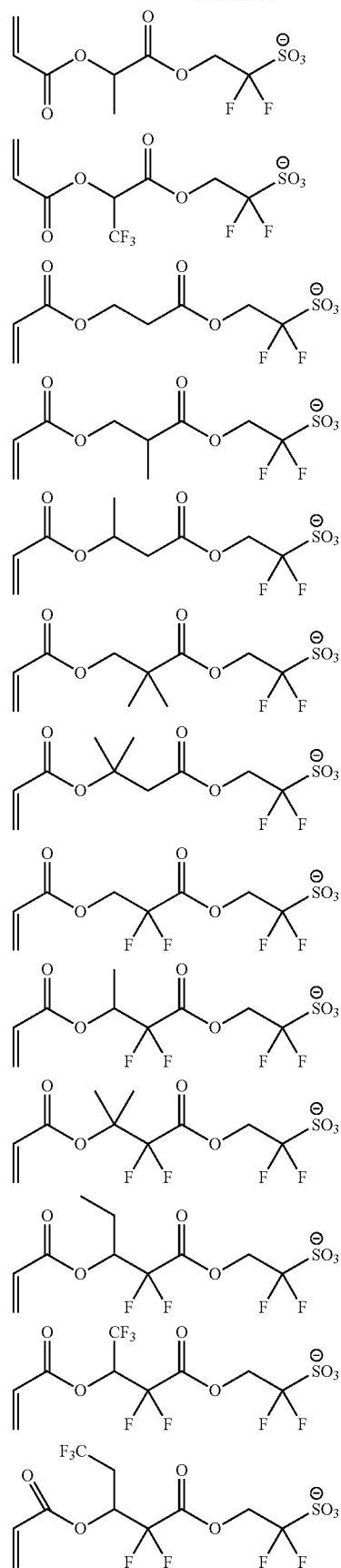

[Chem. 25]
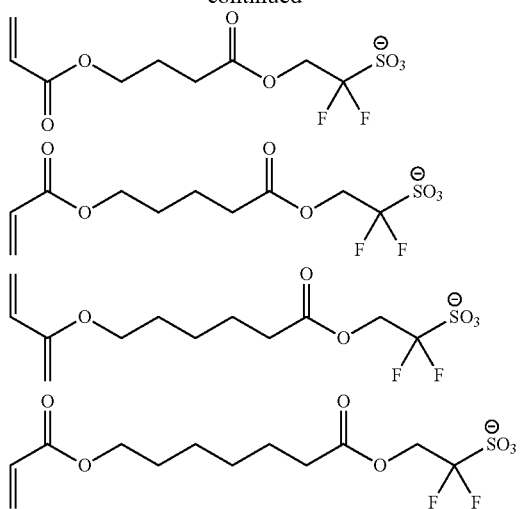
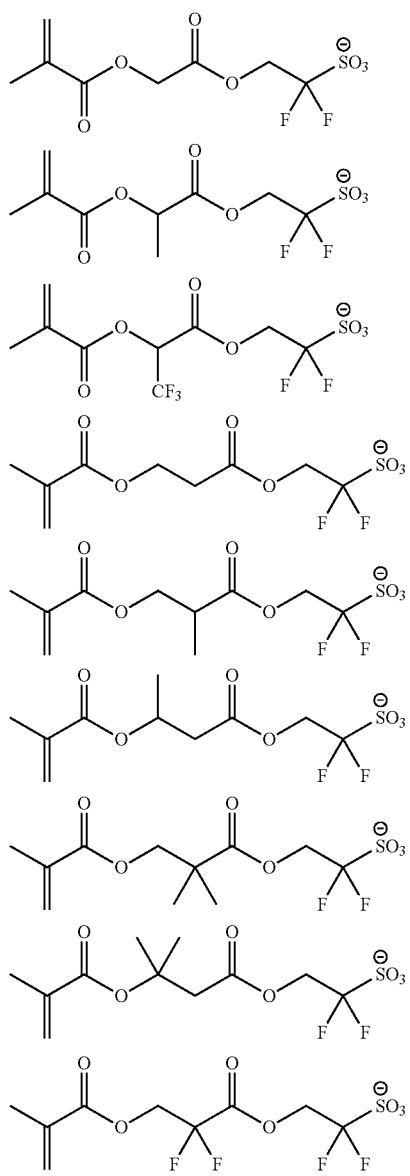
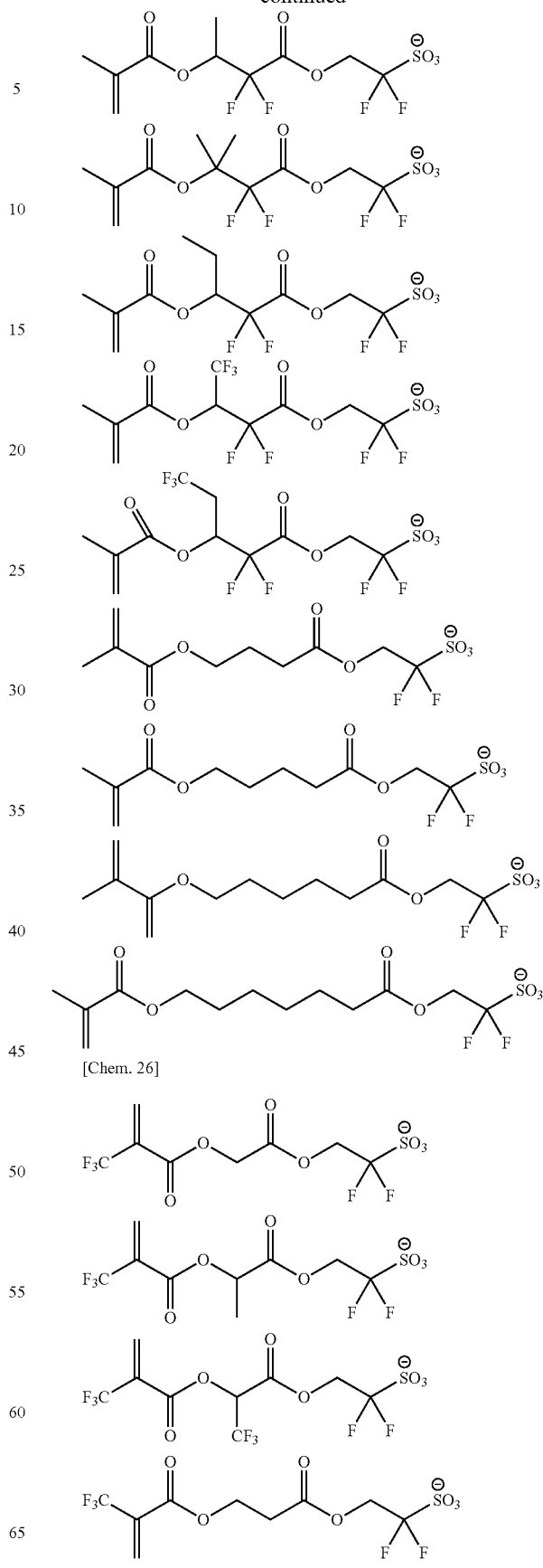
[Chem. 26]

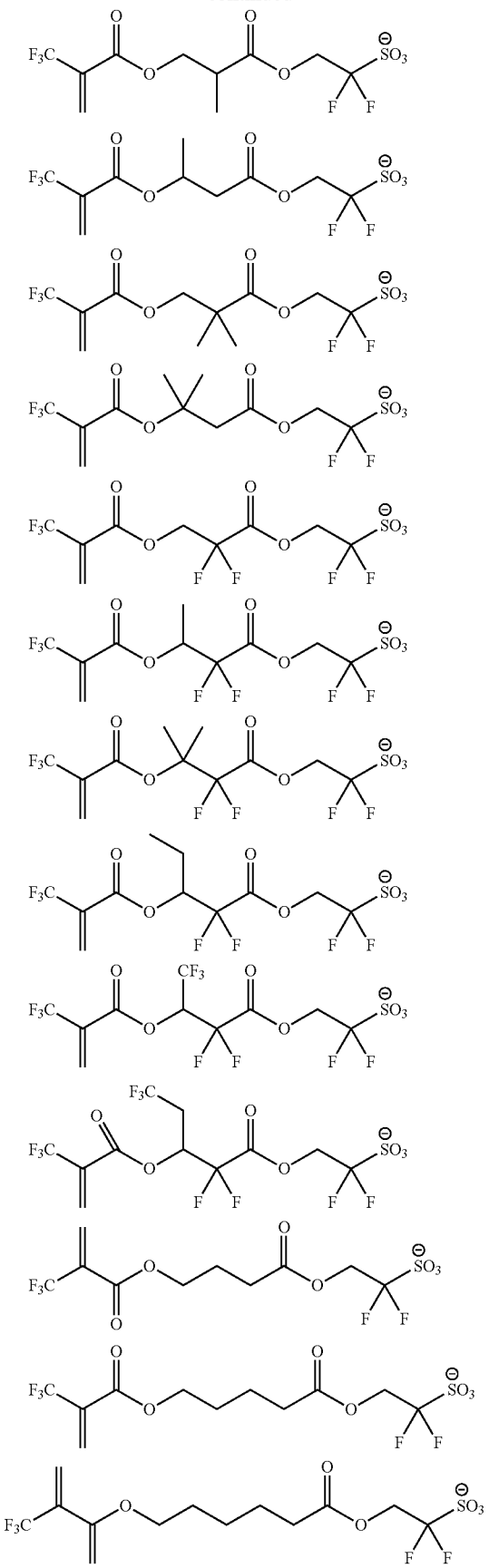
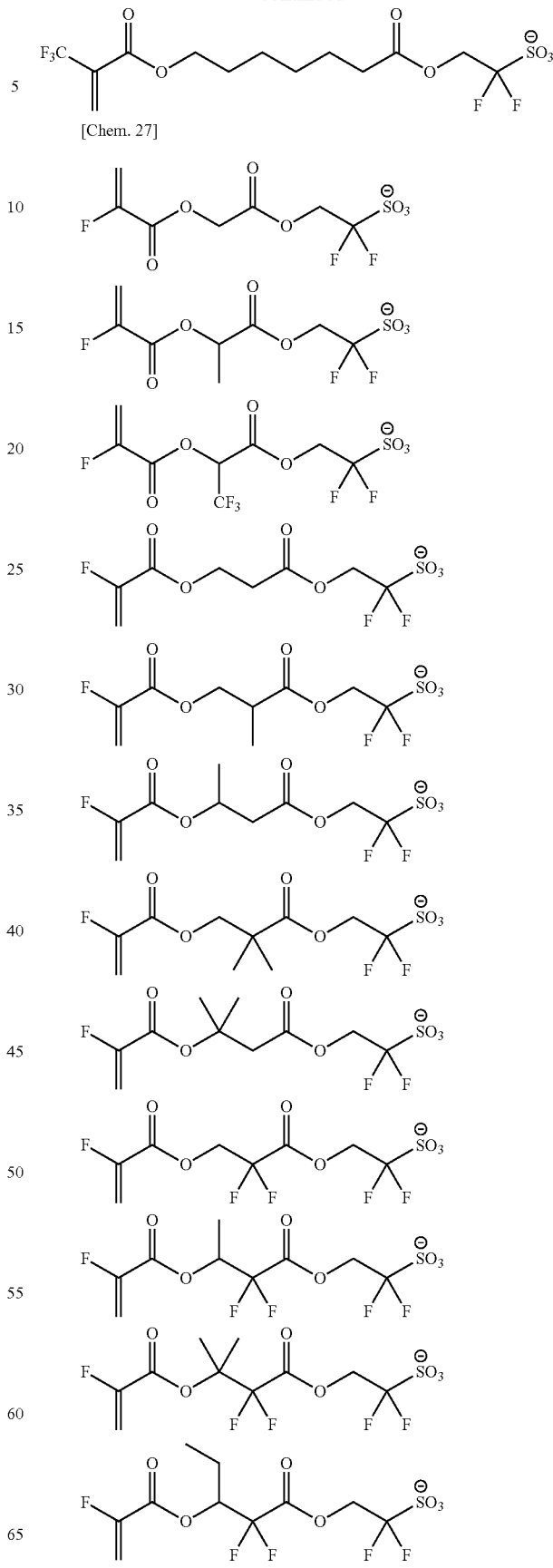

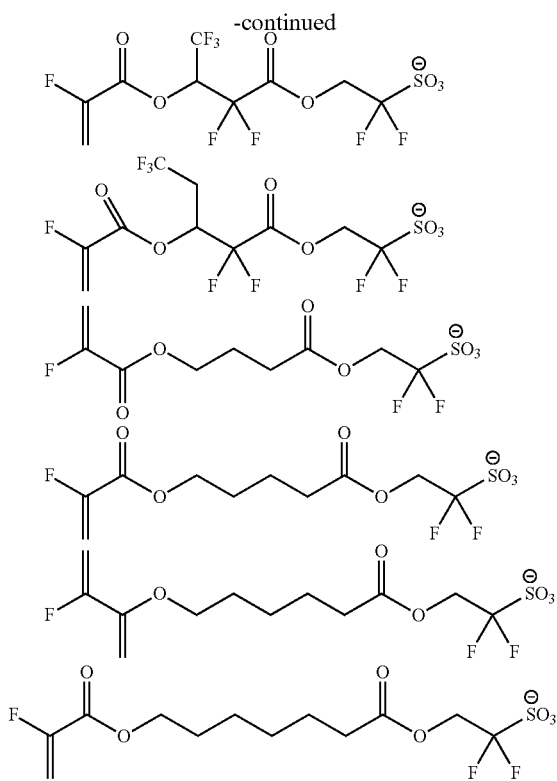

[Polymerizable Fluorine-Containing Sulfonic Acid Onium Salt]

A polymerizable fluorine-containing sulfonic acid onium salt of the general formula (2) is one kind of the polymerizable fluorine-containing sulfonate having the structure of the general formula (1) according to the present invention. This polymerizable fluorine-containing sulfonic acid onium salt (2), when used as a monomer or formed into a resin by homopolymerization or copolymerization, is capable of generating a sulfonic acid of very high acidity by exposure to high energy radiation such as ultraviolet radiation, far-ultraviolet radiation, extreme-ultraviolet (EUV) radiation, electron beam, X-ray, excimer laser beam, γ-ray or synchrotron radiation and thus can function as a photoacid generator. Further, the polymerizable fluorine-containing sulfonic acid onium salt (2) can be copolymerized with a monomer having an acid labile group or a cross-linking site and thus can be suitably used as a monomer for synthesis of a base resin for a high energy radiation resist composition.

[Chem. 28]

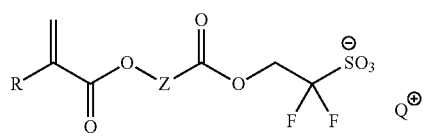
(2)

In the general formula (2), Z and R have the same definitions as in the general formula (1). Specific examples of Z and R are thus the same as those mentioned above. Further, Q$^+$ represents either a sulfonium cation of the general formula (a) or the general formula (b), or an iodonium cation of the general formula (c).

[Chem. 29]

(a)

[Chem. 30]

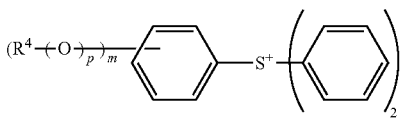
(b)

[Chem. 31]

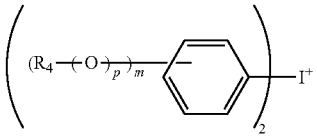
(c)

[Sulfonium Cation of General Formula (a)]

In the general formula (a), $R^1$, $R^2$ and $R^3$ each independently represent a substituted or unsubstituted $C_1$-$C_{20}$ straight, branched or cyclic alkyl, alkenyl or oxoalkyl group, or a substituted or unsubstituted $C_6$-$C_{18}$ aryl, aralkyl or aryloxoalkyl group. Any two or more of $R^1$, $R^2$ and $R^3$ may be bonded to each other to form a ring with a sulfur atom in the formula.

More specifically, $R^1$, $R^2$ and $R^3$ are exemplified as follows. Examples of the substituted or unsubstituted $C_1$-$C_{20}$ straight, branched or cyclic alkyl group are methyl, ethyl, n-propyl, isopropyl, cyclopropyl, n-butyl, sec-butyl, isobutyl, tert-butyl, n-pentyl, cyclopentyl, n-hexyl, n-heptyl, 2-ethylhexyl, cyclohexyl, cycloheptyl, 4-methylcyclohexyl, cyclohexylmethyl, n-octyl, n-decyl, 1-adamantyl, 2-adamantyl, bicyclo[2.2.1]heptene-2-yl, 1-adamantanemethyl and 2-adamantanemethyl. Examples of the substituted or unsubstituted $C_1$-$C_{20}$ straight or branched alkenyl group are vinyl, allyl, propenyl, butenyl, hexenyl and cyclohexenyl. Examples of the substituted or unsubstituted $C_1$-$C_{20}$ straight or branched oxoalkyl group are 2-oxocyclopentyl, 2-oxocyclohexyl, 2-oxopropyl, 2-oxoethyl, 2-cyclopentyl-2-oxoethyl, 2-cyclohexyl-2-oxoethyl and 2-(4-methylcyclohexyl)-2-oxoethyl. Examples of the substituted or unsubstituted $C_6$-$C_{18}$ aryl group are: phenyl; naphthyl; thienyl; alkoxylphenyl groups such as p-methoxyphenyl, m-methoxyphenyl, o-methoxyphenyl, p-ethoxypenyl, p-tert-butoxyphenyl and m-tert-butoxyphenyl; alkylphenyl groups such as 2-methylphenyl, 3-methylphenyl, 4-methylphenyl and ethylphenyl; alkylnaphthyl groups such as methylnaphthyl and ethylnaphthyl; dialkylnaphthyl groups such as diethylnaphthyl; and dialkoxynaphthyl groups such as dimethoxynaphthyl and diethoxynaphthyl. Examples of the substituted or unsubstituted $C_6$-$C_{18}$ aralkyl group are benzyl, 1-phenylethyl and 2-phenylethyl. Examples of the substituted or unsubstituted $C_6$-$C_{18}$ aryloxoalkyl group are 2-aryl-2-oxoethyl groups such as 2-phenyl-2-oxoethyl, 2-(1-naphthyl)-2-oxoethyl and 2-(2-naphthyl)-2-oxoethyl. In the case where two or more of $R^1$, $R^2$ and $R^3$ are bonded to each other to form a ring structure with the sulfur atom, there can be used divalent groups such as 1,4-butylene and 3-oxa-1,5-penthylene. There can also be used aryl groups with polymerizable substituents such as acryloyloxy and methacryloyloxy. Examples of the aryl groups with the polymerizable substituents are 4-(acryloyloxy)phenyl, 4-(methacryloyloxy)phenyl, 4-vinyloxyphenyl and 4-vinylphenyl.

Specific examples of the sulfonium cation of the general formula (a) are triphenylsulfonium, (4-tert-butylphenyl)diphenylsulfonium, bis(4-tert-butylphenyl)phenylsulfonium, tris(4-tert-butylphenyl)sulfonium, (3-tert-butylphenyl)diphenylsulfonium, bis(3-tert-butylphenyl)phenylsulfonium, tris(3-tert-buthylphenyl)sulfonium, (3,4-di-tert-butylphenyl)diphenylsulfonium, bis(3,4-di-tert-butylphenyl)phenylsulfonium, tris(3,4-di-tert-butylphenyl)sulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyediphenyl)sulfonium, tris(4-tert-butoxycarbonylmethyloxyphenyl)diphenylsulfonium, (4-tert-butoxyphenyl)bis(4-dimethylaminophenyl)sulfonium, tris(4-dimethylaminophenyl)sulfonium, 2-naphthyldiphenylsulfonium, dimethyl(2-naphthyl)sulfonium, (4-hydroxyphenyl)dimethylsulfonium, (4-methoxyphenyl)dimethylsulfonium, trimethylsulfonium, (2-oxocyclohexyl)cyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl 2-thienylsulfonium, 4-n-butoxynaphthyl-1-thiacyclopentanium, 2-n-butoxynaphthyl-1-thiacyclopentanium, 4-methoxynaphthyl-1-thiacyclopentanium and 2-methoxynaphthyl-1-thiacyclopentanium. Among others, preferred are triphenylsulfonium, (4-tert-buthylphenyl)diphenylsulfonium, (4-tert-butoxyphenyl)diphenylsulfonium, tris(4-tert-butylphenyl)sulfonium and (4-tert-butoxycarbonylmethyloxyphenyl)diphenylsulfonium.

Further, 4-(methacryloyloxy)phenyldiphenylsulfonium, 4-(acryloyloxy)phenyldiphenylsulfonium, 4-(methacryloyloxy)phenyldimethylsulfonium and 4-(acryloyloxy)phenyldimethylsulfonium are also specific examples of the sulfonium cation of the general formula (a). Polymerizable sulfonium cations disclosed in Japanese Laid-Open Patent Publication No. 4-230645 and Japanese Laid-Open Patent Publication No. 2005-84365 are also usable.

[Sulfonium Cation of General Formula (b)]

In the general formula (b), $R^4$—$(O)_p$— are independent of each other; and $R^4$ represents a substituted or unsubstituted $C_1$-$C_{20}$ straight, branched or cyclic alkyl or alkenyl group, or a substituted or unsubstituted $C_6$-$C_{14}$ aryl group. There is no particular limitation on the substitution position of $R^4$—$(O)_p$—. It is preferable that $R^4$—$(O)_p$— is in 4- or 3-position, more preferably 4-position, of the phenyl group. Herein, m represents an integer of 1 to 5; and p represents 0 or 1. Further, $R^4$ may contain a carbonyl group, a hydroxyl group, an ester bond, a lactone ring, an amino group, an amide group or an ether bond as a substituent group.

Examples of $R^4$ are methyl, ethyl, n-propyl, sec-propyl, cyclopropyl, n-butyl, sec-butyl, iso-butyl, tert-butyl, n-pentyl, cyclopentyl, n-hexyl, cyclohexyl, n-octyl, n-decyl, n-dodecyl, 1-adamantyl, 2-adamantyl, bicyclo[2.2.1]heptene-2-yl, phenyl, 4-methoxyphenyl, 4-tert-butylphenyl, 4-biphenyl, 1-naphthyl, 2-naphthyl, 10-anthranyl and 2-furanyl. In the case of p=1, acryloyl, methacryloyl, vinyl and allyl are usable. Preferred as $R^4$ are methyl, ethyl, n-hexyl, n-octyl, cyclohexyl, methoxy, ethoxy, tert-butoxy, cyclohexyloxy, trifluoromethyl, trifluoromethyloxy and tert-butoxycarbonylmethyloxy.

Specific examples of the sulfonium cation of the general formula (b) are (4-methylphenyl)diphenylsulfonium, (4-ethylphenyl)diphenylsulfonium, (4-cyclohexylphenyl)diphenylsulfonium, (4-n-hexylphenyl)diphenylsulfonium, (4-n-octylphenyl)diphenylsulfonium, (4-methoxyphenyl)diphenylsulfonium, (4-ethoxyphenyl)diphenylsulfonium, (4-tert-butoxyphenyl)diphenylsulfonium, (4-cyclohexyloxyphenyl)diphenylsulfonium, (4-trifluoromethylphenyl)diphenylsulfonium, (4-trifluoromethyloxyphenyl)diphenylsulfonium and (4-tert-butoxycarbonylmethyloxyphenyl)diphenylsulfonium.

[Iodonium Cation of General Formula (c)]

In the general formula (c), $R^4$—$(O)_p$— are independent of each other; and $R^4$ represents a substituted or unsubstituted $C_1$-$C_{20}$ straight, branched or cyclic alkyl or alkenyl group, or a substituted or unsubstituted $C_6$-$C_{14}$ aryl group. There is no particular limitation on the substitution position of $R^4$—$(O)_p$—. It is preferable that $R^4$—$(O)_p$— is in 4- or 3-position, more preferably 4-position, of the phenyl group. Herein, m represents an integer of 1 to 5; and p represents 0 or 1. Further, $R^4$ may contain a carbonyl group, a hydroxyl group, an ester bond, a lactone ring, an amino group, an amide group or an ether bond as a substituent group. Examples of $R^4$ in the general formula (c) are the same as those in the general formula (b).

Specific examples of the iodonium cation of the general formula (c) are bis(4-methylphenyl)iodonium, bis(4-ethylphenyl)iodonium, bis(4-tert-butylphenyl)iodonium, bis(4-(1,1-dimethylpropyl)phenyl)iodonium, (4-methoxyphenyl)phenyliodonium, (4-tert-butoxyphenyl)phenyliodonium, (4-acryloyloxy)phenylphenyliodonium and (4-methacryloyloxy)phenylphenyliodonium. Among others, bis(4-tert-butylphenyl)iodonium is preferred.

The following are preferred examples of the polymerizable fluorine-containing sulfonic acid onium salt of the general formula (2).

[Chem. 32]

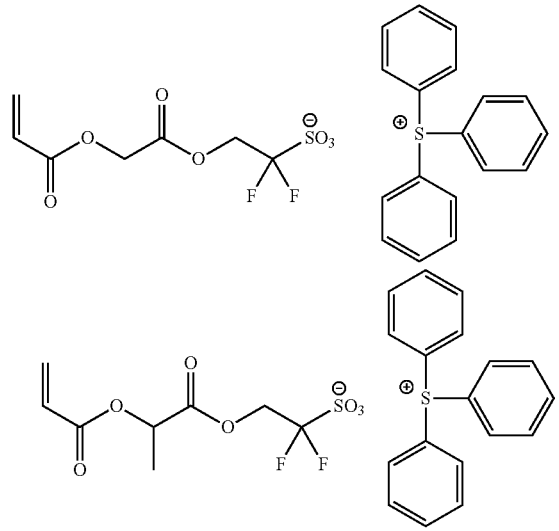

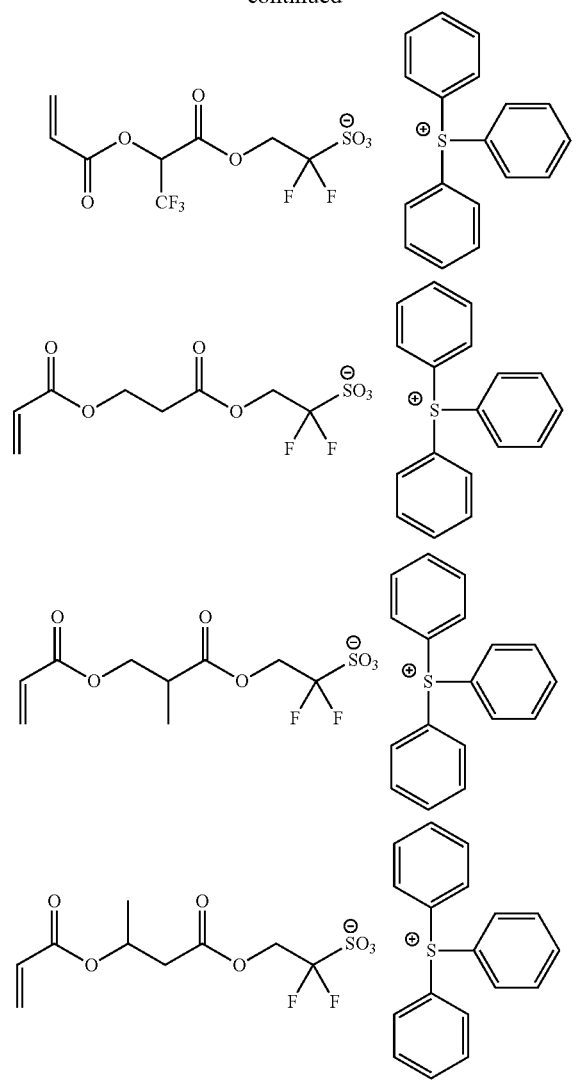
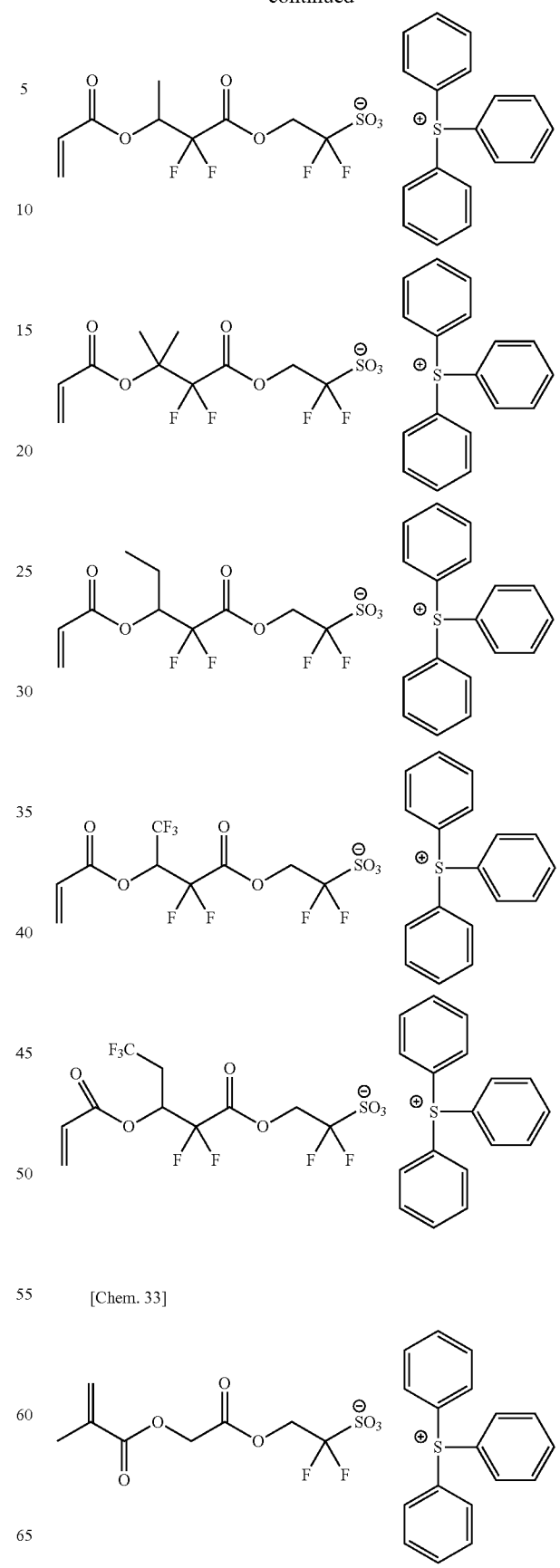
[Chem. 33]

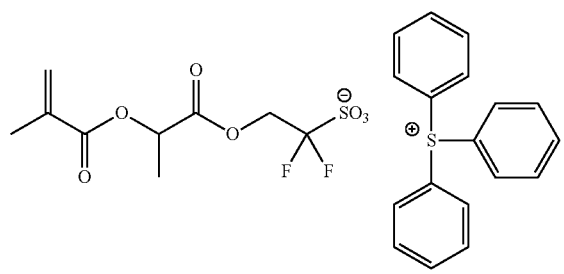
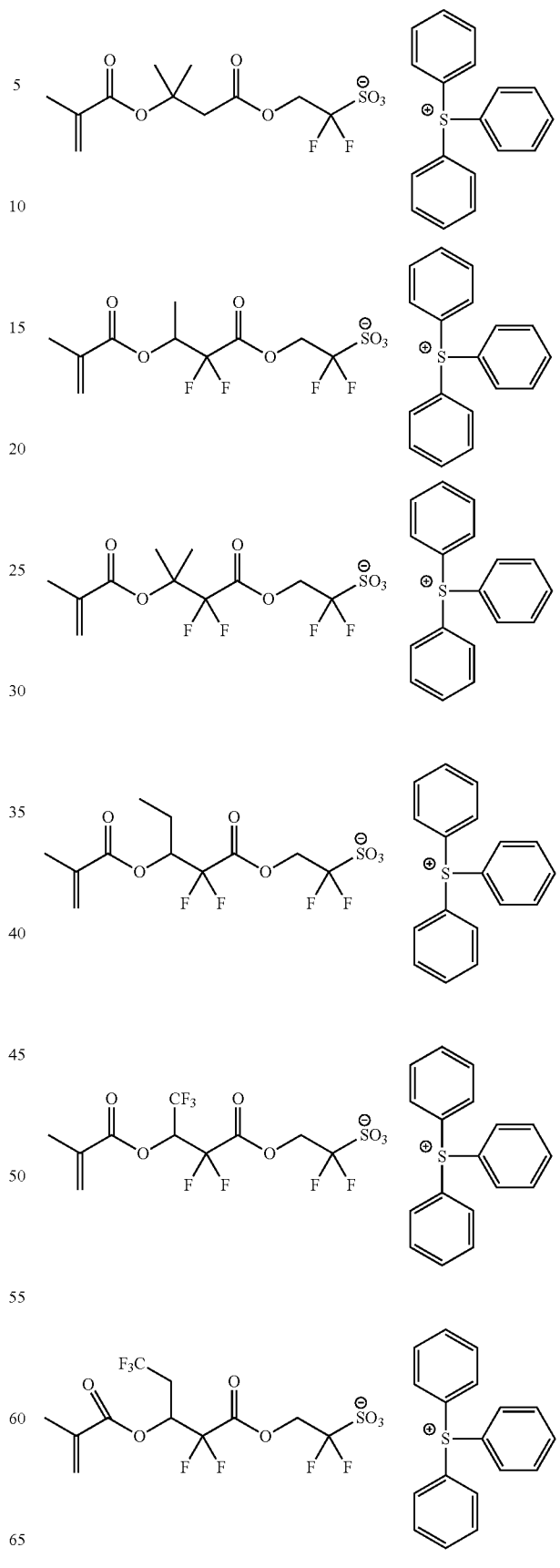

[Chem. 34]
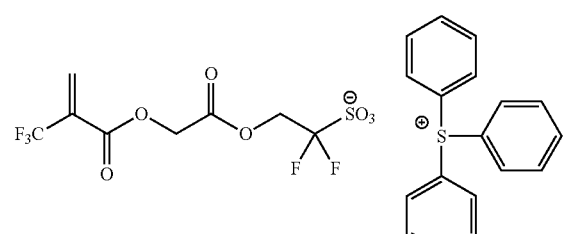
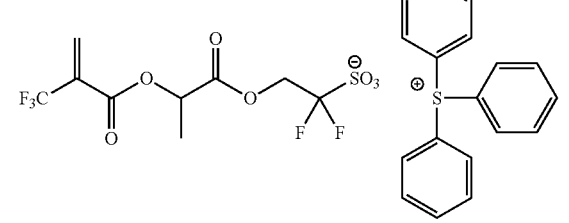
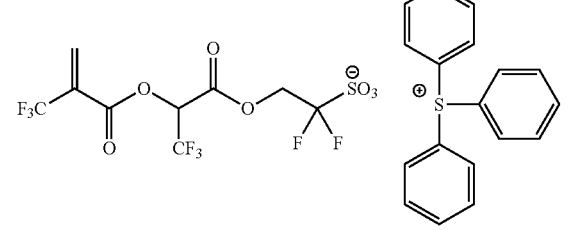
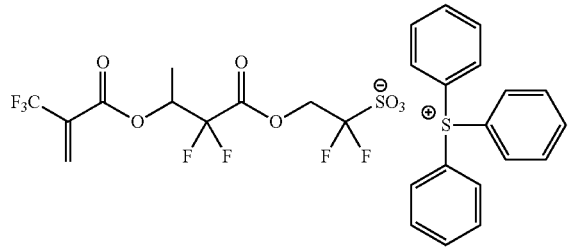
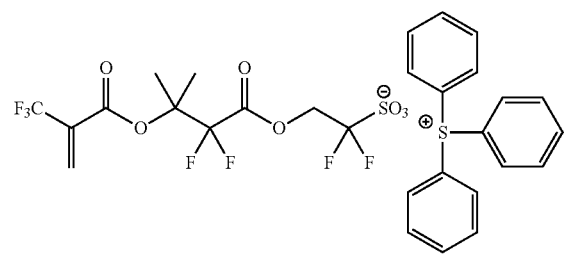
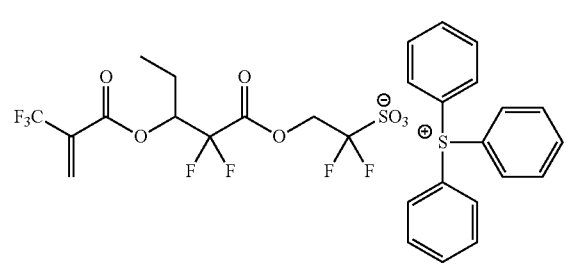
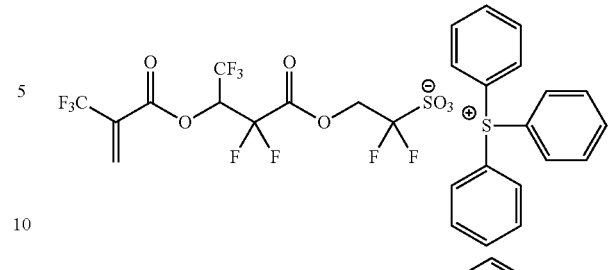
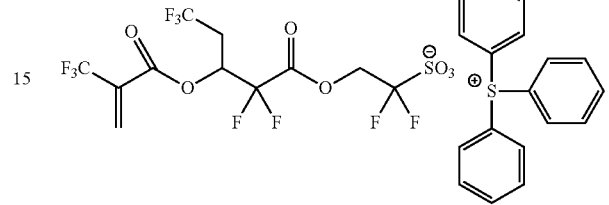
[Chem. 35]
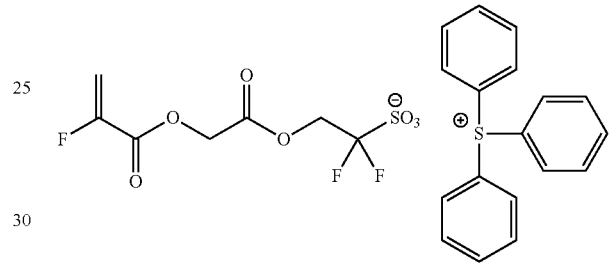
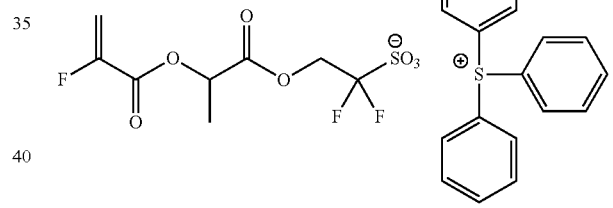
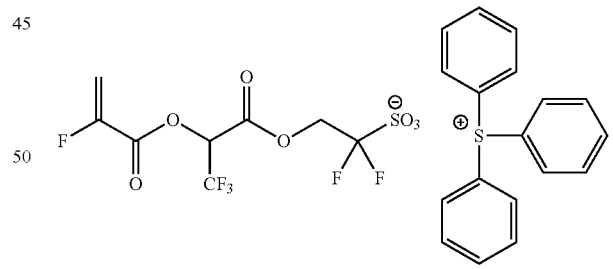
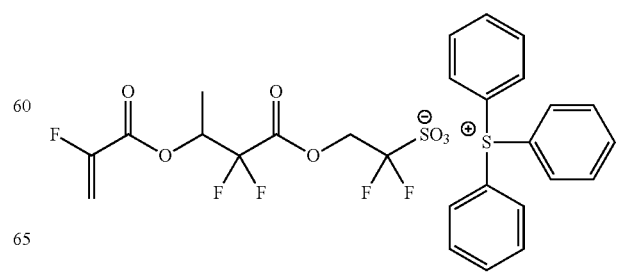

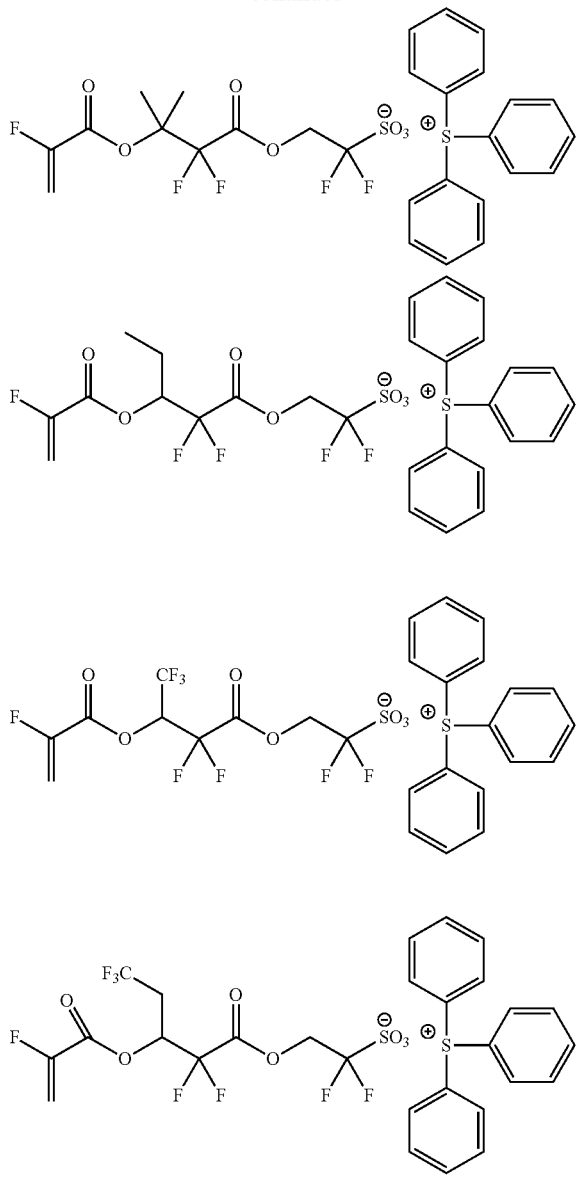

Particularly preferred are polymerizable fluorine-containing sulfonic acid onium salt compounds of the following general formulas (12) and (13).

[Chem. 36]

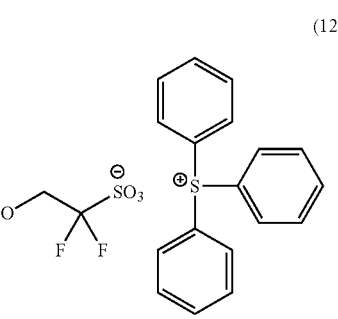

(12)

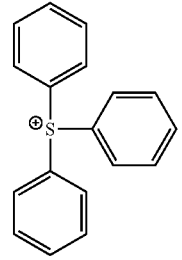

(13)

[Chem. 37]

[Polymerizable Fluorine-Containing Sulfonate Compound]

A polymerizable fluorine-containing sulfonate compound of the general formula (3) is useful as a raw material for production of the polymerizable fluorine-containing sulfonic acid onium salt (2) as one kind of the polymerizable fluorine-containing sulfonate (1) according to the present invention.

[Chem. 38]

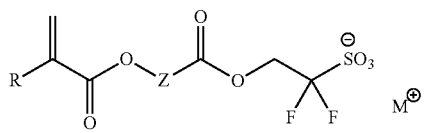

(3)

In the general formula (3), Z and R have the same definitions as in the general formula (1); and $M^+$ represents one of a lithium ion, a sodium ion, a potassium ion and ammonium ions.

Examples of the ammonium ions are ammonium ion ($NH_4^+$), methylammonium ion ($MeNH_3^+$), dimethylammonium ion ($Me_2NH_2^+$), trimethylammonium ion ($Me_3NH^+$), ethylammonium ion ($EtNH_3^+$), diethylammonium ion ($Et_2NH_2^+$), triethylammonium ion ($Et_3NH^+$), n-propylammonium ion (n-$PrNH_3^+$), di-n-propylammonium ion (n-$Pr_2NH_2$), tri-n-propylammonium ion (n-$Pr_3NH^+$), i-propylammonium ion (i-$PrNH_3^+$), di-i-propylammonium ion (i-$Pr_2NH_2^+$), tri-i-propylammonium ion (i-$Pr_3NH^+$), n-butylammonium ion (n-$BuNH_3^+$), di-n-butylammonium ion (n-$Bu_2NH_2^+$), tri-n-butylammonium ion (n-$Bu_3NH^+$), sec-butylammonium ion (sec-$BuNH_3^+$), di-sec-butylammonium ion (sec-$Bu_2NH_2^+$), tri-sec-butylammonium ion (sec-$Bu_3NH^+$), tert-butylammonium ion (t-$BuNH_3^+$), di-tert-butylammonium ion (t-$Bu_2NH_2^+$), tri-tert-butylammonium ion (t-$Bu_3NH^+$), diisopropylethylammonium ion (n-$Pr_2EtNH^+$), phenylammonium ion ($PhNH_3^+$), diphenylammonium ion ($Ph_2NH_2^+$), triphenylammonium ion ($Ph_3NH^+$), tetramethylammonium ion ($Me_4N^+$), tetraethylammonium ion ($Et_4N^+$), trimethylethylammonium ion ($Me_3EtN^+$), tetra-n-propylammonium ion (n-$Pr_4N^+$), tetra-i-propylammonium ion (i-$Pr_4N^+$), tetra-n-butylammonium ion (n-$Bu_4N^+$) and ammonium ions of the following structures.

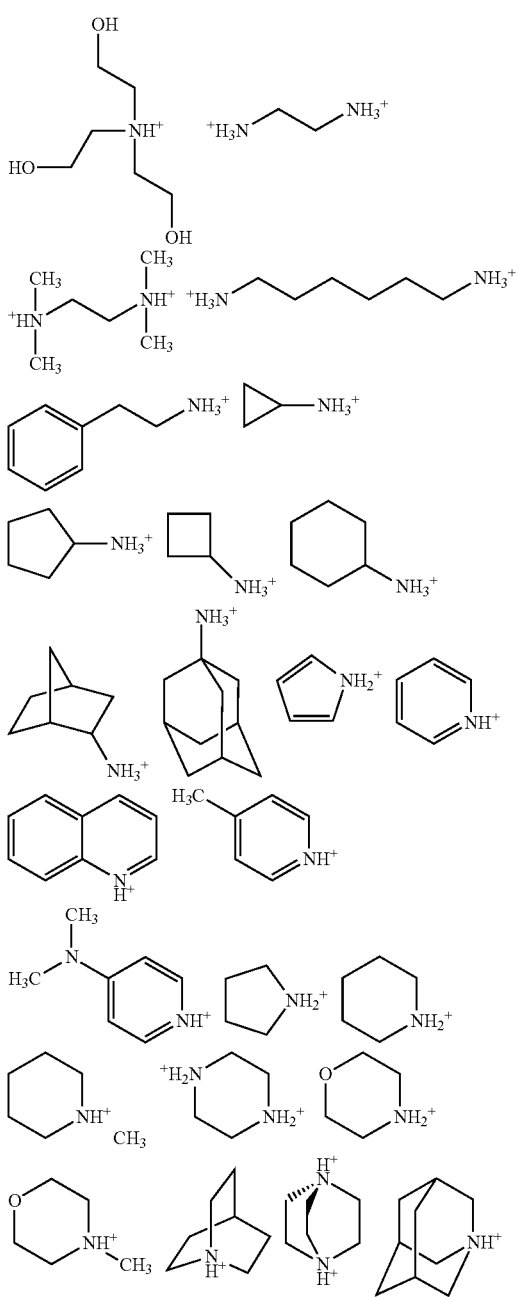

Among others, the ammonium ion is preferably an ammonium ion of the following formula (i):

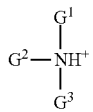

where $G^1$, $G^2$ and $G^3$ each independently represent a hydrogen atom, a $C_1$-$C_6$ alkyl group, a $C_1$-$C_6$ alkoxyalkyl group, a $C_3$-$C_{12}$ cycloalkyl group, a phenyl group which may have a substituent, a $C_7$-$C_{12}$ aralkyl group which may have a substituent, a naphthyl group which may have a substituent, or a $C_5$-$C_{10}$ hetero aromatic group which may have a substituent. At least two of $G^1$, $G^2$ and $G^3$ may be linked together to form a ring that may contain a hetero atom.

Particularly preferred are trimethylammonium ion ($Me_3NH^+$), triethylammonium ion ($Et_3NH^+$), tri-n-propylammonium ion (n-$Pr_3NH^+$), tri-i-propylammonium ion (i-$Pr_3NH^+$), tri-n-butylammonium ion (n-$Bu_3NH^+$), tri-sec-butylammonium ion (sec-$Bu_3NH^+$), tri-tert-butylammonium ion (t-$Bu_3NH^+$), diisopropylethylammonium ion (n-$Pr_2EtNH^+$), triphenylammonium ion ($Ph_3NH^+$) and ammonium ions of the following structures.

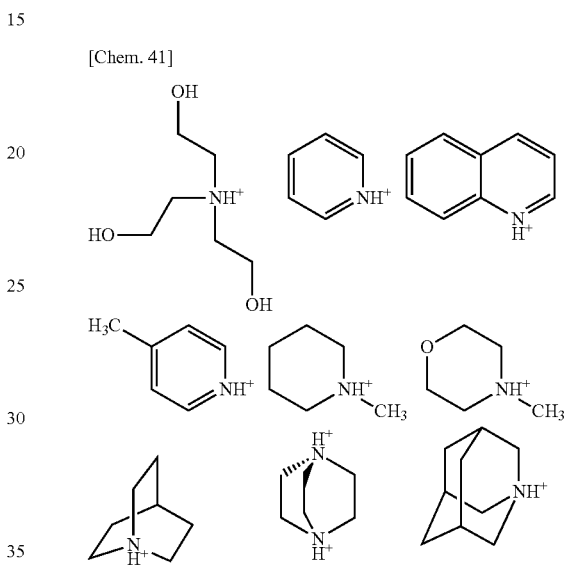

Among others, trimethylammonium ion ($Me_3NH^+$), triethylammonium ion ($Et_3NH^+$) and diisopropylethyl ammonium ion (n-$Pr_2EtNH^+$) are more particularly preferred.

The following are preferred examples of the polymerizable fluorine-containing sulfonate compound of the general formula (3).

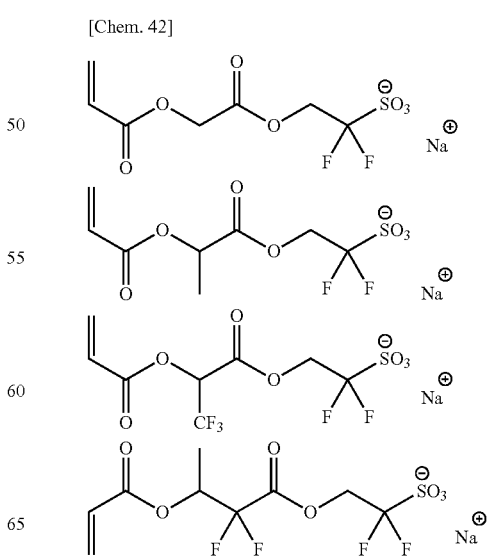

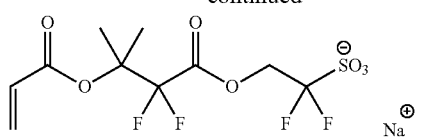
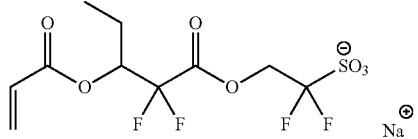
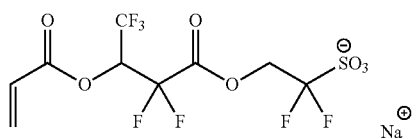
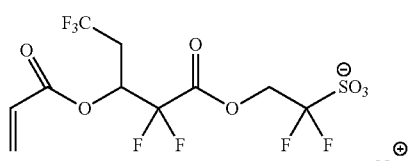
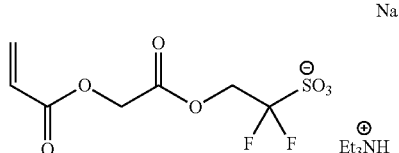
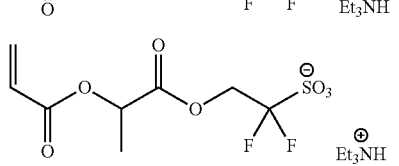
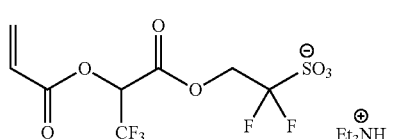
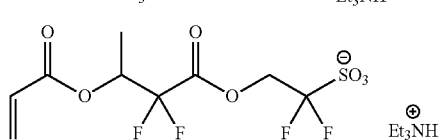
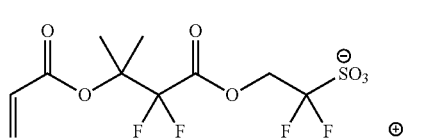
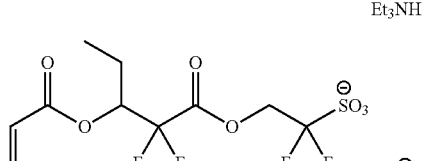
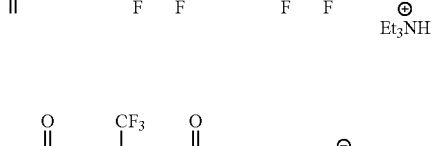
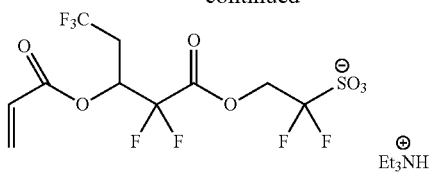
[Chem. 43]
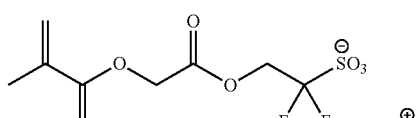
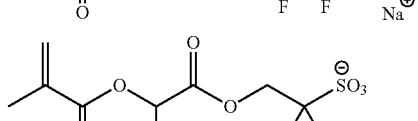
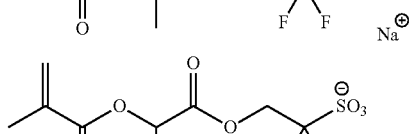
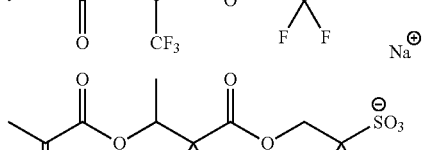
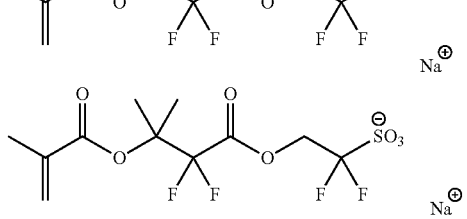
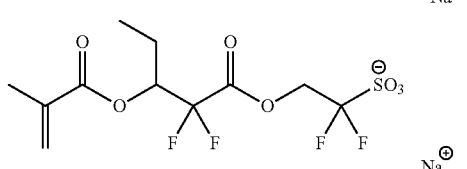
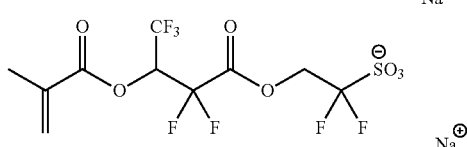
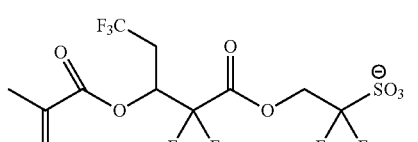
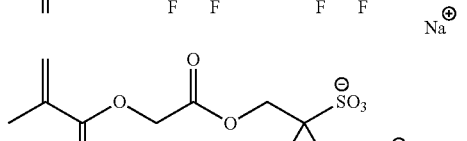
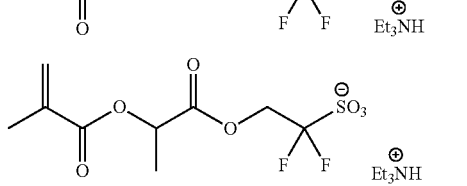

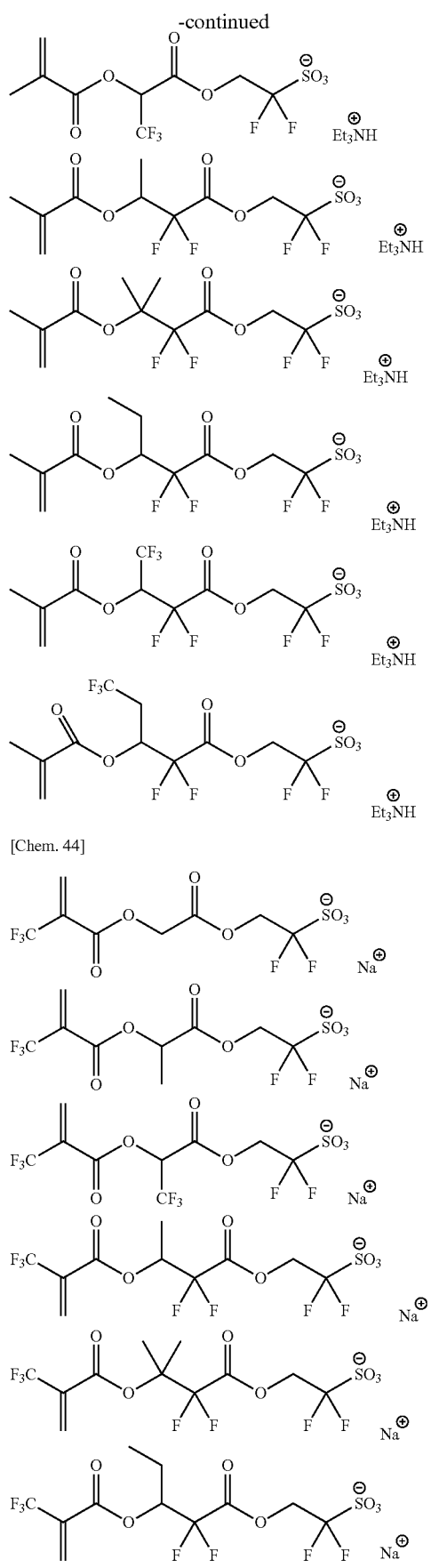
[Chem. 44]
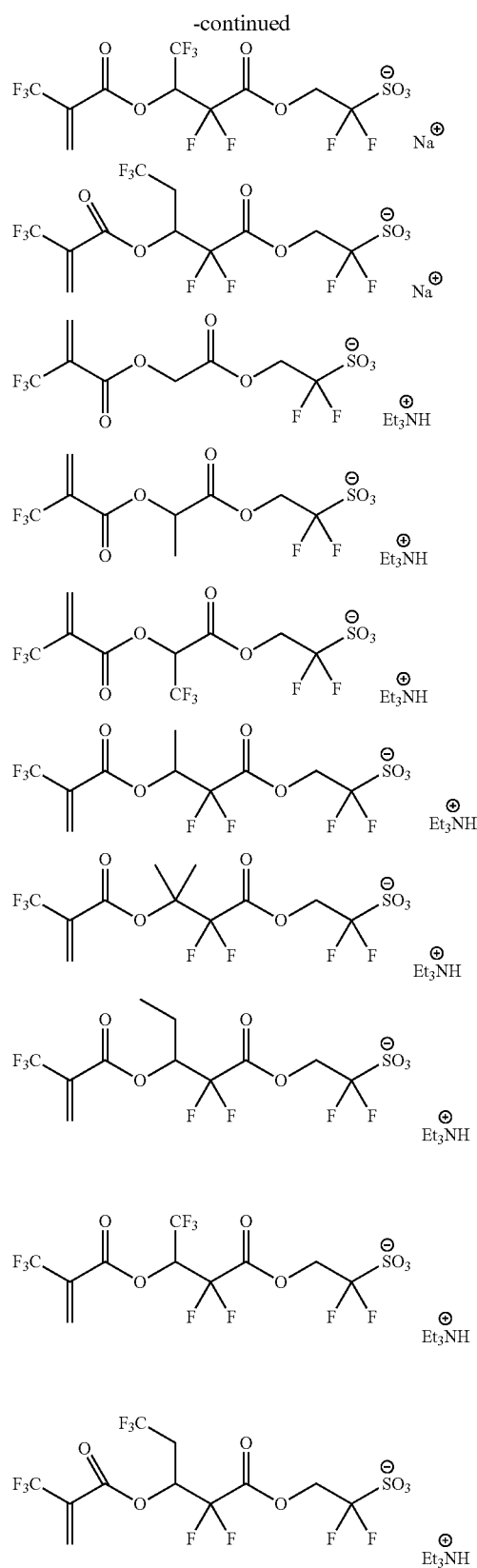
Particularly preferred are polymerizable fluorine-containing sulfonate compounds of the following general formulas (14) and (15).

[Chem. 45]

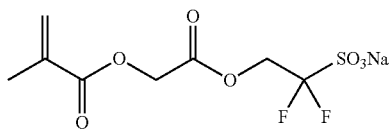

(14)

[Chem. 46]

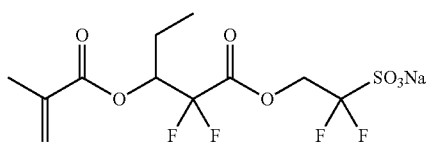

(15)

[Production Method of Polymerizable Fluorine-Containing Sulfonate]

A production method of the polymerizable fluorine-containing sulfonic acid onium salt of the general formula (2) and the polymerizable fluorine-containing sulfonate compound of the general formula (3) is as follows.

The polymerizable fluorine-containing sulfonate compound of the general formula (3) can be easily obtained by known esterification reaction of the carboxylic acid derivative of the following general formula (16) and the 1,1-difluoro-2-hydroxyethanesulfonate of the following general formula (17) as indicated in SCHEME (1).

[Chem. 47]

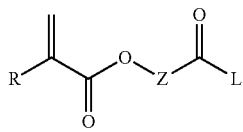

(16)

In the general formula (16), Z and R have the same definitions as in the general formula (1); and L represents a hydroxyl group or a halogen atom.

[Chem. 48]

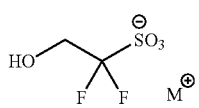

(17)

In the general formula (17), $M^+$ has the same definition as in the general formula (3).

As indicated in SCHEME (2), the carboxylic acid derivative of the general formula (16) can be, for example, in the form of an acid of the general formula (21) prepared by esterification of an acid anhydride or acid halide of the general formula (19) with a hydroxyalkanoic acid of the general formula (20) or in the form of an acid chloride of the general formula (22) prepared by chlorination of the acid of the general formula (21).

SCHEME (2)

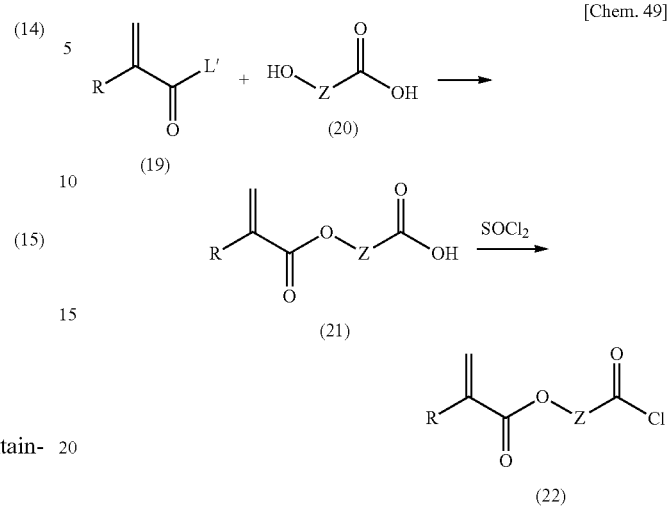

In SCHEME (2), Z and R have the same definitions as in the general formula (1); and L' represents either a —O(C=O)C(R)=CH$_2$ group or a halogen atom.

On the other hand, the 1,1-difluoro-2-hydroxyethanesulfonate of the general formula (17) can be prepared by reducing ethyl bromodifluoroacetate to 2-bromo-2,2-difluoroethanol, esterifying the 2-bromo-2,2-difluoroethanol with pivaloyl chloride to form 2-bromo-2,2-difluoroethyl pivalate, sulfinating the 2-bromo-2,2-difluoroethyl pivalate to form 1,1-difluoro-2-(pivaloyloxy)ethanesulfinate, oxidizing the 1,1-difluoro-2-(pivaloyloxy)ethanesulfinate to 1,1-difluoro-2-(pivaloyloxy)ethanesulfonate, and then, saponifying the 1,1-difluoro-2-(pivaloyloxy)ethanesulfonate. Any known esterification technique can be adopted to react the carboxylic acid derivative of the general formula (16) and the 1,1-difluoro-2-hydroxyethanesulfonate of the general formula (17) for production of the polymerizable fluorine-containing sulfonate compound of the general formula (3) as indicated in SCHEME (1).

One example of the esterification technique is to conduct dehydration condensation reaction between the carboxylic acid of the general formula (16) (where L is hydroxyl) and the 1,1-difluoro-2-hydroxyethanesulfonate of the general formula (17) in the presence of an acid catalyst (as is known as Fischer ester synthesis reaction). Another example of the esterification technique is to react the carboxylic acid halide of the general formula (16) (where L is halogen) with the 1,1-difluoro-2-hydroxyethanesulfonate of the general formula (17).

In the case of using the carboxylic acid of the general formula (16) (where L is hydroxyl), there is no particular limitation on the amount of the carboxylic acid of the general formula (16) used relative to the 1,1-difluoro-2-hydroxyethanesulfonate of the general formula (17). The amount of the carboxylic acid of the general formula (16) used is generally in the range of 0.1 to 5 mol, preferably 0.2 to 3 mol, more preferably 0.5 to 2 mol, per 1 mol of the 1,1-difluoro-2-hydroxyethanesulfonate of the general formula (17). It is particularly preferable to use 0.8 to 1.5 mol of the carboxylic acid of the general formula (16) per 1 mol of the 1,1-difluoro-2-hydroxyethanesulfonate of the general formula (17).

The esterification reaction is performed in the presence or absence of a solvent, generally preferably in the presence of an aprotic solvent. Examples of the aprotic solvent are dichloroethane, toluene, ethylbenzene, monochlorobenzene, acetonitrile and N,N-dimethylformamide. These solvents can be used solely or in combination of two or more thereof. Although the 1,1-difluoro-2-hydroxyethnesulfonate of the general formula (17) is hardly dissolved in the aromatic hydrocarbon solvent such as toluene, ethylbenzene or monochlorobenzene and is present as a slurry in the aromatic hydrocarbon solvent, the reaction can proceed even in such a slurry state.

There is no particular limitation on the reaction temperature. The reaction temperature is generally in the range of 0 to 200° C., preferably 20 to 180° C., more preferably 50 to 150° C. It is preferable that the reaction is performed under stirring.

The reaction time is varied depending on the reaction temperature and is generally in the range of several minutes to 100 hours, preferably 30 minutes to 50 hours, more preferably 1 to 20 hours. It is desirable to determine the time at which the raw 1,1-difluoro-2-hydroxyethanesulfonate compound has been consumed as the end of the reaction while monitoring the progress of the reaction by any analytical means such as gas chromatography (GC) or nuclear magnetic resonance (NMR).

In general, the esterification reaction is performed in the presence of a catalyst, preferably an acid catalyst. As the acid catalyst, there can be used any known catalyst for esterification such as an organic acid e.g. p-toluenesulfonic acid and/or an inorganic acid e.g. sulfuric acid. Further, a dehydrating agent such as 1,1-carbonyldiimidazole or N,N≡-dicyclohexylcarbodiimide may be added into the reaction system. There is no particular limitation on the amount of the acid catalyst used. The amount of the acid catalyst used is generally in the range of 0.0001 to 10 mol, preferably 0.001 to 5 mol, more preferably 0.01 to 1.5 mol, per 1 mole of the 1,1-difluoro-2-hydroxyethanesulfonate.

It is preferable to perform the esterification reaction using the acid catalyst while dehydrating the reaction system e.g. by means of a Dean-Stark apparatus for reduction of the reaction time.

After the completion of the reaction, the polymerizable fluorine-containing sulfonate compound of the general formula (3) can be obtained by ordinary means such as extraction, distillation, recrystallization etc. The polymerizable fluorine-containing sulfonate compound of the general formula (3) may be purified by recrystallization etc. as needed.

In the case of using the carboxylic acid halide of the general formula (16) (where L is halogen), there is no particular limitation on the amount of the carboxylic acid halide of the general formula (16) used relative to the 1,1-difluoro-2-hydroxyethanesulfonate of the general formula (17). The amount of the carboxylic acid halide of the general formula (16) used is generally in the range of 0.1 to 5 mol, preferably 0.2 to 3 mol, more preferably 0.5 to 2 mol, per 1 mol of the 1,1-difluoro-2-hydroxyethanesulfonate of the general formula (17). It is particularly preferable to use 0.8 to 1.5 mol of the carboxylic acid halide of the general formula (16) per 1 mol of the 1,1-difluoro-2-hydroxyethanesulfonate of the general formula (17).

In this case, the reaction is performed in the absence of a solvent or in the presence of a solvent inert to the reaction. There is no particular limitation on the solvent as long as the solvent is inert to the reaction. As such a solvent, there can be used water, an organic solvent or a mixture thereof. Example of the organic solvent are: ketone solvents such as acetone, methyl ethyl ketone and methyl isobutyl ketone; ester solvents such as ethyl acetate and butyl acetate; ether solvents such as diethyl ether, diethylene glycol monoethyl ether, tetrahydrofuran and dioxane; halogenated solvents such as dichloromethane, chloroform, carbon tetrachloride, 1,2-dichloroethane, tetrachloroethylene, chlorobenzene and oxochlorobenzene; and polar solvents such as acetonitrile, N,N-dimethylformamide, N,N-dimethylimidazolidinone, dimethyl sulfoxide and sulfolane. These organic solvents can be used solely or in combination of two or more thereof.

There is no particular limitation on the reaction temperature. The reaction temperature is generally in the range of −78 to 150° C., preferably −20 to 120° C., more preferably 0 to 100° C.

The reaction time is varied depending on the reaction temperature and is generally in the range of several minutes to 100 hours, preferably 30 minutes to 50 hours, more preferably 1 to 20 hours. It is desirable to determine the time at which the raw 1,1-difluoro-2-hydroxyethanesulfonate compound has been consumed as the end of the reaction while monitoring the progress of the reaction by any analytical means such as gas chromatography (GC) or nuclear magnetic resonance (NMR).

It is feasible, in the case of using the carboxylic acid halide of the general formula (16) (where L is halogen), to perform the reaction in the absence of the catalyst while removing a hydrogen halide by-product (such as hydrogen chloride) from the reaction system. The reaction may be performed with the use of a dehydrohalogenating agent (as an acid acceptor).

Examples of the acid acceptor are: organic bases such as triethylamine, pyridine, picoline, dimethylaniline, diethylaniline, 1,4-diazabicyclo[2.2.2]octane (DABCO), 1,8-diazabicyclo[5.4.0]undeca-7-ene (DBU); and inorganic bases such as sodium hydrogen carbonate, sodium carbonate, potassium carbonate, lithium carbonate, sodium hydroxide, potassium hydroxide, calcium hydroxide and magnesium oxide. There is no particular limitation on the amount of the acid acceptor used. The amount of the acid acceptor used is generally in the range of 0.05 to 10 mol, preferably 0.1 to 5 mol, more preferably 0.5 to 3 mol, per 1 mol of the 1,1-difluoro-2-hydroxyethanesulfonate.

After the completion of the reaction, the polymerizable fluorine-containing sulfonate compound of the general formula (3) can be obtained by ordinary means such as extraction, distillation, recrystallization etc. The polymerizable fluorine-containing sulfonate compound of the general formula (3) may be purified by recrystallization etc. as needed.

The polymerizable fluorine-containing sulfonic acid onium salt of the general formula (2) can be easily obtained by onium salt exchange reaction of the polymerizable fluorine-containing sulfonate compound of the general formula (3) with a monovalent onium salt of the following general formula (18) according to any means known for salt exchange reaction of analogs.

[Chem. 50]

$$Q^+Y^- \tag{18}$$

In the general formula (18), $Q^+$ has the same definition as in the general formula (2) and, more specifically, the anion of the following general formula (a), (b) or (c); and $Y^-$ represents a monovalent anion. Examples of $Y^-$ are $F^-$, $Cl^-$, $Br^-$, $I^-$, $ClO_4^-$, $HSO_4^-$, $H_2PO_4^-$, $BF_4^-$, $PF_6^-$, $SbF_6^-$, aliphatic sulfonate anions, aromatic sulfonate anions, trifluoromethanesulfonate anion, fluorosulfonate anion, aliphatic carboxylate anions, aromatic carboxylate anions, fluorocarboxylate anion and trifluoroacetate anion. Among others, $Cl^-$, $Br^-$, $HSO_4^-$, $BF_4^-$ and aliphatic sulfonate ions are preferred. Particularly preferred are $Cl^-$, $Br^-$ and $HSO_4^-$.

In this onium salt exchange reaction, the mole ratio of the monovalent onium salt of the general formula (18) relative to the polymerizable fluorine-containing sulfonate compound of the general formula (3) is generally in the range of 0.5 to 10, preferably 0.8 to 2, more preferably 0.9 to 1.2.

Further, this reaction is generally performed in the presence of a reaction solvent. Preferred examples of the reaction solvent are water and organic solvents such as lower alcohols, tetrahydrofuran, N,N-dimethylformamide, N,N-dimethylacetamide, acetonitrile and dimethylsulfoxide. Among others, water, methanol, N,N-dimethylacetamide, acetonitrile and dimethylsulfoxide are more preferred. Particularly preferred is water. Water and organic solvent may be used in combination as needed. In this case, the amount of the water used is generally 5 parts by mass or more, preferably 10 parts by mass or more, more preferably 20 to 90 parts by mass, per 100 parts by mass of the sum of the water and organic solvent. The amount of the reaction solvent used is generally in the range of 1 to 100 parts by mass, preferably 2 to 100 parts by mass, more preferably 5 to 50 parts by mass, per 1 part by mass of the polymerizable fluorine-containing sulfonate compound.

The reaction temperature is generally in the range of 0 to 80° C., preferably 5 to 30° C. The reaction time is generally in the range of 10 minutes to 16 hours, preferably 30 minutes to 6 hours. It is desirable to determine the time at which the raw polymerizable fluorine-containing sulfonate compound has been consumed as the end of the reaction while monitoring the progress of the reaction by any analytical means such as thin layer chromatography (TLC) or nuclear magnetic resonance (NMR).

The polymerizable fluorine-containing sulfonic acid onium salt of the general formula (2) may be washed with an organic solvent or extracted and purified as needed. Preferred examples of the organic solvent are those incapable of mixing with water, such as esters e.g. ethyl acetate and n-butyl acetate, ethers e.g. diethyl ether and halogenated alkyls e.g. methylene chloride and chloroform. It is feasible to purify the polymerizable fluorine-containing sulfonic acid onium salt of the general formula (2) by recrystallization, column chromatography or the like.

[Sulfonate Resin]

One example of a resin having a repeating unit formed by cleavage of a polymerizable double bond of the polymerizable fluorine-containing sulfonic acid onium salt of the general formula (2), i.e., a resin having a repeating unit formed from the polymerizable fluorine-containing sulfonic acid or sulfonate having the structure of the general formula (1) (hereinafter referred to as "sulfonate resin") is a resin having a repeating unit of the following general formula (4)

[Chem. 51]

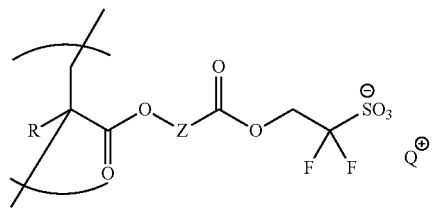

(4)

The resin having the repeating unit of the general formula (4) is converted to a resin having a repeating unit of the following general formula (5) by exposure to high energy radiation.

[Chem. 52]

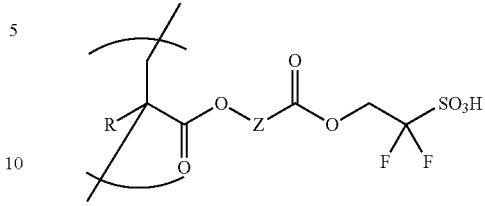

(5)

There is no particular limitation on the high energy radiation. Examples of the high energy radiation are those produced by produced by an excimer laser e.g. KrF excimer laser, ArF excimer laser or $F_2$ excimer laser or synchrotron radiation, such as near-ultraviolet radiation, far-ultraviolet radiation, extreme ultraviolet (EUV) radiation, soft X-ray, X-ray and γ-ray, and charged particle beam e.g. electron beam. In the case of fine processing, it is particularly effective to use high energy radiation of 300 nm or less wavelength, such as near-ultraviolet radiation, far-ultraviolet radiation or extreme ultraviolet (EUV) radiation, produced by an excimer laser e.g. KrF excimer laser, ArF excimer laser or $F_2$ excimer laser or synchrotron radiation.

After the elimination of $Q^+$, the repeating unit has a difluorosulfonic acid of very high acidity at an end thereof and thus can function as a photoacid generator of a chemically amplified resist composition. In other words, the resin having at least the repeating unit of the general formula (4) functions as a photoacid generator so that a composition containing at least such a positive or negative photosensitive solubility-changeable resin and a solvent can be used as a resist composition.

Depending on the purpose of use, the sulfonate resin consists of the repeating unit of the general formula (4) or has not only the repeating unit of the general formula (4) but another repeating unit containing an acid labile group or a cross-linking site. The sulfonate resin may further have any other repeating unit. Hereinafter, any repeating unit other than the repeating unit of the general formula (4) and the repeating unit containing the acid labile group or cross-linking site is referred to as "auxiliary repeating unit"; and any monomer capable of forming the auxiliary repeating unit by double bond cleavage is referred to as "auxiliary monomer".

Namely, the sulfonate resin can be in the form of a homopolymer consisting of the repeating unit of the general formula (4), which is obtained by homopolymerization of the polymerizable fluorine-containing sulfonic acid onium salt having the structure of the general formula (2), or can be in the form of a copolymer having the repeating unit of the general formula (4) and the auxiliary repeating unit. In these cases, the sulfonate resin itself cannot be used as a positive or negative resist resin, but can form a resist composition with a base resin and function as a photoacid generator. For the purpose of such use, the sulfonate resin contains 0.1 to 100 mol %, preferably 1 to 100 mol %, more preferably 2 to 100 mol %, of the polymerizable fluorine-containing sulfonic acid onium salt having the structure of the general formula (2), with the balance being the auxiliary repeating unit. If the amount of the polymerizable fluorine-containing sulfonic acid onium salt is less than 0.1 mol %, it is unfavorably necessary to use a large amount of photoacid generator in the resist composition in order for the resist composition to maintain sufficient photosensitivity to high energy radiation.

Alternatively, it is feasible that the sulfonate resin can consist of the repeating unit containing the acid labile group or cross-linking site and the repeating unit of the general formula (4). In this case, the sulfonate resin contains 0.1 to 90 mol %, preferably 0.5 to 50 mol %, more preferably 1 to 30 mol %, of the repeating unit of the general formula (4), with the balance being the repeating unit containing the acid labile group or cross-linking site. If the amount of the repeating unit of the general formula (4) is less than 0.1 mol %, the sulfonate resin does not show sufficient photosensitivity as the photoacid generator so that it is unfavorably necessary to use another photoacid generator without being able to sufficient use of the high performance of the sulfonate resin. If the amount of the repeating unit of the general formula (4) exceeds 90 mol %, the sulfonate resin can adequately function as the photoacid generator but unfavorably cannot take advantage of adding the repeating unit containing the acid labile group or cross-linking site in the resin. It is also feasible that the sulfonate resin can has the repeating unit containing the acid labile group or cross-linking site, the repeating unit of the general formula (4) and the auxiliary repeating unit. In this case, the sulfonate resin contains 0.1 to 70 mol %, preferably 1 to 60 mol %, more preferably 10 to 50 mol %, of the auxiliary repeating unit, with the balance being the repeating unit containing the acid labile group or cross-linking site and the repeating unit of the general formula (4). If the amount of the auxiliary repeating unit is less than 0.1 mol %, it is unfavorably difficult to control the adhesion of the resist resin to the substrate and the etching resistance of the resist resin. If the amount of the auxiliary repeating unit exceeds 70 mol %, it is unfavorably difficult to make sufficient use of the function of the sulfonate resin as the photoacid generator or the positive or negative resist resin in the present invention.

More specifically, in the case where the sulfonate resin functions not only as the photoacid generator but as the positive or negative resist resin, the sulfonate resin contains 1 to 60 mol % of the repeating unit of the general formula (4) and 10 to 85 mol % of the repeating unit containing the acid labile group or cross-linking site, preferably 2 to 40 mol % of the repeating unit of the general formula (4) and 10 to 70% of the repeating unit containing the acid labile group or cross-linking site, more preferably 4 to 30 mol % of the repeating unit of the general formula (4) and 15 to 60% of the repeating unit containing the acid labile group or cross-linking site, with the balance being the auxiliary repeating unit. The composition of the sulfonate resin is not however limited to these ranges as mentioned above.

The sulfonate resin of the present invention generally has a mass-average molecular weight of 1,000 to 1,000,000, preferably 2,000 to 500,000, as measured by gel permeation chromatography (GPC). In the case of using a positive or negative photosensitive film-forming resin in combination, the mass-average molecular weight is generally in the range of 1,000 to 100,000, preferably 2,000 to 50,000. If the mass-average molecular weight is less than 1,000, the effect of use of the resin is low as the resin may diffuse and migrate in a resist film and reach an unexposed portion of the resist film during heat treatment after pattern exposure to thereby cause deterioration of pattern resolution. If the mass-average molecular weight exceeds 1,000,000, the solubility of the resin in the solvent may become lowered so that it is unfavorably difficult to form a smooth resist film. The molecular weight distribution (Mw/Mn) of the resin is preferably in the range of 1.01 to 5.00, more preferably 1.01 to 4.00, still more preferably 1.01 to 3.00, most preferably 1.10 to 2.50.

As mentioned above, the sulfonate resin of the present invention is in the form of the homopolymer or in the form of the copolymer with the other monomer. When the monomer with the acid labile group is used as the other monomer, the sulfonate resin attains photosensitive solubility-changing function for use in the positive resist composition. When the monomer with the cross-linking site is used as the other monomer, the sulfonate resin attains photosensitive solubility-changing function for use in the negative resist composition. The copolymerization monomer used is not limited to the monomer with the acid labile group or cross-linking site. Various kinds of auxiliary monomers can be copolymerized in the sulfonate resin for control of dry etching resistance, standard developer compatibility, substrate adhesion, resist profile and other generally required resist characteristics such as resolution, heat resistance and sensitivity.

The sulfonate resin functioning as the photoacid generator and as the positive or negative resist resin will be explained below. The resin having the repeating unit with positive or negative photosensitive solubility-changing function can be obtained by copolymerization of any monomer having positive or negative photosensitive solubility-changing function with the polymerizable fluorine-containing sulfonic acid onium salt of the general formula (2).

In the case where the sulfonate resin performs photosensitive solubility-changing function as a positive resist resin, a side chain of the sulfonate resin has a leaving site such as carboxyl group or hydroxyl group protected by an acid labile group; and a main chain of the sulfonate resin has a repeating unit formed by cleavage of polymerizable double bond group such as vinyl group, 1-methylvinyl group, 1-fluorovinyl group, 1-trifluoromethylvinyl group, 1-cyanovinyl group or norbornenyl group. The leaving site is bonded to the main chain via a linking group W. The acid labile group refers to a group capable of leaving to serve as an acid by the action of an acid generated from the photoacid generator etc. and thereby increase the dissolution rate of the resin with the acid labile group into alkaline developer. The moiety with such an acid labile group, such as ester moiety (—(C=O)OR$^x$, alkoxycarbonyl) or an ether moiety (—O—R$^x$, alkoxy) (where R$^x$ represents an acid labile group) is called "acid-decomposable site" or "leaving site".

In the case where the sulfonate resin performs photosensitive solubility-changing function as a negative resist resin, a side chain of the sulfonate resin has a cross-linking site such as hydroxyl group or carboxyl group; and a main chain of the sulfonate resin has a repeating unit formed by cleavage of polymerizable double bond group such as vinyl group, 1-methylvinyl group, 1-fluorovinyl group, 1-trifluoromethylvinyl group, 1-cyanovinyl group or norbornenyl group. The cross-linking site is bonded to the main chain via a linking group W. Herein, the hydroxyl group refers to a substantially neutral alcoholic hydroxyl group that is not generally involved in the dissolution of the resin into alkaline solution but is cross-linked with the after-mentioned linking group W by ester bonding, ether bonding, ureide bonding etc. to make the alkali-soluble resin component insoluble in alkali solution.

[Linking Group W]

The linking group W, through which the leaving site of the positive resist resin or the cross-linking site of the negative resist resin is linked to the main chain of the resin, is a divalent linking group formed of one, or any combination of two or more, selected from the group consisting of a single bond, —(CR$^{21}$R$^{22}$)$_n$— (where n represents an integer of 1 to 10), —O—, —C(=O)—, —C(=O)O— or —O—C(=O)—, a divalent alicyclic hydrocarbon, a divalent aromatic hydrocarbon, a thioether, an ester, an amide, a sulfone amide, an urethane and an urea.

Examples of the combination linking group W are —(CR$^{21}$R$^{22}$)$_m$—C(=O)—O—(CR$^{21}$R$^{22}$)$_n$—, —(CR$^{21}$R$^{22}$)$_m$—C(=O)—O—(CR$^{21}$R$^{22}$)$_n$—B—(CR$^{21}$R$^{22}$)$_l$—, —(CR$^{21}$R$^{22}$)$_m$—O—(CR$^{21}$R$^{22}$)$_n$—, —(CR$^{21}$R$^{22}$)$_m$—O—(CR$^{21}$R$^{22}$)$_n$—B—(CR$^{21}$R$^{22}$)$_l$—, —(CR$^{21}$R$^{22}$)$_n$—B—(CR$^{21}$R$^{22}$)$_l$—C(=O)—O—(CR$^{21}$R$^{22}$)$_m$— and —(CR$^{21}$R$^{22}$)$_n$—B—(CR$^{21}$R$^{22}$)$_l$—O—(CR$^{21}$R$^{22}$)$_m$— where B represents a cyclic group selected from divalent alicyclic and aromatic hydrocarbon groups, i.e., a group obtained by elimination of one hydrogen atom from any of the aryl and alicyclic hydrocarbon groups explained above for the linking group W; l, m and n each independently represent an integer of 0 to 10. It is preferable that: m is 0; and l and n are 1.

There is no particular limitation on the monovalent organic groups R$^{21}$ and R$^{22}$ in the substituted methylene group. Each of R$^{21}$ and R$^{22}$ can be a hydrogen atom, a hydroxyl group, or a C$_1$-C$_{30}$ monovalent organic group selected from the group consisting of an alkyl group, an alicyclic hydrocarbon group, a substituted alkyl group, an alkoxy group, an aryl group and a condensed-ring aromatic group. These monovalent organic groups may contain a fluorine atom, an oxygen atom, a sulfur atom, a nitrogen atom or a carbon-carbon double bond. Herein, R$^{21}$ and R$^{22}$ may be the same or different; plural R$^{21}$ may be the same or different; and plural R$^{22}$ may be the same or different. Further, R$^{21}$ and R$^{22}$ may be bonded to each other to form a ring structure, preferably an alicyclic hydrocarbon structure.

The alkyl group has a carbon number of 1 to 30, preferably 1 to 12. Examples of the alkyl group are methyl, ethyl, n-propyl, isopropyl, n-butyl, 1-methylpropyl, 2-methylpropyl, tert-butyl, n-pentyl, i-pentyl, 1,1-dimethylpropyl, 1-methylbutyl, 1,1-dimethylbutyl, n-hexyl, n-heptyl, i-hexyl, n-octyl, i-octyl, 2-ethylhexyl, n-nonyl, n-decyl, n-undecyl and n-dodecyl. Among others, lower alkyl groups are preferred. Particularly preferred are methyl, ethyl, n-propyl, i-propyl and the like.

The substituted alkyl group refers to an alkyl group of which one or two or more hydrogen atoms are substituted with a substituent group such as a C$_1$-C$_4$ alkoxy group, a halogen atom, an acyl group, an acyloxy group, cyano group, hydroxyl group, carboxy group, an alkoxycarbonyl group or a nitro group, preferably a fluorine atom. Examples of the substituted alkyl group are lower fluoroalkyl groups such as trifluoromethyl, pentafluoroethyl, 2,2,2-trifluoroethyl, n-heptafluoropropyl, 2,2,3,3,3-pentafluoropropyl, 3,3,3-trifluoropropyl and hexafluoroisopropyl.

The alkoxy group preferably has a carbon number of 1 to 4. Examples of the alkoxy group are methoxy, ethoxy, propoxy and butoxy.

The aryl group has a carbon number of 1 to 30 and, when it is monocyclic, preferably has a 3- to 12-membered ring, more preferably 3- to 6-membered ring. Examples of the aryl group are phenyl, biphenyl, terphenyl, o-tolyl, m-tolyl, p-tolyl, p-hydroxyphenyl, p-methoxyphenyl, mesityl, o-cumenyl, 2,3-xylyl, 2,4-xylyl, 2,5-xylyl, 2,6-xylyl, 3,4-xylyl, 3,5-xylyl, o-fluorophenyl, m-fluorophenyl, p-fluorophenyl, o-trifluoromethylphenyl, m-trifluoromethylphenyl, p-trifluoromethylphenyl, 2,3-bistrifluoromethylphenyl, 2,4-bistrifluoromethylphenyl, 2,5-bistrifluoromethylphenyl, 2,6-bistrifluoromethylphenyl, 3,4-bistrifluoromethylphenyl, 3,5-bistrifluoromethylphenyl, p-chlorophenyl, p-bromophenyl and p-iodophenyl.

Examples of the C$_1$-C$_{30}$ condensed-ring aromatic group are monovalent organic groups, each obtained by eliminating one hydrogen atom from pentalene, indene, naphthalene, azulene, heptalene, biphenylene, indacene, acenaphthylene, fluororene, phenalene, phenanthrene, anthracene, fluoranthene, acephenanthrylene, aceanthrylene, triphenylene, pyrene, chrysene, naphthacene, picene, perylene, pentaphene, pentacene, tetraphenylene, hexaphene, hexacene, rubicene, coronene, trinaphthylene, heptaphene, heptacene, pyranthrene, ovalene or the like. One or two or more hydrogen atoms of the condensed-ring aromatic group may preferably be substituted with a fluorine atom or a C$_1$-C$_4$ alkyl or fluoroalkyl substituent group.

There can also be used monocyclic or polycyclic heterocyclic groups having 3 to 25 ring atoms, such as pyridyl, furil, thienyl, pyranyl, pyrrolyl, thianthrenyl, pyrazolyl, isothiazolyl, isoxazolyl, pyrazinyl, pyrimidinyl, pyridazinyl, tetrahydropyranyl, tetrahydrofuranyl, tetrahydrothiopyranyl, tetrahydrothiofuranyl and 3-tetrahydrothiophene-1,1-dioxide. One or two or more hydrogen atoms on the ring atoms of the heterocyclic group may be substituted with an alkyl, alicyclic hydrocarbon, aryl or heterocyclic group. Among others, preferred are those having a monocyclic or polycyclic ether ring or a lactone ring as exemplified below.

[Chem. 53]

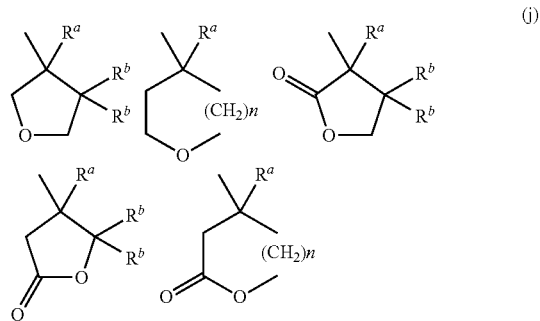

(j)

In the general formula (j), R$^a$ and R$^b$ each independently represent a hydrogen atom or a C$_1$-C$_4$ alkyl group; and n represents an integer of 2 to 4.

The alicyclic hydrocarbon group as R$^{21}$, R$^{22}$ of the linking group W or the alicyclic hydrocarbon group formed by R$^{21}$ and R$^{22}$ together with the carbon atoms bonded thereto may be monocyclic or polycyclic. Examples of such an alicyclic hydrocarbon group are those having a carbon number of 3 or more and having a monocyclo, bicyclo, tricycle or tetracyclo structure. The carbon number of the alicyclic hydrocarbon group is preferably 3 to 30, more preferably 3 to 25. The alicyclic hydrocarbon group may have a substituent.

As the monocyclic hydrocarbon group, there can preferably be used those having a 3- to 12-membered ring, more preferably 3- to 7-membered ring. Examples of such a monocyclic hydrocarbon group are cyclopropyl, cyclobutyl, cyclopentyl, cyclohexyl, cycloheptyl, cyclooctyl, cyclodecanyl, cyclododecanyl, and 4-tert-butylcyclohexyl. As the polycyclic hydrocarbon group, there can preferably be used those having a 7- to 15-membered ring. Examples of such a polycyclic hydrocarbon group are adamantyl, noradamantyl, decalin residue, tricyclodecanyl, tetracyclododecanyl, norbornyl and cedrol. The alicyclic hydrocarbon group can be a spiro ring, preferably having a carbon number of 3 to 6. Preferred examples of the spiro ring are adamantyl, decalin residue, norbornyl, cedrol, cyclohexyl, cycloheptyl, cyclooctyl, cyclodecanyl and tricyclodecanyl. One or two or more hydrogen atoms on the ring carbons of the above organic group, or one or two or more hydrogen atoms of the above linking group, may be each independently substituted with a substituent such as $C_1$-$C_{25}$ alkyl or substituted alkyl group, hydroxyl group, an alkoxy group, carboxyl group or an alkoxycarbonyl group. One or two or more hydrogen atoms of this substituent group may further be substituted with fluorine or trifluoromethyl.

Herein, the alkyl group is preferably a lower alkyl group, more preferably an alkyl group selected from the group consisting of methyl, ethyl, propyl and isopropyl. More preferably, the alkyl group is the one selected from the group consisting of methyl, ethyl, propyl and isopropyl. As the substituent of the substituted alkyl group, there can be used a hydroxyl group, a halogen atom, an alkoxy group and the like. The alkoxy group is, for example, of 1 to 4 carbon atoms, such as methoxy, ethoxy, propoxy or butoxy. Further, the alkoxy carbonyl group is, for example, methoxycarbonyl, ethoxycarbonyl or isopropoxycarbonyl.

More specifically, preferred examples of the linking group W are —O—, —C(=O)—O—, —$CH_2$—O—, —$C_6H_4$—O—, —O—$CH_2$—, —$CH_2$—C(=O)—O—, —C(=O)—O—$CH_2$—, —$CH_2$—O—$CH_2$—, —$CH_2$—C(=O)—O—$CH_2$—, —C(=O)—O—B— (B is a cyclic group), —C(=O)—O—$CR^{21}R^{22}$— and —$C_6H_4$—O—$CR^{21}R^{22}$— where $R^{21}$ and $R^{22}$ are each independently a hydrogen atom, a fluorine atom, an alkyl group, a substituted alkyl group or an alicyclic hydrocarbon group. One or more hydrogen atoms of the above group may be substituted with a fluorine atom. Among others, particularly preferred are —C(=O)—O—$CR^{21}R^{22}$— where $R^{21}$ and $R^{22}$ are each independently either a hydrogen atom or a lower alkyl group, —C(=O)—O— and —$C_6H_4$—O—.

[Acid Labile Group]

The photosensitive solubility-changeable sulfonate resin of the present invention preferably has an acid labile group represented by either of the following general formulas (d) to (h). Among others, the sulfonate resin having an acid labile group of the general formula (d), (e) or (f) functions as chemically amplified type and can be thus particularly preferably used in a resist composition for pattern formation by exposure to high energy radiation such as laser radiation or electron beam radiation.

[Chem. 54]

$R^{16}$—O—C(=O)—     (d)

[Chem. 55]

$R^{16}$—O—$CHR^{17}$—     (e)

[Chem. 56]

$CR^{18}R^{19}R^{20}$—     (f)

[Chem. 57]

$SiR^{18}R^{19}R^{20}$—     (g)

[Chem. 58]

$R^{16}$—C(=O)—     (h)

In the general formulas (d) to (h), $R^{16}$, $R^{17}$, $R^{18}$, $R^{19}$ and $R^{20}$ each independently represent a monovalent organic group. More specifically, $R^{16}$ represents an alkyl group, an alicyclic hydrocarbon group or an aryl group; $R^{17}$ represents a hydrogen atom, an alkyl group, an alicyclic hydrocarbon group, an alkenyl group, an aralkyl group, an alkoxy group or an aryl group; and $R^{18}$, $R^{19}$ and $R^{20}$ may be the same or different and each independently represent an alkyl group, an alicyclic hydrocarbon group, an alkenyl group, an aralkyl group or an aryl group. Two of $R^{18}$, $R^{19}$ and $R^{20}$ may be bonded to each other to form a ring structure.

Preferred examples of the alkyl group are those having a carbon number of 1 to 4, such as methyl, ethyl, propyl, isopropyl, n-butyl, sec-butyl and tert-butyl. Preferred examples of the alicyclic hydrocarbon group are those having a carbon number of 3 to 30, such as cyclopropyl, cyclopentyl, cyclohexyl, adamantyl, norbornyl, boronyl, tricyclodecanyl, dicyclopentenyl, norbornaneepoxy, menthyl, isomenthyl, neomenthyl, tetracyclodecanyl and steroid residue. Preferred examples of the alkenyl group are those having a carbon number of 2 to 4, such as vinyl, propenyl, allyl and butenyl. Preferred examples of the aryl group are those having a carbon number of 6 to 14, such as phenyl, xylyl, toluoyl, cumenyl, naphthyl and anthracenyl. These organic groups may have substituents. Preferred examples of the aralkyl group are those having a carbon number of 7 to 20, such as benzyl, phenethyl and cumyl, each of which may have a substituent.

As the substituents of the above organic groups, there can be used a hydroxyl group, halogen atoms (fluorine, chlorine, bromine, iodine), a nitro group, a cyano group, any of the above-mentioned alkyl and alicyclic hydrocarbon groups, alkoxy groups such as methoxy, ethoxy, hydroxyethoxy, propoxy, hydroxypropoxy, n-butoxy, isobutoxy, sec-butoxy and tert-butoxy, alkoxycarbonyl group such as methoxycarbonyl and ethoxycarbonyl, aralkyl groups such as benzyl, phenethyl and cumyl, aralkyloxy group, acyl groups such as formyl, acetyl, butyryl, benzoyl, cyanamyl or valeryl, acyloxy groups such as butyryloxy, any of the above-mentioned alkenyl groups, alkenyloxy groups such as vinyloxy, propenyloxy, allyloxy and butenyloxy, any of the above-mentioned aryl groups, aryloxy group such as phenoxy, and aryloxycarbonyl groups such as benzoyloxy.

Lactone groups of the following formulas (k-1) and (k-2) are also usable.

[Chem. 59]

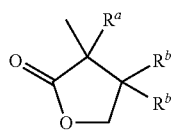 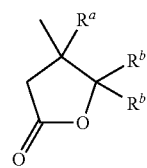

(k-1)

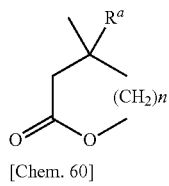

[Chem. 60]

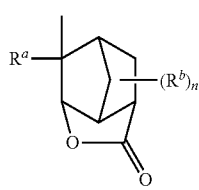

(k-2)

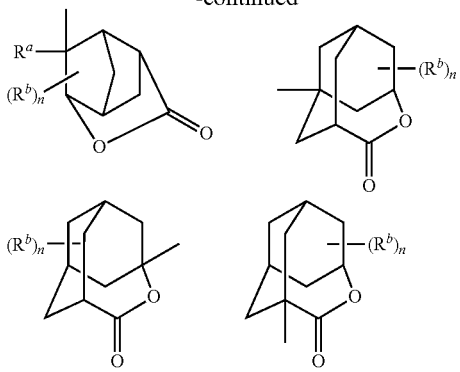

In the formulas (k-1) and (k-2), $R^a$ represents a $C_1$-$C_4$ alkyl or perfluoroalkyl group; $R^b$ each independently represents a hydrogen atom, a $C_1$-$C_4$ alkyl or perfluoroalkyl group, a hydroxyl group, a carboxylic group, an alkyloxycarbonyl group or an alkoxy group; and n represents an integer of 1 to 4.

Specific examples of the alkoxycarbonyl group represented by the general formula (d): $R^{16}$—O—C(=O)— are tert-butoxycarbonyl, tert-amyloxycarbonyl, methoxycarbonyl, ethoxycarbonyl, i-propoxycarbonyl, cyclohexyloxycarbonyl, isobornyloxycarbonyl and adamantaneoxycarbonyl.

Specific examples of the acetal group represented by the general formula (e): $R^{16}$—O—CHR$^{17}$— are methoxymethyl, ethoxymethyl, 1-ethoxyethyl, 1-butoxyethyl, 1-isobutoxyethyl, 1-cyclohexyloxyethyl, 1-benzyloxyethyl, 1-phenethyloxyethyl, 1-ethoxypropyl, 1-benzyloxypropyl, 1-phenethyloxypropyl, 1-ethoxybutyl, 1-cyclohexyoxyethyl, 1-ethoxyisobutyl, 1-methoxyethoxymethyl, tetrahydropyranyl and tetrahydrofuranyl. An acetal group obtained by the addition of a vinyl ether to a hydroxy group is also usable.

Specific examples of the tertiary hydrocarbon group represented by the general formula (f): $CR^{18}R^{19}R^{20}$— are tert-butyl, tert-amyl, 1,1-dimethylpropyl, 1-ethyl-1-methylpropyl, 1,1-dimethylbutyl, 1-ethyl-1-methylbutyl, 1,1-diethylpropyl, 1,1-dimethyl-1-phenylmethyl, 1-methyl-1-ethyl-1-phenylmethyl, 1,1-diethyl-1-phenylmethyl, 1-methylcyclohexyl, 1-ethylcyclohexyl, 1-methylcyclopentyl, 1-ethylcyclopentyl, 1-isoboronyl, 1-methyladamantyl, 1-ethyladamantyl, 1-isopropyladamantyl, 1-isopropylnorbornyl and 1-isopropyl-(4'-methylcyclohexyl).

The alicyclic hydrocarbon group or the alicyclic hydrocarbon-containing acid labile group can be exemplified by the following formulas (I-1) and (1-2).

[Chem. 61]

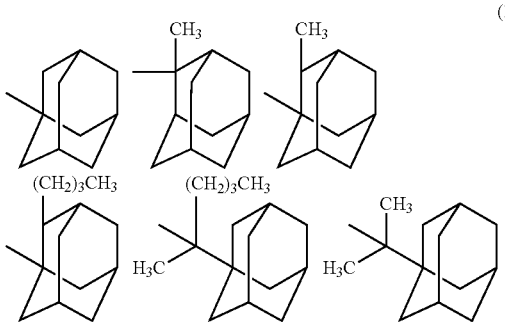
(1-1)

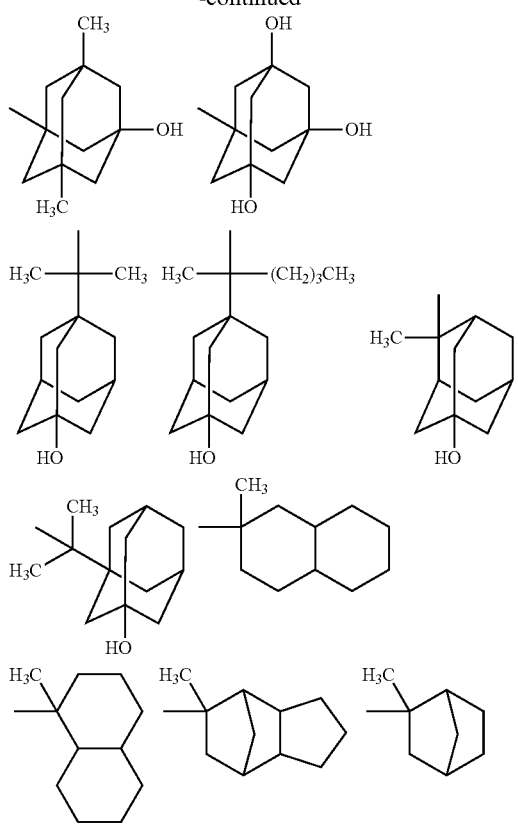

[Chem. 62]

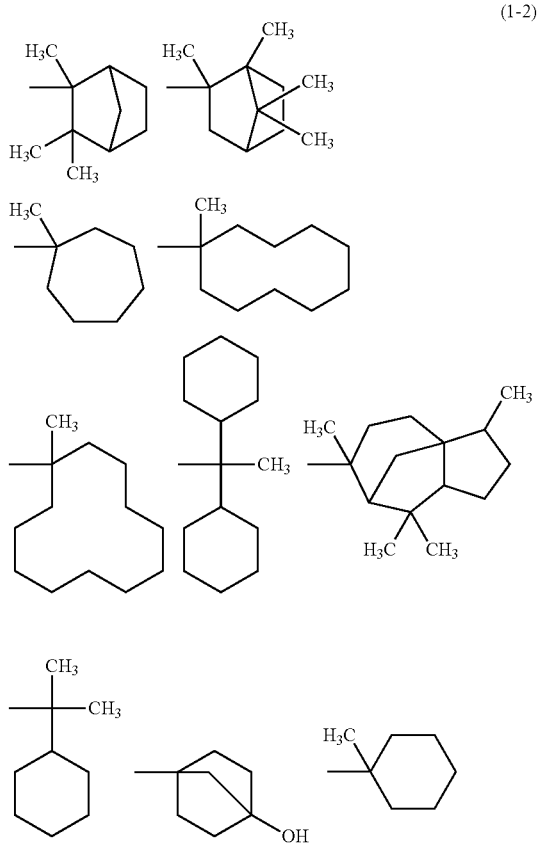
(1-2)

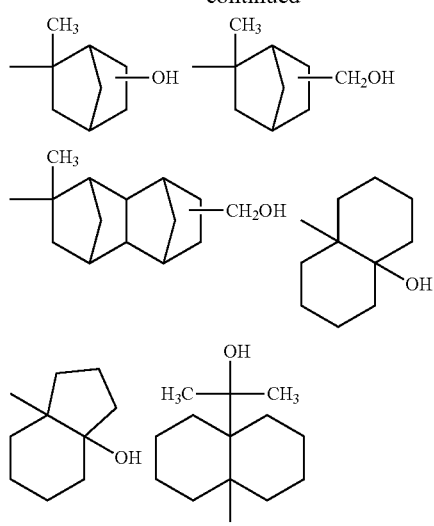

In the formulas (I-1) and (1-2), methyl (CH₃) groups may independently be replaced with ethyl groups; and one or two or more of the ring carbons may have a substituent group as mentioned above.

Specific examples of the silyl group represented by the general formula (g): $SiR^{18}R^{19}R^{20}$— are trimethylsilyl, ethyldimethylsilyl, methyldiethylsilyl, triethylsilyl, i-propyldimethylsilyl, methyl-di-1-propylsilyl, tri-1-propylsilyl, tert-butyldimethylsilyl, methyl-di-tert-butylsilyl, tri-tert-butylsilyl, phenyldimethylsilyl, methyldiphenylsilyl and triphenylsilyl.

Specific examples of the acyl group represented by the general formula (h): $R^{16}$—C(=O)— are acetyl, propionyl, butyryl, heptanoyl, hexanoyl, valeryl, pivaloyl, isovaleryl, lauryloyl, myristoyl, palmitoyl, stearoyl, oxalyl, malonyl, succinyl, glutaryl, adipoyl, piperoyl, suberoyl, azelaoyl, sebacoyl, acryloyl, propioyl, methacryloyl, crotonoyl, oleoyl, maleoyl, fumaroyl, mesaconoyl, camphoroyl, benzoyl, phthaloyl, isophtaloyl, terephthaloyl, naphthoyl, toluoyl, hydratropoyl, atropoyl, cinnamoyl, furoyl, thenoyl, nicotinoyl and isonicotinoyl. A part or all of hydrogen atoms of these acid labile groups can be substituted with fluorine.

The lactone-containing acid labile group can be exemplified by the following formulas (m-1), (m-2) and (m-3).

[Chem. 63]

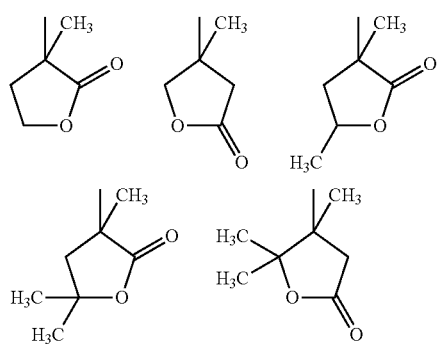
(m-1)

[Chem. 64]

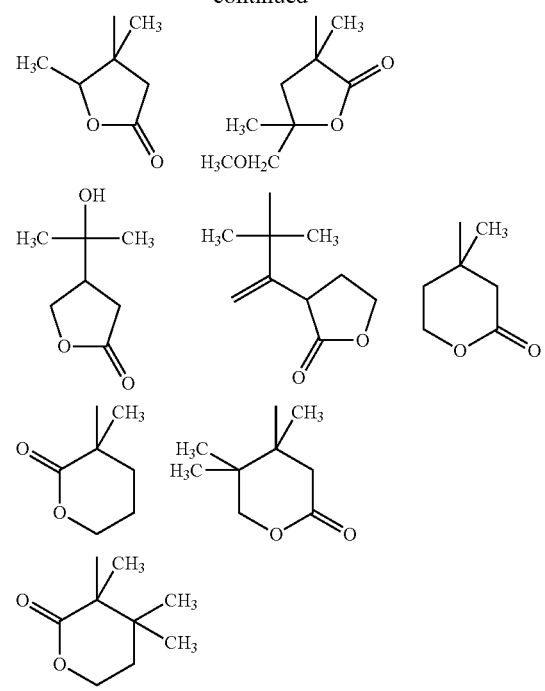
(m-2)

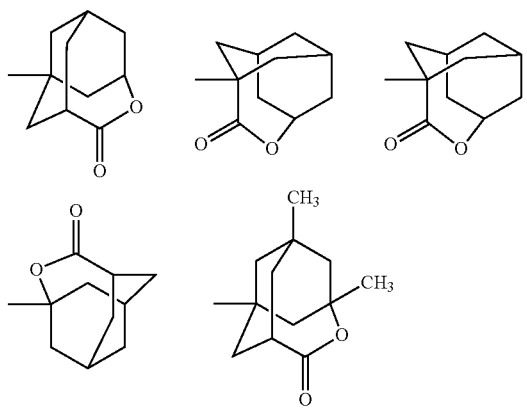

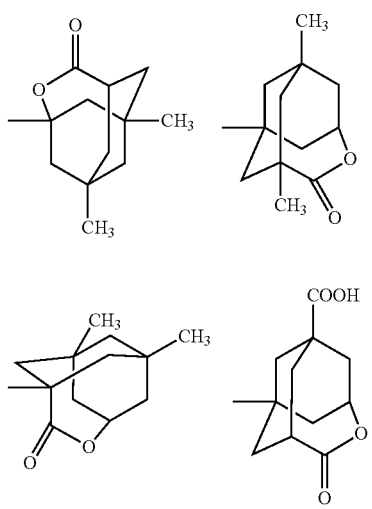

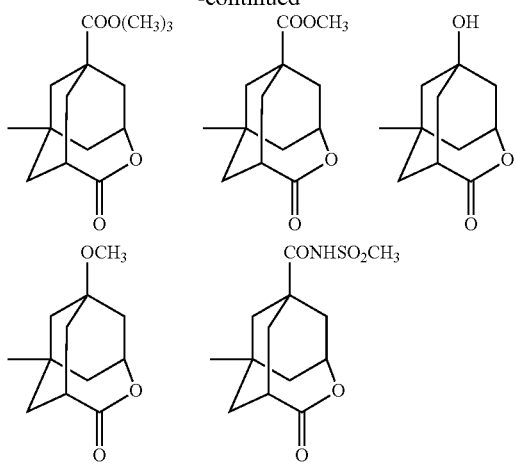

[Chem. 65]

(m-3)

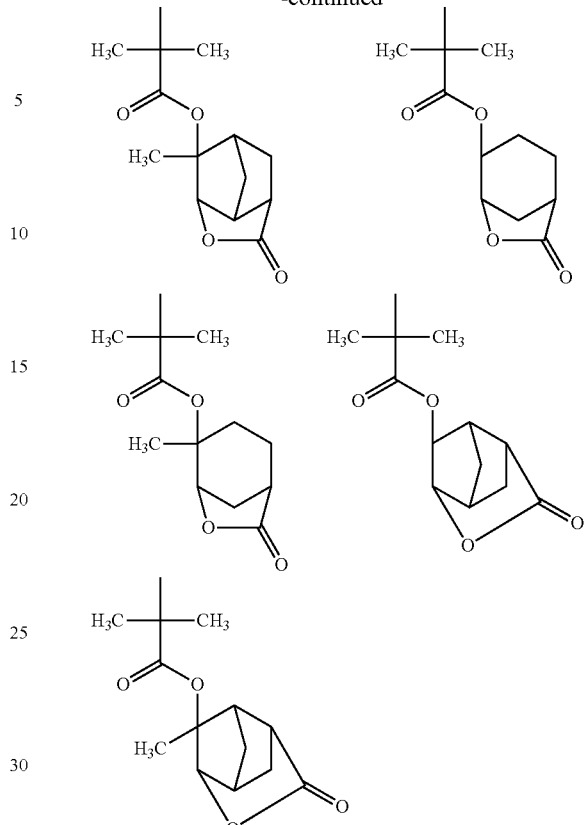

In the formulas (m-1), (m-2) and (m-3), methyl ($CH_3$) groups may independently be replaced with ethyl groups.

In the case of using an ArF excimer laser as an exposure light source, the acid labile group is preferably a tertiary alkyl group such as tert-butyl or tert-amyl, an alkoxyethyl group such as 1-ethoxyethyl, 1-butoxyethyl, 1-isobutoxyethyl or 1-cyclohexyethyl, an alkoxymethyl group such as methoxymethyl or ethoxymethyl, an alicyclic hydrocarbon group such as adamantyl or isoboronyl, or an alicyclic hydrocarbon-containing acid labile group, or a lactone-containing acid labile group.

The photosensitive solubility-changeable sulfonate resin may have another repeating unit introduced by copolymerization with the other copolymerization component as explained below. In this copolymerization composition, the amount of the other copolymerization component is preferably 80 mol % or less, more preferably 60 mol % or less, still more preferably 50 mol % or less. If the amount of the other copolymerization component exceeds 80 mol %, the function of the resin as the photoacid generator becomes lowered so that the resin cannot show sufficient photosensitivity or cannot show sufficient solubility or cross-linking ability even in the case of a normal content ratio between the repeating unit with the acid labile group or cross-linking site and the repeating unit with the sulfonate structure.

[Other Copolymerization Component (Auxiliary Repeating Unit)]

As mentioned above, the sulfonate resin of the present invention may have an auxiliary repeating unit derived from the other copolymerization component (referred to as "auxiliary monomer"). There is no particular limitation on the auxiliary monomer. Examples of the auxiliary monomer are olefins, fluorine-containing olefins, acrylic esters, methacrylic esters, fluorine-containing acrylic esters, fluorine-containing methacrylic esters, norbornene compounds, fluorine-containing norbornene compounds, styrenic compounds, fluorine-containing styrenic compounds, vinyl ethers and fluorine-containing vinyl ethers. These copolymerization components can be used solely or in combination of two or more thereof. Among others, acrylic esters, methacrylic esters, fluorine-containing acrylic esters, fluorine-containing methacrylic esters, norbornene compounds, fluorine-containing norbornene compounds, styrenic compounds, vinyl ethers and fluorine-containing vinyl ethers are preferred.

Specific examples of the olefins are ethylene and propylene. Specific examples of the fluoroolefins are vinyl fluoride, vinylidene fluoride, trifluoroethylene, chlorotrifluoroethylene, tetrafluoroethylene, hexafluoroethylene and hexafluoroisobutene.

There is no particular limitation on the ester side chain structure of the acrylic ester or methacrylic ester. Specific examples of the acrylic esters or methacrylic esters are known acrylic or methacrylic ester compounds: such as acrylic or methacrylic acid alkyl ester e.g. methyl acrylate or methacrylate, ethyl acrylate or methacrylate, n-propyl acrylate or methacrylate, isopropyl acrylate or methacrylate, n-butyl acrylate or methacrylate, isobutyl acrylate or methacrylate, n-hexyl acrylate or methacrylate, n-octyl acrylate or methacrylate, 2-ethylhexyl acrylate or methacrylate, lauryl acrylate or methacrylate, 2-hydroxyethyl acrylate or methacrylate, or 2-hydroxypropyl acrylate or methacrylate; acrylate or methacrylate containing an ethylene glycol group, a propylene glycol group or a tetramethylene glycol group; unsaturated amide e.g. acrylamide, methacrylamide, N-methylol acrylamide, N-methylol methacrylamide, or diacetone acrylamide; acrylonitrile; methacrylonitrile; alkoxysilane-containing vinylsilane or acrylic or methacrylic ester; t-butyl acrylate or methacrylate; 3-oxocyclohexyl acrylate or methacrylate; adamantyl acrylate or methacrylate; alkyladamantyl acrylate or methacrylate; cyclohexyl acrylate or methacrylate; tricyclodecanyl acrylate or methacrylate; acrylate or methacrylate having a ring structure such as a lactone ring or a norbornene ring; acrylic acid; and methacrylic acid. An acrylate compound obtained by bonding a cyano group to the α-position of the above acrylate or an analog thereof, such as maleic acid, fumaric acid or maleic anhydride, is also usable.

Examples of the fluorine-containing acrylic esters or fluorine-containing methacrylic esters are acrylic esters or methacrylic esters each having a fluorine-containing group in the α-position of the acrylic moiety or in the ester moiety thereof. A cyano group may be introduced into the α-position. For example, there can suitably be used, as the monomer having the fluoroalkyl group in the α-position, a monomer in which a trifluoromethyl group, a trifluoroethyl group, a nonafluoro-n-butyl group etc. has been added to the α-position of the above non-fluorinated acrylic ester or methacrylic ester.

On the other hand, there can be used acrylic esters or methacrylic esters in which the ester moiety is a fluorinated alkyl group e.g. a perfluoroalkyl group or a fluoroalkyl group, or in which a cyclic structure and a fluorine atom coexist in the ester moiety. The cyclic structure may be, for example, a fluorine-containing benzene ring, a fluorine-containing cyclopentane ring, a fluorine-containing cyclohexane ring, a fluorine-containing cycloheptane ring or the like, in which a fluorine atom or a trifluoromethyl group has been introduced as a substituent. An acrylic ester or methacrylic ester in which the ester moiety is a fluorine-containing t-butyl ester group is also usable. Typical examples of such monomer units are 2,2,2-trifluoroethyl acrylate, 2,2,3,3-tetrafluoropropyl acrylate, 1,1,1,3,3,3-hexafluoroisopropyl acrylate, heptafluoroisopropyl acrylate, 1,1-dihydroheptafluoro-n-butyl acrylate, 1,1,5-trihydrooctafluoro-n-pentyl acrylate, 1,1,2,2-tetrahydrotridecafluoro-n-octyl acrylate, 1,1,2,2-tetrahydroheptadecafluoro-n-decyl acrylate, 2,2,2-trifluoroethyl methacrylate, 2,2,3,3-tetrafluoropropyl methacrylate, 1,1,1,3,3,3-hexafluoroisopropyl methacrylate, heptafluoroisopropyl methacrylate, 1,1-dihydroheptafluoro-n-butyl methacrylate, 1,1,5-trihydrooctafluoro-n-pentyl methacrylate, 1,1,2,2-tetrahydrotridecafluoro-n-octyl methacrylate, 1,1,2,2-tetrahydroheptadecafluoro-n-decyl methacrylate, perfluorocyclohexylmethyl acrylate and perfluorocyclohexylmethyl methacrylate.

As the norbornene compounds and fluorine-containing norbornene compounds, there can be used, without particular limitation, norbornene monomers each having a mononuclear or multinuclear structure. Among others, suitable examples of the norbornene compounds are those formed by the Diels-Alder addition reaction of an unsaturated compound such as an allyl alcohol, a fluorine-containing allyl alcohol, an acrylic acid, an α-fluoroacrylic acid, a methacrylic acid and any of the acrylic esters, methacrylic esters, fluorine-containing acrylic esters and fluorine-containing methacrylic esters described in the present specification with cyclopentadiene or cyclohexadiene.

The styrenic compounds, fluorine-containing styrenic compounds, vinyl ethers, fluorine-containing vinyl ethers, allyl ethers, vinyl esters, vinyl silanes and the like are also usable. Examples of the styrenic compounds and fluorine-containing styrenic compounds are styrene, fluorinated styrene, hydroxystyrene, hexafluoroacetone-added styrene, styrene or hydroxystyrene in which hydrogen has been substituted with a trifluoromethyl group and monomers each obtained by bonding a halogen, an alkyl group or a fluoroalkyl group to the α-position of the above styrene or styrenic compound. Further, there can be used various vinyl ethers, fluorine-containing vinyl ethers, allyl ethers, vinyl esters and the like. One example of the vinyl ethers is an alkyl vinyl ether that may contain a methyl group, an ethyl group or a hydroxy group such as hydroxyethyl or hydroxybutyl. All or part of hydrogen atoms of the alkyl vinyl ether may be substituted with fluorine. Other examples of the vinyl ethers are cyclohexyl vinyl ether, cyclic vinyl ether containing a hydrogen or carbonyl bond in its cyclic structure and monomers obtained by substituting all or part of hydrogen atoms of the cyclic vinyl ether with fluorine. The allyl ethers, vinyl esters and vinyl silane can be used without particular limitation as long as they are known compounds.

In particular, it is preferable that the sulfonate resin (photosensitive solubility-changeable sulfonate resin) has a repeating unit of the following general formula (6) in addition to the repeating unit of the general formula (4).

[Chem. 66]

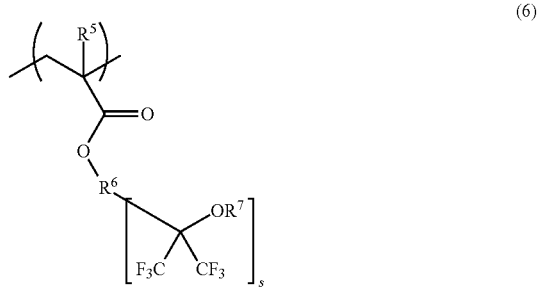

(6)

In the general formula (6), $R^5$ represents a hydrogen atom, a halogen atom, or a $C_1$-$C_3$ alkyl or fluorine-containing alkyl group; $R^6$ represents a straight, branched or cyclic divalent alkylene group, a divalent aromatic group, or a divalent organic moiety in which a plurality of straight, branched or cyclic structure-containing divalent alkylene and/or divalent aromatic groups are bonded to each other, and may be partially fluorinated; $R^7$ represents a hydrogen atom, or a $C_1$-$C_{20}$ straight or branched alkyl, fluorine-containing alkyl or aromatic or alicyclic group which may contain an oxygen atom or a carbonyl bond; and s represents an integer of 1 or 2.

There is no particular limitation on $R^5$ as long as $R^5$ is either a hydrogen atom, a halogen atom, or a $C_1$-$C_3$ alkyl or fluorine-containing alkyl group. Preferred examples of $R^5$ are: halogen atoms such as fluorine, chlorine and bromine; $C_1$-$C_3$ alkyl groups such as methyl, ethyl, propyl and isopropyl; and $C_1$-$C_3$ fluorine-containing alkyl groups each obtained by substituting all or part of hydrogen atoms of the above alkyl group with a halogen atom, such as trifluoromethyl (—$CF_3$), trifluoroethyl (—$CH_2CF_3$), 1,1,1,3,3,3-hexafluoroisopropyl and heptafluoroisopropyl.

There is also no particular limitation on $R^6$ as long as $R^6$ is either a straight, branched or cyclic structure-containing divalent alkylene group, a divalent aromatic group, or a divalent organic moiety in which a plurality of straight, branched or cyclic structure-containing divalent alkylene and/or divalent aromatic groups are bonded to each other. Further, $R^6$ may be partially fluorinated. Preferred examples of $R^6$ are: linear or branched alkylene groups such as methylene, ethylene, isopropylene and t-butylene; cyclobutene; cyclohexane; cyclic structures with divalent norbornene and adamantane groups; and phenyl group.

Preferred examples of the repeating unit of the general formula (6) are those of the following general formulas (7) to (9).

[Chem. 67]

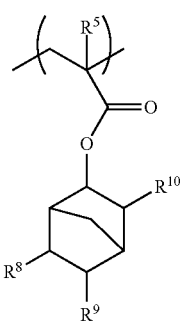

(7)

[Chem. 68]

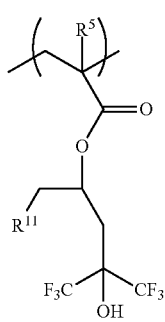

(8)

[Chem. 69]

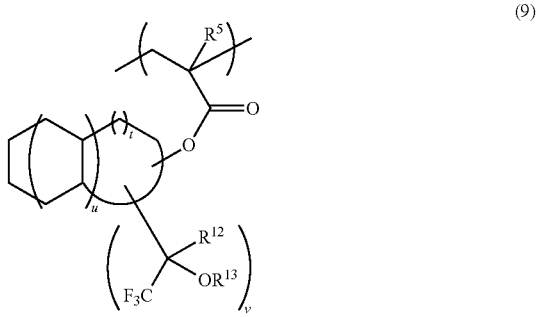

(9)

In the general formula (7), $R^5$ has the same definition as in the general formula (6); either one of $R^8$, $R^9$ and $R^{10}$ represents $CF_3C(CF_3)(OH)CH_2$—; and the other two of $R^8$, $R^9$ and $R^{10}$ each represent a hydrogen atom.

In the general formula (8), $R^5$ has the same definition as in the general formula (6); and $R^{11}$ represents a hydrogen atom, a methyl group, an ethyl group, a n-propyl group, an isopropyl group, a n-butyl group, a sec-butyl group, a tert-butyl group, a fluoromethyl group, a difluoromethyl group, a trifluoromethyl group, or a perfluoroethyl group.

In the general formula (9), $R^5$ also has the same definition as in the general formula (6); $R^{12}$ represents a methyl group or a trifluoromethyl group; $R^{13}$ represents a hydrogen atom, or a $C_1$-$C_{25}$ linear or $C_3$-$C_{25}$ branched or cyclic hydrocarbon group or aromatic hydrocarbon group, a part of which may contain a fluorine atom, an oxygen atom or a carbonyl bond; u represents an arbitrary integer of 0 to 2; t and v each independently represent an arbitrary integer of 1 to 8 and satisfy a relationship of $v \le t+2$; and, when there are a plurality of $R^{12}$ and $R^{13}$, they may be the same or different.

Specific examples of the $C_1$-$C_{25}$ linear or $C_3$-$C_{25}$ branched or cyclic hydrocarbon group or aromatic hydrocarbon group as $R^{13}$ are methyl, ethyl, propyl, isopropyl, cyclopropyl, n-propyl, sec-butyl, tert-butyl, n-pentyl, cyclopentyl, sec-pentyl, neopentyl, hexyl, cyclohexyl, ethylhexyl, norbornel, adamantyl, vinyl, aryl, butenyl, pentenyl, ethynyl, phenyl, benzyl and 4-methoxybenzyl, each of which may be partially or fully fluorinated. There can also be used oxygen-containing hydrocarbon groups such as an alkoxycarbonyl group, an acetal group and an acyl group. Examples of the alkoxycarbonyl group are tert-butoxycarbonyl, tert-amyloxycarbonyl, methoxycarbonyl, ethoxycarbonyl and i-propoxycarbonyl. Examples of the acetal group are: linear ethers such as methoxymethyl, methoxyethoxymethyl, ethoxyethyl, butoxyethyl, cyclohexyloxyethyl, benzyloxyethyl, phenethyloxyethyl, ethoxypropyl, benzyloxypropyl, phenethyloxypropyl, ethoxybutyl and ethoxyisobutyl; and cyclic ethers such as tetrahydrofuranyl and tetrahydropyranyl. Examples of the acyl group are acetyl, propionyl, butyryl, heptanoyl, hexanoyl, valeryl, pivaloyl, isovaleryl, lauryloyl, myristoyl, palmitoyl, stearoyl, oxalyl, malonyl, succinyl, glutaryl, adipoyl, piperoyl, suberoyl, azelaoyl, sebacoyl, acryloyl, propioyl, methacryloyl, crotonoyl, oleoyl, maleoyl, fumaroyl, mesaconoyl, camphoroyl, benzoyl, phthaloyl, isophtaloyl, terephthaloyl, naphthoyl, toluoyl, hydratropoyl, atropoyl, cinnamoyl, furoyl, thenoyl, nicotinoyl and isonicotinoyl. All or part of hydrogen atoms of the above substituent groups can be substituted with fluorine.

It is further preferable that the sulfonate resin has a repeating unit of the following general formula (10), rather than the repeating unit of the general formula (6), in addition to the repeating unit of the general formula (4).

[Chem. 70]

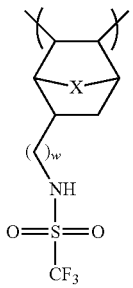

(10)

In the general formula (10), X represents either of —CH$_2$—, —O— and —S—; and w represents an integer of 2 to 6.

It is also preferable that the sulfonate resin has a repeating unit of the following general formula (11), rather than the repeating units of the general formulas (6) and (11), in addition to the repeating unit of the general formula (4).

[Chem. 71]

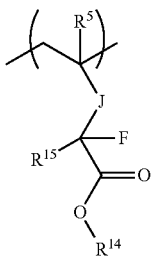

(11)

In the general formula (11), R$^6$ has the same definition as in the general formula (6); R$^{14}$ represents any of the acid labile groups of the general formulas (d) to (h); and R$^{15}$ represents a hydrogen atom, a fluorine atom or a fluorine-containing alkyl group.

There is no particular limitation on the fluorine-containing alkyl group as R$^{15}$. As R$^{15}$, there can be used fluorine-containing alkyl groups having a carbon number of 1 to 12, preferably 1 to 3. Preferred examples of the fluorine-containing alkyl group as R$^{15}$ are trifluoromethyl, pentafluoroethyl, 2,2,2-trifluoroethyl, n-heptafluoropropyl, 2,2,3,3,3-pentafluoropropyl, 3,3,3-trifluoropropyl and hexafluoroisopropyl. Fluorine or trifluoromethyl are particularly preferred as R$^{15}$.

The resin having the repeating unit of the general formula (5), when mixed in a resist composition, exhibits high acidity and thus can be used as a solubility improver to improve the solubility of the positive or negative resist resin composition.

[Polymerization Method]

There is no particular limitation on the polymerization process for production of the resin having the repeating unit of the general formula (4) according to the present invention. The polymerization reaction can be performed by any common polymerization process. It is preferable to adopt radical polymerization process or ionic polymerization process. In some cases, it is feasible to adopt coordination anionic polymerization process, living anionic polymerization process, cationic polymerization process, ring opening metathesis polymerization process, vinylene polymerization process, or vinyl addition process.

The radical polymerization process can be conducted by a known polymerization technique such as bulk polymerization, solution polymerization, suspension polymerization or emulsion polymerization technique in a batch, semi-continuous or continuous operation system in the presence of a radical polymerization initiator or a radical initiating source.

There is no particular limitation on the radical polymerization initiator. As the radical polymerization initiator, there can be used azo compounds, peroxide compounds and redox compounds. Preferred examples of the radical polymerization initiator are azobisbutyronitrile, tert-butylperoxypivalate, di-tert-butyl peroxide, i-butyryl peroxide, lauroyl peroxide, succinic peroxide, dicinnamyl peroxide, di-n-propylperoxydicarbonate, tert-butylperoxyallyl monocarbonate, benzoyl peroxide, hydrogen peroxide and ammonium persulfate.

There is also no particular limitation on the reaction vessel used in the polymerization reaction. Further, the polymerization reaction can be performed by the use of a polymerization solvent. As the polymerization solvent, preferred are those that do not interfere with the radical polymerization process. Typical examples of the polymerization solvent are: ester solvents such as ethyl acetate and n-butyl acetate; ketone solvents such as acetone and methyl isobutyl ketone; hydrocarbon solvents such as toluene and cyclohexane; alcohol solvents such as methanol, isopropyl alcohol and ethylene glycol monomethyl ether. Water, ether solvents, cyclic ether solvents, fluorocarbon solvents and aromatic solvents are also usable. These solvents can be used solely or in combination of two or more thereof. A molecular weight adjusting agent such as mercaptan may be used in combination. The reaction temperature of the copolymerization reaction is set as appropriate depending on the kind of the radical polymerization initiator or radical initiating source and is generally preferably in the range of 20 to 200° C., more preferably 30 to 140° C.

As a technique for removing water or the organic solvent from the obtained fluorine-containing polymer solution or dispersion, reprecipitation, filtration, distillation by heating under a reduced pressure or the like is applicable.

The resin having the repeating unit of the general formula (5) can be produced by the same procedure as the resin having the repeating unit of the general formula (5). Alternately, it is feasible to produce the resin having the repeating unit of the general formula (5) by homopolymerizing or copolymerizing the polymerizable fluorine-containing sulfonate resin of the general formula (3) by the above polymerization process and then hydrolyzing a part or all of the protecting groups of the sulfonic acid moiety of the resulting polymer.

[Resist Composition]

The resin having the repeating unit of the general formula (4) according to the present invention is used as a resist composition in the form of a solution by mixing with other components into a solvent. This resin functions as a photoacid generator. In the case where the resin combines the repeating unit of the general formula (4) with the repeating unit with the acid labile group or cross-linking site, the resin also functions as a chemically amplified resist resin. In the case where the resin has the repeating unit of the general formula (4) but does not have the repeating unit with the acid labile group or cross-linking site, the resist composition contains another resin having a repeating unit with an acid labile group or cross-linking site as an essential component. The base resin may or may not have the repeating unit of the general formula (4). In the case of using the sulfonate resin together with or without such a base resin, the amount of the repeating unit of the general formula (4) is generally in the range of 0.1 to 50 mol %, preferably 0.5 to 30 mol %, more preferably 1 to 15 mol %, based on the amount of all of the repeating units of the sulfonate resin and the base resin. The resist composition using the resin having the repeating unit of the general formula (4) may contain various additives commonly used for resist compositions, such as additive resin, quencher, dissolution inhibitor, plasticizer, a stabilizer, coloring agent, surfactant, viscosity improver, leveling agent, antifoaming agent, compatibilizer, primer and antioxidant, in addition to the solvent. In the case of the negative resist composition, other additives such as a cross-linking agent and a basic compound may further be added. As these additives, there can be used any additive compounds explained below or any other known additive compounds as appropriate.

[Base Resin]

In the present specification, the base resin refers to a resin containing an acid labile group so as to function as a positive resist or a resin containing a cross-linking site so as to function as a negative resist. The above-mentioned photosensitive solubility-changeable sulfonate resin is one example of the base resin.

The chemically amplified resist composition generally contains a base resin, a photoacid generator and a solvent, and optionally an additive or additives such as a basic compound, a dissolution inhibitor and a cross-linking agent as needed.

In the case of the base resin for the positive resist composition, a side chain of the base resin has a leaving site such as carboxyl group or hydroxyl group protected by an acid labile group; and a main chain of the base resin has a repeating unit formed by cleavage of polymerizable double bond group such as acrylic group, methacrylic group, α-trifloromethylacrylic group, vinyl group, allyl group or norbornenyl group.

In the case of the base resin for the negative resist composition, a side chain of the base resin has a cross-linking site such as hydroxyl group or carboxyl group; and a main chain of the base resin has a repeating unit formed by cleavage of polymerizable double bond group such as acrylic group, methacrylic group, α-trifloromethylacrylic group, vinyl group, allyl group or norbornene group.

In many cases, the base resin is copolymer form for control of the resist characteristics. Herein, the above explanations of the copolymerization component, the acid labile group, cross-linking site and linking group can be applied as they are for the base resin. As the copolymerization component, a lactone ring-containing monomer is useful for improvement in the adhesion of the resist to the substrate.

The base resin may have the above-mentioned sulfonate resin repeating unit so as to also function as a photoacid generator. This makes it possible to prepare the positive resist composition from only the base resin with the acid labile group and the solvent or possible to prepare the negative resist composition from only the base resin with the cross-linking site and the solvent. The resist composition may use any known photoacid generator in combination. It is also feasible to use any other additive or additives common in the field of resist compositions.

The base resin generally has a mass-average molecular weight of 1,000 to 1,000,000, preferably 2,000 to 500,000, as measured by gel permeation chromatography (GPC). If the mass-average molecular weight of the base resin is less than 1,000, the resin composition may not form a film with sufficient strength. If the mass-average molecular weight of the base resin exceeds 1,000,000, the solubility of the resin in the solvent may become lowered so that it is unfavorably difficult to form a smooth film of the resin composition. The molecular weight distribution (Mw/Mn) of the base resin is preferably in the range of 1.01 to 5.00, more preferably 1.01 to 4.00, still more preferably 1.01 to 3.00, most preferably 1.10 to 2.50.

In the case of the negative resist composition, there may be used any one selected from known cross-linking agents for chemically amplified negative resist compositions.

More specifically, there can be used, as the cross-linking agent, compounds each formed by reacting an amino group-containing compound such as melamine, acetoguanamine, benzoguanamine, urea, ethylene urea, propylene urea or glycoluril, with either formaldehyde or a mixture of formaldehyde and a lower alcohol to thereby substitute a hydrogen atom of the amino group with a hydroxymethyl group or a lower alkoxymethyl group. Herein, the cross-linking agents using melamine, urea, alkylene urea e.g. ethylene urea, propylene urea etc. and glycoluril are hereinafter referred to as "melamine-based cross-linking agent", "urea-based cross-linking agent", "alkylene urea-based cross-linking agent" and "glycoluril-based cross-linking agent", respectively. The cross-linking agent is preferably at least one selected from the group consisting of melamine-based cross-linking agents, urea-based cross-linking agents, alkylene urea-based cross-linking agents and glycoluril-based cross-linking agents. Particularly preferred are glycoluril-based cross-linking agents.

Examples of the melamine-based cross-linking agents are hexamethoxymethylmelamine, hexaethoxymethylmelamine, hexapropoxymethylmelamine and hexabutoxymethylmelamine. Among others, hexamethoxymethylmelamine is preferred.

Examples of the urea-based cross-linking agents are bismethoxymethylurea, bisethoxymethylurea, bispropoxymethylurea and bisbutoxymethylurea. Among others, bismethoxymethylurea is preferred.

Examples of the alkylene urea-based cross-linking agents are: ethylene urea-based cross-linking agents such as mono- and/or di-hydroxymethylated ethylene urea, mono- and/or di-methoxymethylated ethylene urea, mono- and/or di-ethoxymethylated ethylene urea, mono- and/or di-propoxymethylated ethylene urea and mono- and/or di-butoxymethylated ethylene urea; propylene urea-based cross-linking agents such as mono- and/or di-hydroxymethylated propylene urea, mono- and/or di-methoxymethylated propylene urea, mono- and/or di-ethoxymethylated propylene urea, mono- and/or di-propoxymethylated propylene urea and mono- and/or di-butoxymethylated propylene urea; and 1,3-di(methoxymethyl)-4,5-dihydroxy-2-imidazolidinone and 1,3-di(methoxymethyl)-4,5-dimethoxy-2-imidazolidinone.

Examples of the glycoluril-based cross-linking agents are mono-, di-, tri- and/or tetra-hydroxymethylated glycoluril, mono-, di-, tri- and/or tetra-methoxymethylated glycoluril, mono-, di-, tri- and/or tetra-ethoxymethylated glycoluril, mono-, di-, tri- and/or tetra-propoxymethylated glycoluril and mono-, di-, tri- and/or tetra-butoxymethylated glycoluril.

These cross-linking agents can be used solely or in combination of two or more thereof. In the present invention, the total amount of the cross-linking agent in the negative resist composition is preferably 3 to 30 parts by mass, more preferably 3 to 25 parts by mass, most preferably 5 to 20 parts by mass, per 100 parts by mass of the base resin. When the total amount of the cross-linking agent is not less than the above lower limit, it is possible to obtain a good resist pattern by sufficient cross-linking. It is possible to attain good resist solution storage stability and prevent deterioration in sensitivity with time when the total amount of the cross-linking agent is not larger than the above upper limit.

[Basic Compound]

The basic compound is preferably contained as an optional component in the resist composition of the present invention so as to function as a quencher or to obtain improvements in resist pattern shape and post exposure stability.

There can be used any known basic compounds such as primary, secondary and tertiary aliphatic amines, aromatic amines, heterocyclic amines, nitrogen-containing compounds with a hydroxyphenyl group, alcoholic nitrogen-containing compounds and amide derivatives. Among others, secondary and tertiary apliphatic amines, aromatic amines and heterocyclic amines are preferred.

More specifically, the aliphatic amines includes alkylamines or alkylalcoholamines each formed by replacing at least one hydrogen of ammonia ($NH_3$) with a $C_1$-$C_{12}$ alkyl or hydroxyalkyl groups. Examples of such aliphatic amines are: monoalkylamines such as n-hexylamine, n-heptylamine, n-octylamine, n-nonylamine and n-decylamine; dialkylamines such as diethylamine, di-n-propylamine, di-n-heptylamine, di-n-octylamine and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine and tri-n-dodecylamine; and alkylalcoholamines such as diethanolamine, triethanolamine, diisopropanolamine, triisopropanolamine, di-n-octanolamine and tri-n-octanolamine. Above all, alkylacoholamines and trialkylamines are preferred. More preferred are alkylalcoholamines. Among the alkylalcoholamines, triethanolamine and triisopropanolamine are particularly preferred.

Other examples of the basic compound are: aromatic or heterocyclic amines including aniline, aniline derivatives such as N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline and N,N-dimethyltoluidine, heterocyclic amines such as 1,5-diazabicyclo[4.3.0]nona-5-ene, 1,8-diazabicyclo[5.4.0]undeca-7-ene, 1,4-diazabicyclo[2.2.2]octane, 4-dimethylaminopyridine, hexamethylenetetramine and 4,4-dimethylimidazoline, and hindered amines such as bis(1,2,2,6,6-pentamethyl-4-piperidyesebacate; and alcoholic nitrogen-containing compounds such as 2-hydroxypyridine, aminocresol, 2,4-quinolinediole, 3-indole methanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, and 1-[2-(2-hydroxyethoxy)ethyl]piperazine. These compounds can be used solely or in combination of two or more thereof. The amount of the basic compound used is generally 0.01 to 5 parts by mass per 100 parts by mass of the base resin.

In the case of the negative resist resin, an organic carboxylic acid or a phosphorus oxo acid or derivative thereof may be added an optional component in order to prevent sensitivity deterioration caused by the addition of the basic compound and to obtain improvements in resist pattern shape and post exposure stability. These compounds can be used solely or in combination with the basic compound. Suitable examples of the organic carboxylic acid are malonic acid, citric acid, malic acid, succinic acid, benzoic acid and salicylic acid. Suitable examples of the phosphorus oxo acid or its derivative are: phosphoric acids or derivatives thereof, such as phosphoric acid, di-n-butyl phosphate and diphenyl phosphate; phosphonic acids or derivatives thereof, such as phosphonic acid, dimethyl phosphonate, di-n-butyl phosphonate, phenylphosphonic acid, diphenyl phosphonate and dibenzyl phosphonate; and phosphinic acids or derivatives thereof, such as phosphinic acid and phenylphosphinic acid. Of these, phosphonic acid is particularly preferred.

[Solvent]

There is no particular limitation on the solvent as long as the fluorine-containing resin can be dissolved in the solvent. Various organic solvents are usable. Examples of the organic solvent are: ketones such as acetone, methyl ethyl ketone, cyclohexanone, methyl isoamyl ketone and 2-heptanone; polyhydric alcohols and derivatives thereof, such as monomethyl ether, monoethyl ether, monopropyl ether, monobutyl ether or monophenyl ether of ethylene glycol, ethylene glycol monoacetate, diethylene glycol, diethylene glycol monoacetate, propylene glycol, propylene glycol monoacetate, dipropylene glycol or dipropylene glycol monoacetate; cyclic ethers such as dioxane; esters such as methyl lactate, ethyl lactate, methyl acetate, ethyl acetate, butyl acetate, methyl pyruvate, ethyl pyruvate, methyl methoxypropionate and ethyl ethoxypropionate; aromatic solvents such as xylene and toluene; and fluorinated solvents such as fluorocarbon, hydrofluorocarbon, perfluoro compound and hexafluoroisopropyl alcohol. There can also be used a high-boiling-point weak solvent such as turpentine-based petroleum naphtha solvent or paraffin solvent for improvement in ease of application. These solvents can be used solely or in combination of two or more thereof.

[Surfactant]

The surfactant, preferably a fluorine- and/or silicon-based surfactant, i.e., ether one or two or more of fluorine-based surfactants, silicon-based surfactants and surfactant containing both of fluorine and silicon atoms, is contained in the resist composition of the present invention. In particular, the addition of such a surfactant into the resist composition is effective for use with an exposure light source of 250 nm or less wavelength, notably 200 nm or less wavelength and for pattern formation with a narrower pattern line width. It is possible to attain good sensitivity and resolution and enable resist patterning with less adhesion and development failures.

[Acid Generator]

In the resist composition of the present invention, any known photoacid generator may be used in combination with the sulfonate resin. As the photoacid generator, there can be used any one selected from photoacid generators for chemically amplified resist compositions. Examples of the photoacid generator are bissulfonyldiazomethanes, nitrobenzyl derivatives, onium salts, halogen-containing triazine compounds, cyano-containing oximesulfonate compounds and other oximesulfonate compounds. These photoacid generators can be used solely or in combination of two or more thereof. The amount of the photoacid generator added with the sulfonate resin is generally in the range of 0.5 to 20 parts by mass per 100 parts by mass of the resist composition. If the amount of the photoacid generator added with the sulfonate resin is less than 0.5 parts by mass, the resin composition unfavorably results in insufficient pattern formation. If the amount of the photoacid generator added with the sulfonate resin exceeds 20 parts by mass, the resin composition unfavorably tends to become low in storage stability. The amount of the sulfonate resin of the present invention is generally in the range of 1 to 100 parts by mass, preferably 10 to 100 parts by mass, more preferably 30 to 100 parts by mass, per 100 parts by mass of the total photoacid generator content.

[Additive Resin]

There is no particular limitation on the additive resin as long as the additive resin is soluble in the solvent used and is compatible with the other components of the resist composition. The additive resin functions as a plasticizer, stabilizer, viscosity improver, leveling agent, antifoaming agent, compatibilizer, primer etc.

[Pattern Forming Method]

The resist composition of the present invention can be applied for resist pattern formation by any conventional photoresist technique. Namely, the solution of the resist composition is first applied to a substrate such as silicon wafer by e.g. a spinner and dried to form a photosensitive film of the resist composition. The photosensitive film is irradiated with high energy radiation or electron beam by e.g. an exposure device through a desired mask pattern, and then, subjected to heating. Subsequently, the photosensitive film is developed with an alkaline developer such as 0.1 to 1 mass % tetramethylammoniumhydroxide solution. It is possible by the above method to form a resist pattern according to the mask pattern. As mentioned above, various miscible additives, such as additional resin, quencher, plasticizer, stabilizer, coloring agent, surfactant, viscosity improver, leveling agent, antifoaming agent, compatibilizer, primer and antioxidant, may be added to the resist material as desired.

There is no particular limitation on the high energy radiation used for the pattern formation method of the present invention. In the case of fine processing, it is particularly effective to use high energy radiation of 300 nm or less wavelength, such as near-ultraviolet radiation (wavelength: 380 to 200 nm) or vacuum-ultraviolet radiation (far-ultraviolet radiation, VUV, wavelength: 200 to 10 nm) produced by KrF excimer laser radiation, ArF excimer laser radiation etc., far-ultraviolet radiation (EUV, wavelength: 10 nm or less), soft X-ray, X-ray or γ-ray produced by synchrotron radiation, or electron beam. As the exposure device, there can suitably be used those having a generation source of the high energy radiation of 300 nm or less wavelength or electron beam. The resist composition of the present invention can also suitably be applied to a liquid immersion exposure device, which uses a medium causing less absorption of high energy radiation used and enables more efficient fine processing in terms of numerical aperture and effective wavelength.

EXAMPLES

The present invention will be described in more detail below by way of the following examples. It should be noted that these examples are illustrative and are not intended to limit the present invention thereto.

First, two kinds of polymerizable monomers were prepared by the following procedures.

Preparation Example 1-1

Preparation of Methacryloyloxyacetyl Chloride

[Chem. 72]

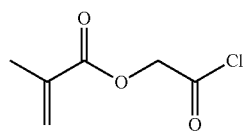

Into a 100-mL reaction vessel with a condenser were added 30 g (purity: 46%, 95.1 mmol) of methacryloyloxyacetic acid (prepared in a method described in International Publication No. 96/41841 and the like), 347 mg (4.8 mmol/0.05 eq) of dimethylformamide and 47.6 g (380.5 mmol/4.0 eq) of thionyl chloride. The resulting solution was stirred at 70° C. for 1 hour and subjected to distillation purification, thereby obtaining 10.0 g of target methacryloyloxyacetyl chloride. The purity of the target product was 70%; and the yield of the target product was 45%.

Properties of Methacryloyloxyacetyl Chloride $^1$H NMR (measurement solvent: deuterium chloroform, reference material: tetramethylsilane) δ=6.22 (s, 1H), 5.70 (s, 1H), 4.96 (s, 2H; $CH_2$), 1.97 (s, 3H; $CH_3$).

Preparation Example 1-2

Preparation of 2-Bromo-2,2-difluoroethyl Pivalate

[Chem. 73]

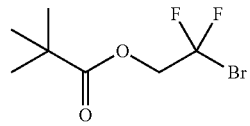

In a glass flask with a thermometer, a condenser and a dropping funnel, 271 g (2.24 mol) of pivaloyl chloride, 360 g (2.23 mol) of 2-bromo-2,2-difluoroethanol and 1.5 L of diisopropyl ether were placed. The resulting solution was stirred, followed by dropping 318 g (3.14 mol) of triethylamine to the stirred solution while cooling the flask in an ice bath. After the dropping, the solution was kept stirred for 1 hour at room temperature. The completion of the reaction was then confirmed by gas chromatography of the solution. The reaction solution was admixed with and totally dissolved in 300 ml of water. After that, 500 ml of 2N hydrochloric acid was added to the solution. The thus-obtained solution was separated into an organic phase and an aqueous phase. The aqueous phase was extracted with 500 ml of diisopropyl ether. The extract was combined with the organic phase. The resulting organic phase was washed with 500 ml of saturated sodium chloride solution, dried with anhydrous sodium sulfate, and then, subjected to solvent evaporation. With this, 85 g of 2-bromo-2,2-difluoroethyl pivalate was obtained as a light yellow liquid (yield: 82%, purity: 93%).

Properties of 2-bromo-2,2-difluoroethyl pivalate $^1$H NMR (measurement solvent: deuterium chloroform, reference material: tetramethylsilane) δ=4.52 (t, 2H), 1.19 (s, 9H).

$^{19}$F NMR (measurement solvent: deuterium chloroform, reference material: trichlorofluoromethane) δ=−56.6 (t, 2F).

Preparation Example 1-3

Preparation of Triethylammonium 1,1-Difluoro-2-(pivaloyloxy)ethanesulfinate

[Chem. 74]

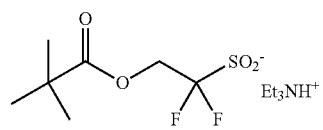

Into a 1-L container, 96.8 g (purity: 93%, 367.2 mmol) of 2-bromo-2,2-difluoroethyl pivalate obtained in Preparation Example 1-2, 200 g of acetonitrile, 250 g of water, 95.8 g (550.8 mmol/1.5 eq) of sodium dithionite and 83.0 g (550.8 mmol/1.5 eq) of triethylamine were subsequently added. The resulting solution was stirred for 2 hours at room temperature. The reaction solution was then separated into an organic phase and an aqueous phase. The organic phase was subjected to evaporation of acetonitrile and converted to a dichloromethane solution by the addition of 100 ml of dichloromethane. The aqueous phase was extracted with 50 mL of dichloromethane. The extract was combined with the organic phase. The resulting organic phase was washed with 10% sodium thiosulfate, water and a sodium chloride solution, and then, subjected to evaporation of dichloromethane. With this, 111.4 g of triethylammonium 1,1-difluoro-2-(pivaloyloxy)ethanesulfinate was obtained with a yield of 76% and a purity of 83%.

Properties of triethylammonium 1,1-difluoro-2-(pivaloyloxy)ethanesulfinate $^1$H NMR (measurement solvent: deuterium chloroform, reference material: tetramethylsilane) δ=4.43 (t, 2H), 3.04 (q, 6H), 1.17 (t, 9H), 1.11 (s, 9H).
$^{19}$F NMR (measurement solvent: deuterium chloroform, reference material: trichlorofluoromethane) δ=–120.3 (t, 3F).

Preparation Example 1-4

Preparation of Triethylammonium 1,1-Difluoro-2-(pivaloyloxy)ethanesulfonate

[Chem. 75]

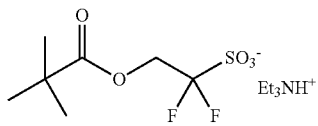

In a 500-mL container were added 111.4 g (purity: 83%, 279.1 mmol) of triethylammonium 1,1-difluoro-2-(pivaloyloxy)ethanesulfinate obtained in Preparation Example 1-3, 100 mL of water and 40.0 g (334.9 mmol/1.2 eq) of 30% hydrogen peroxide solution. The resulting solution was stirred for 3 hours at room temperature. It was confirmed by $^{19}$F NMR of the reaction solution that: the whole of the 1,1-difluoro-2-(pivaloyloxy)ethanesulfinate had been consumed; and there occurred less than 1% of 2-bromo-2,2-difluoroethyl pivalate as a by-product. The reaction solution was extracted twice with 200 mL of dichloromethane. The extracted organic phase was subjected solvent evaporation. The thus-obtained solid was dried and dissolved in methanol, followed by filtering insoluble matter out of the solution. The resulting methanol solution was dropped into isopropyl ether, followed by stirring the solution for 1 hour at room temperature and precipitating a solid out of the solution. The precipitated solid was filtered and dried. With this, 86.8 g of triethylammonium 1,1-difluoro-2-(pivaloyloxy)ethanesulfonate was obtained with a yield of 85% and a purity of 95%.

Properties of triethylammonium 1,1-difluoro-2-(pivaloyloxy)ethanesulfonate $^1$H NMR (measurement solvent: deuterium dimethyl sulfoxide, reference material: tetramethylsilane) δ=4.52 (t, 2H), 3.06 (q, 6H), 1.18 (t, 9H), 1.14 (s, 9H).
$^{19}$F NMR (measurement solvent: deuterium chloroform, reference material: trichlorofluoromethane) δ –113.9 (t, 3F).

Preparation Example 1-5

Preparation of Sodium 2-Hydroxy-1,1-difluoroethanesulfonate

[Chem. 76]

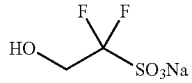

Into a 2-L reaction vessel were added 146.3 g (purity: 95%, 0.40 mol) of triethylammonium 1,1-difluoro-2-(pivaloyloxy)ethanesulfonate obtained in Preparation Example 1-4, 500 mL of water and 100 g (1.2 mol/3 eq) of 48% sodium hydroxide solution. The resulting solution was stirred for 2 hours at room temperature, followed by adding 150 g (1.52 mol/3.8 eq) of 37% aqueous hydrochloric acid solution to the solution. The solution was further stirred for 1 hour at room temperature. The thus-obtained reaction solution was washed twice with 250 mL of diisopropyl ether. The resulting aqueous phase was subjected to solvent evaporation, thereby obtaining 72.2 g of target sodium 2-hydroxy-1,1-difluoroethanesulfonate. The purity of the target product was 71%; and the yield of the target product was 98%.

Properties of sodium 2-hydroxy-1,1-difluoroethanesulfonate $^1$H NMR (measurement solvent: deuterium dimethyl sulfoxide, reference material: tetramethylsilane) δ=3.80 (t, J=16.0 Hz, 2H; CH$_2$).
$^{19}$F NMR (measurement solvent: deuterium dimethyl sulfoxide, reference material: trichlorofluoromethane) δ=–115.34 (t, J=16.0 Hz, 2F; CFA Preparation Example 2-1

Preparation of Sodium 2-[(Methacryloyloxy)acetoxy]-1,1-difluoroethanesulfonate

[Chem. 77]

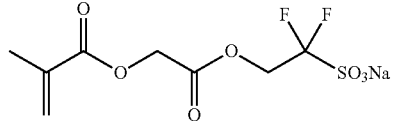

Into a 100-mL reaction vessel, sodium 2-hydroxy-1,1-difluoroethanesulfonate (purity: 91%, 41.4 mmol) obtained in Preparation Example 1-5, 30 g of acetonitrile, 126 mg (1.04 mmol/0.03 eq) of 4-dimethylaminopyridine and 4.89 g (48.3 mmol/1.4 eq) of triethylamine were added. The reaction vessel was cooled in an ice bath, followed by adding thereinto 8.5 g (purity: 70%, 34.5 mmol) of methacryloyloxyacetyl chloride obtained in Preparation Example 1-1. The resulting solution was stirred for 17 hours at room temperature. After that, 1.75 g (17.3 mmol/0.5 eq) of triethylamine was added into the solution. The solution was further stirred for 3 hours. It was confirmed by $^{19}$F NMR of the reaction solution that the reaction had been completed. The reaction solution was admixed with 100 mL of acetone and subjected to filtration and solvent evaporation, thereby obtaining 21.4 g of target sodium 2-[(methacryloyloxy)acetoxy]-1,1-difluoroethanesulfonate. The purity of the target product was 51%; and the yield of the target product was 97%.

Properties of sodium 2-[(methacryloyloxy)acetoxy]-1,1-difluoroethanesulfonate $^{1}$H NMR (measurement solvent: deuterium dimethyl sulfoxide, reference material: tetramethylsilane) δ=6.12 (s, 1H), 5.78 (s, 1H), 4.84 (s, 2H), 4.59 (t, J=16.0 Hz, 2H), 1.91 (s, 3H).
$^{19}$F NMR (measurement solvent: deuterium dimethyl sulfoxide, reference material: trichlorofluoromethane) δ=−113.8 (t, J=16.0 Hz, 2F).

Preparation Example 2-2

Preparation of Triphenylsulfonium 2-[(Methacryloyloxy)acetoxy]-1,1-difluoroethanesulfonate

[Chem. 78]

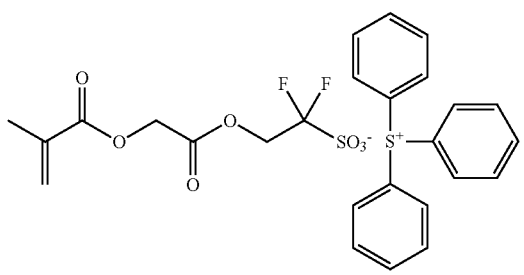

Into a 200-mL reaction vessel, 5.77 g (purity: 44%, 8.56 mmol) of sodium 2-[(methacryloyloxy)acetoxy]-1,1-difluoroethanesulfonate obtained in Preparation Example 2-1, 15 mL of water and 15 mL of chloroform were added. Then, 2.9 g (8.6 mmol) of triphenylsulfonium bromide was dropped into the reaction vessel at room temperature. The resulting solution was stirred for 2 hours at room temperature and subjected to separation. The thus-obtained organic phase was washed with 15 mL of water and subjected to solvent evaporation, thereby obtaining 3.58 g of target triphenylsulfonium 2-[(methacryloyloxy)acetoxy]-1,1-difluoroethanesulfonate as a crude product. The purity of the crude target product was 57%; and the yield of the crude target product was 76%. The obtained crude triphenylsulfonium 2-[(methacryloyloxy)acetoxy]-1,1-difluoroethanesulfonate was admixed with 6 g of chloroform, 3 g of ethyl acetate and 1.5 g of diisopropyl ether and totally dissolved in the solvent by heating. The resulting solution was cooled in air, thereby precipitating a solid out of the solution. The precipitated solid was filtered out and dried. With this, 2.32 g of the target 2-[(methacryloyloxy)acetoxy]-1,1-difluoroethanesulfonate was obtained with a purity of 98%.

Properties of 2-[(methacryloyloxy)acetoxy]-1,1-difluoroethanesulfonate $^{1}$H NMR (measurement solvent: deuterium dimethyl sulfoxide, reference material: tetramethylsilane) δ=7.86-7.75 (m, 15H; Ph$_3$S$^+$), 6.11 (s, 1H), 5.78 (s, 1H), 4.84 (s, 2H), 4.59 (t, J=15.6 Hz, 2H), 1.91 (s, 3H).
$^{19}$F NMR (measurement solvent: deuterium dimethyl sulfoxide, reference material: trichlorofluoromethane) δ=−113.8 (t, J=15.6 Hz, 2F).

Preparation Example 3-1

Preparation of 2,2-Difluoro-3-hydroxy-pentanoic Ethyl Ester

[Chem. 79]

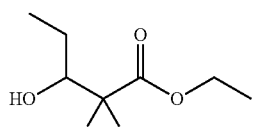

Into a 500-mL reaction vessel were added 24.2 g (370 mmol/1.5 eq) of activated zinc metal and 300 mL of THF (dehydrated form). Then, ethyl bromo difluoroacetate/THF solution (ethyl bromo difluoroacetate: 51, 47 g (253.6 mmol/1.0 eq), THF (dehydrated form): 80 mL) was dropped into the reaction vessel. After the dropping, the resulting solution was stirred for 20 minutes at room temperature. Subsequently, propionaldehyde/THF solution (propionaldehyde: 14.80 g (254.8 mmol/1.0 eq), THF (dehydrated form): 80 mL) was added to the solution. The solution was further stirred for 30 minutes at room temperature and subjected to two-phase separation by the addition of water and diisopropyl ether. The thus-obtained organic solution was washed with dilute hydrochloric acid and with water, treated with magnesium sulfate for water removal, filtered, and then, subjected evaporation of diisopropyl ether. With this, 41.2 g of target 2-methacrylic acid 2,2-diluforo-3-hydroxy-pentanoic ethyl ester was obtained. The yield of the target product was 89%.

Properties of 2,2-diluforo-3-hydroxy-pentanoic ethyl ester $^{1}$H NMR (measurement solvent: deuterium chloroform, reference material: tetramethylsilane) δ=4.31 (q, J=7.1 Hz, 2H; CH$_2$—O), 3.89 (m, 1H; CH—OH), 2.50 (br, 1H; OH), 1.71 (m, 1H), 1.52 (m, 1H), 1.32 (t, J=7.1 Hz, 3H; CH$_3$), 1.02 (t, J=7.3 Hz, 3H; CH$_3$).
$^{19}$F NMR (measurement solvent: deuterium chloroform, reference material: trichlorofluoromethane) δ=−115.26 (d, J=252 Hz, 1F), −122.95 (d, J=252 Hz, 1F).

Preparation Example 3-2

Preparation of Methacrylic Acid 1-Ethoxycarbonyl-1,1-difluoro-2-butyl Ester

[Chem. 80]

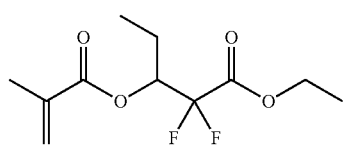

In a 25-mL reaction vessel, 1.50 g (8.2 mmol) of 2,2-difluoro-3-hydroxy-pentanoic ethyl ester obtained in Preparation Example 3-1, 6.5 g of chloroform, 10 mg of antioxidant "NONFLEX MBP" (manufactured by Seiko Chemical Co., Ltd.), 1.03 g (9.9 mmol/1.2 eq) of methacrylic chloride and 1.25 g (12.4 mmol/1.5 eq) of triethylamine ware added. The resulting solution was stirred for 4 hours at 55° C., followed by adding 10 g of water to the solution. The solution was treated with magnesium sulfate for water removal, filtered, and then, subjected to evaporation of chloroform. With this, 2.06 g of target methacrylic acid 1-ethoxycarbonyl-1,1-difluoro-2-butyl ester was obtained. The purity of the target product was 66%; and the yield of the target product was 66%.

Properties of methacrylic acid
1-ethoxycarbonyl-1,1-difluoro-2-butyl ester $^{1}$H NMR (measurement solvent: deuterium chloroform, reference material: tetramethylsilane) δ=6.14 (s, 1H; —CH$_2$—), 5.62 (s, 1H; —CH$_2$—), 5.35 (m, 1H; CH—O), 4.27 (m, 2H; CH$_2$—O), 1.93 (s, 3H; CH$_3$), 1.81 (m, 2H; CH$_2$), 1.28 (t, J=7.2 Hz, 3H; CH$_3$), 0.95 (t, J=7.6 Hz, 3H; CH$_3$).

$^{19}$F NMR (measurement solvent: deuterium chloroform, reference material: trichlorofluoromethane) δ=−113.63 (d, J=264 Hz, 1F), −119.57 (d, J=264 Hz, 1F).

Preparation Example 3-3

Preparation of Methacrylic Acid
1-Hydroxycarbonyl-1,1-diluforo-2-butyl Ester

[Chem. 81]

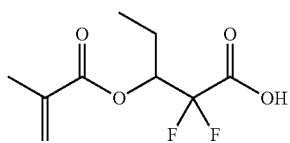

Into a 25-mL reaction vessel were added 1.00 g (purity: 66%, 2.6 mmol) of methacrylic acid 1-ethoxycrabonyl-1,1-difluoro-2-butyl ester obtained in Preparation Example 3-2 and 1.00 g of water, followed by dropping 1.06 (4.0 mmol/1.5 eq) of 15 mass % aqueous sodium hydroxide solution into the reaction vessel while cooling the reaction vessel at 0° C. The resulting solution was stirred for 1 hour at room temperature. The reaction solution was washed with 10 g of diisopropyl ether. The thus-obtained aqueous phase was washed with dilute hydrochloric acid, extracted twice with diisopropyl ether, treated with magnesium sulfate for water removal, filtered, and then, subjected to evaporation of diisopropyl ether. With this, 0.19 g of target methacrylic acid 1-hydroxycarbonyl-1,1-diluforo-2-butyl ester was obtained. The purity of the target product was 78%; and the yield of the target product was 27%.

Properties of methacrylic acid
1-hydroxycarbonyl-1,1-diluforo-2-butyl ester $^{1}$H NMR (measurement solvent: deuterium chloroform, reference material: tetramethylsilane) δ=7.24 (br, 1H; COOH), 6.16 (s, 1H; —CH$_2$—), 5.63 (s, 1H; —CH$_2$—), 5.39 (m, 1H; CH—O), 1.93 (s, 3H; CH$_3$), 1.85 (m, 2H; CH$_2$), 0.97 (t, J=7.6 Hz, 3H; CH$_3$), 0.95 (t, J=7.6 Hz, 3H; CH$_3$).

$^{19}$F NMR (measurement solvent: deuterium chloroform, reference material: trichlorofluoromethane) δ=−114.24 (d, J=264 Hz, 1F), −119.48 (d, J=264 Hz, 1F).

Preparation Example 3-4

Preparation of Methacrylic Acid
1-chlorocarbonyl-1,1-diluforo-2-butyl Ester

[Chem. 82]

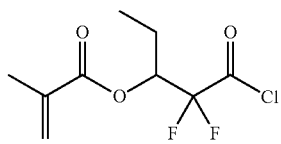

Into a 3-L container with a dropping funnel, 420 g (purity: 66%, 1.25 mol) of methacrylic acid 1-hydroxycarbonyl-1,1-diluforo-2-butyl ester obtained in Preparation Example 3-3, 7.50 g (0.11 mol/0.01 eq) of dimethylformamide were added. Further, 452 g (3.79 mol/3.0 eq) of thionyl chloride was dropped into the container at room temperature. The resulting solution was heated to 75° C. and stirred for 4 hours. It was confirmed by $^{19}$F NMR of the reaction solution that the reaction had been completed. Subsequently, the reaction solution was subjected to distillation under a reduced pressure. With this, 282 g of target methacrylic acid 1-chlorocarbonyl-1,1-diluforo-2-butyl ester was obtained. The purity of the target product was 98%; and the yield of the target product was 92%.

Properties of methacrylic acid
1-chlorocarbonyl-1,1-diluforo-2-butyl ester $^{1}$H NMR (measurement solvent: deuterium chloroform, reference material: tetramethylsilane) δ=6.14 (s, 1H; =CH$_2$), 5.63 (s, 1H; =CH$_2$), 5.43 (m, 1H; CH—O), 1.92 (s, 3H; CH$_3$—C), 1.82 (m, 2H; CH$_2$ of CH$_2$CH$_3$), 0.96 (t, J=7.6 Hz, 3H; CH$_3$ of CH$_2$CH$_3$).

$^{19}$F NMR (measurement solvent: deuterium chloroform, reference material: trichlorofluoromethane) δ=−108.10 (d, J=259 Hz, 1F), −114.01 (d, J=259 Hz, 1F).

Preparation Example 4-1

Preparation of Sodium 2-[3-(Methacryloyloxy)-2,2-difluoro-n-pentanoyloxy]-1,1-difluoroethane-sulfonate

[Chem. 83]

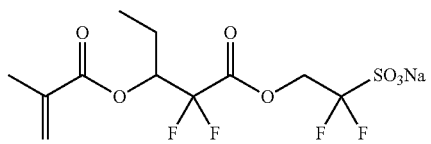

In a 50-mL reaction vessel with a dropping funnel were added 1.80 g (purity: 91%, 10.0 mmol/1.0 eq) of sodium 2-hydroxy-1,1-difluoroethanesulfonate, 8.0 mL of acetonitrile and 1.20 g of triethylamine. The resulting solution was stirred, followed by dropping thereinto 2.00 g (purity: 98%, 8.3 mmol) of methacrylic acid 1-chlorocarbonyl-1,1-difluoro-2-butyl ester obtained in Preparation Example 3-4. The solution was further stirred for 1 hour at room temperature. It was confirmed by $^{19}$F NMR of the reaction solution that the reaction had been completed. After that, the solution was filtered. The filtrate was concentrated under a reduced pressure, thereby obtaining 3.50 g of target sodium 2-[3-(methacryloyloxy)-2,2-difluoro-n-pentanoyloxy]-1,1-difluoroethanesulfonate as a colorless oily substance. The purity of the target product was 24%; and the yield of the target product was 26%.

Properties of sodium 2-[3-(methacryloyloxy)-2,2-difluoro-n-pentanoyloxy]-1,1-difluoroethanesulfonate]

$^{1}$H NMR (measurement solvent: deuterium dimethyl sulfoxide, reference material: tetramethylsilane) δ=6.08 (s, 1H; =CH$_2$), 5.78 (s, 1H; =CH$_2$), 5.32 (m, 1H; CH—O), 4.77 (t, J=16 Hz, 2H; CH$_2$—O), 1.88 (s, 3H; CH$_3$—C), 1.78 (m, 2H; CH$_2$ of CH$_2$CH$_3$), 0.88 (t, J=7.6 Hz, 3H; CH$_3$ of CH$_2$CH$_3$).
$^{19}$F NMR (measurement solvent: deuterium dimethyl sulfoxide, reference material: hexafluorobenzene) δ=48.33 (t, J=16 Hz, 2F), 46.60 (t, J=16 Hz, 2F).

Preparation Example 4-2

Preparation of Triphenylsulfonium 2-[3-(Methacryloyloxy)-2,2-difluoro-n-pentanoyloxy]-1,1-difluoroethanesulfonate

[Chem. 84]

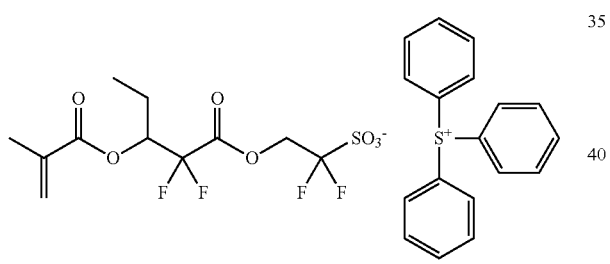

Into a 100-mL reaction vessel were added 2.82 g (purity: 24%, 1.74 mmol) of sodium 2-[3-(methacryloyloxy)-2,2-difluoro-n-pentanoyloxy]-1,1-difluoroethanesulfonate obtained in Preparation Example 4-1, 9 mL of water and 9 mL of chloroform. Further, 2.10 g (7.05 mmol) of triphenylsulfonium chloride was dropped into the reaction vessel at room temperature. The resulting solution was stirred for 2 hours at room temperature and subjected to separation. The thus-obtained organic phase was washed four times with 10 mL of water and concentrated under a reduced pressure. With this, 3.00 g of target triphenylsulfonium 2-[3-(methacryloyloxy)-2,2-difluoro-n-pentanoyloxy]-1,1-difluoroethanesulfonate was obtained as a colorless oily substance. The purity of the target product was 53%; and the yield of the target product was 100%.

Properties of triphenylsulfonium 2-[3-(methacryloyloxy)-2,2-difluoro-n-pentanoyloxy]-1,1-difluoroethanesulfonate]

$^{1}$H NMR (measurement solvent: deuterium chloroform, reference material: tetramethylsilane) δ=7.67 (m, 15H; Ph$_3$S$^+$), 6.08 (s, 1H; =CH$_2$), 5.53 (s, 1H; =CH$_2$), 5.34 (m, 1H; CH—O), 4.85 (t, J=16 Hz, 2H; CH$_2$—O), 1.84 (s, 3H; CH$_3$—C), 1.75 (m, 2H; CH$_2$ of CH$_2$CH$_3$), 0.88 (t, J=7.6 Hz, 3H; CH$_3$ of CH$_2$CH$_3$).
$^{19}$F NMR (measurement solvent: deuterium chloroform, reference material: trichlorofluoromethane) δ=−114.65 (t, J=16 Hz, 2F), −117.35 (t, J=16 Hz, 2F).

Using the prepared polymerizable monomers, resins were produced by the following procedures. The structures and abbreviations of the polymerizable monomers used are indicated below.

[Chem. 85]

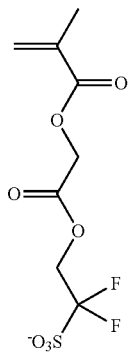
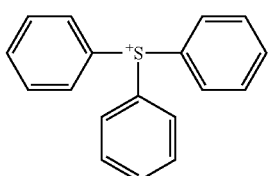

(PAG-1)

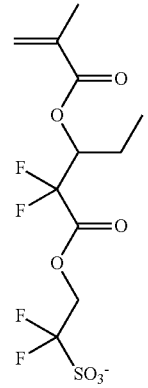
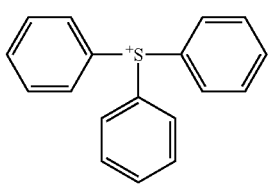

(PAG-2)

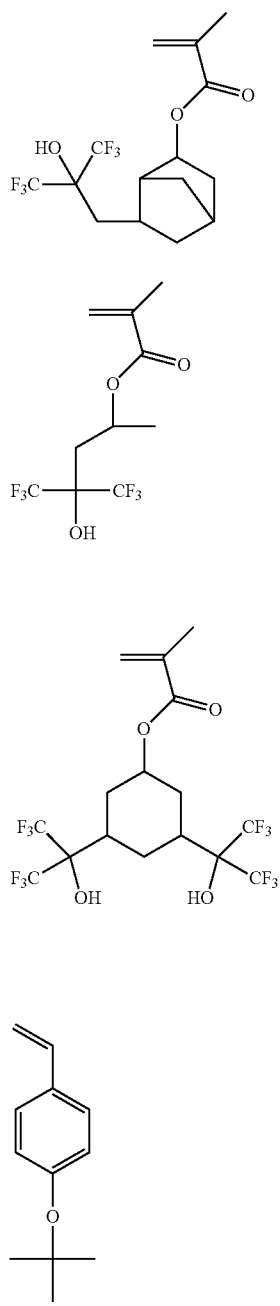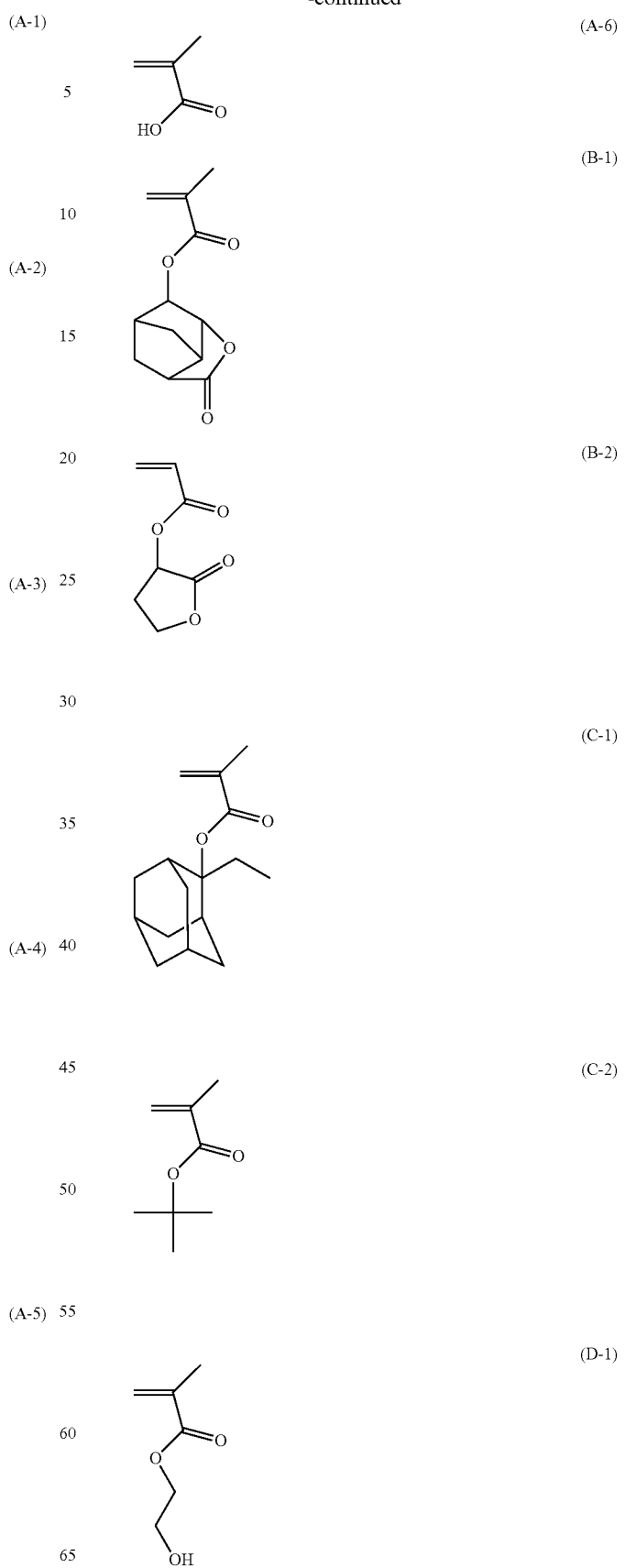

Production Example P-1

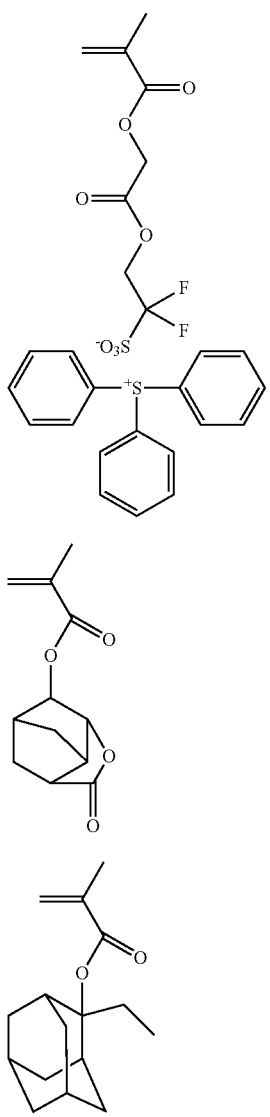

(PAG-1)

(B-1)

(C-1)

A monomer solution was prepared by dissolving 10.0 g (5 mol %) of compound (PAG-1), 40.4 g (50 mol %) of compound (B-1) and 40.6 g (45 mol %) of compound (C-1) in 300 g of 2-butanone and adding thereto 3.4 g of dimethyl 2,2'-azobis(2-methylpropionate). On the other hand, a 1000-mL three-neck flask was charged with 100 g of butanone, purged with nitrogen for 30 minutes and heated to 80° C. while stirring. The previously prepared monomer solution was dropped into the flask by a dropping funnel over 3 hours. The polymerization was performed for 6 hours by setting the initiation of the dropping as a polymerization initiation time. After the completion of the polymerization, the polymerization solution was cooled by water to 30° C. or lower and put into 2 kg of methanol to thereby precipitate a white powdery substance. The white powdery substance was filtered out of the solution, washed twice with 400 g of methanol in slurry form, filtered, and then, dried at 50° C. for 17 hours. With this, a polymer was obtained as a white powder (73 g). The average molecular weight Mw of the polymer was 8,800. Further, it was confirmed by $^{13}$C-NMR analysis that the polymer was in the form of a copolymer in which the content ratio of the repeating unit derived from the compound (PAG-1), the repeating unit derived from the compound (B-1) and the repeating unit derived from the compound (C-1) was 5.2:44.9:49.9 (mol %). The thus-obtained copolymer was named as "Resin P-1".

Production Example P-2

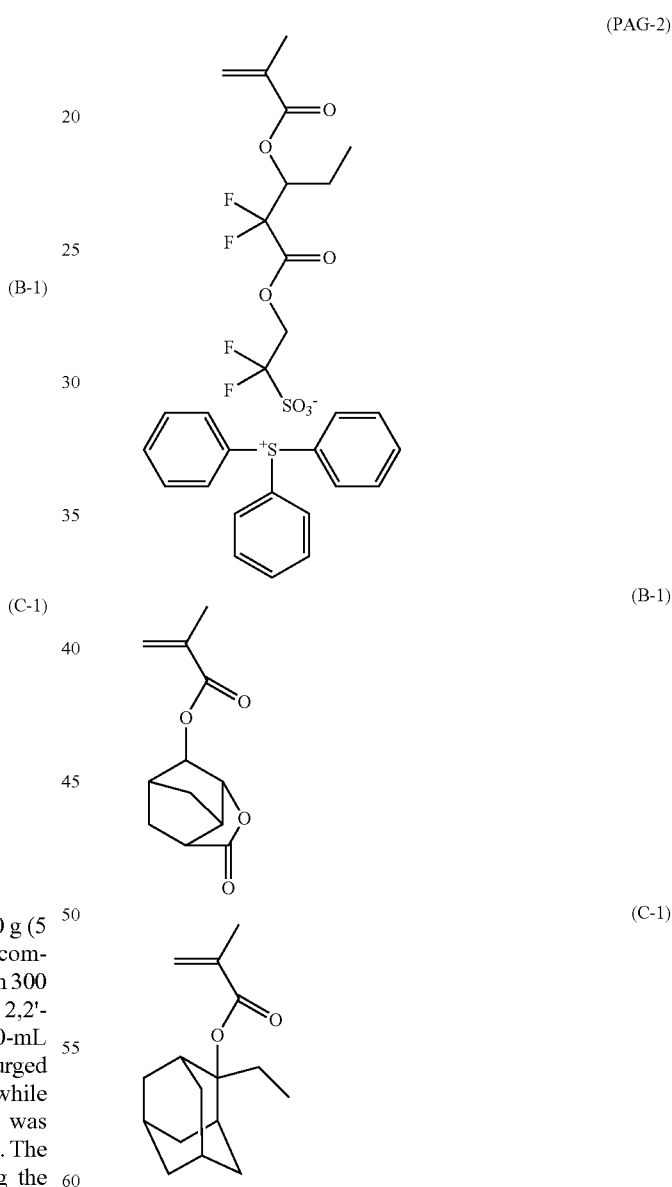

(PAG-2)

(B-1)

(C-1)

A monomer solution was prepared by dissolving 10.0 g (5 mol %) of compound (PAG-2), 35.6 g (50 mol %) of compound (B-1) and 35.6 g (45 mol %) of compound (C-1) in 300 g of 2-butanone and adding thereto 3.4 g of dimethyl 2,2'-azobis(2-methylpropionate). On the other hand, a 1000-mL three-neck flask was charged with 100 g of butanone, purged with nitrogen for 30 minutes and heated to 80° C. while stirring. The previously prepared monomer solution was dropped into the flask by a dropping funnel over 3 hours. The polymerization was performed for 6 hours by setting the initiation of the dropping as a polymerization initiation time. After the completion of the polymerization, the polymerization solution was cooled by water to 30° C. or lower and put into 2 kg of methanol to thereby precipitate a white powdery substance. The white powdery substance was filtered out of the solution, washed twice with 400 g of methanol in slurry form, filtered, and then, dried at 50° C. for 17 hours. With this, a polymer was obtained as a white powder (56.9 g). The average molecular weight Mw of the polymer was 8,400. Further, it was confirmed by $^{13}$C-NMR analysis that the polymer was in the form of a copolymer in which the content ratio of the repeating unit derived from the compound (PAG-2), the repeating unit derived from the compound (B-1) and the repeating unit derived from the compound (C-1) was 5.4: 44.7:49.9 (mol %). The thus-obtained copolymer was named as "Resin P-2".

Production Examples P-3 to P-19, X-1 to X-6 and N-1 to N-4

Resins P-3 to P-19, X-1 to X-6 and N-1 to N-4 were produced in the same manner as in Production Example P-1 or P-2. The kinds and contents of the copolymerization monomers used and the mole ratio of the repeating units derived from the respective monomers and the average molecular weight (Mw) of the polymer as measured after the copolymerization are indicated in TABLES 1 and 2.

TABLE 1

| Production Example Resin | Raw material composition | | | | | | | |
|---|---|---|---|---|---|---|---|---|
| | Monomer 1 | | Monomer 2 | | Monomer 3 | | Monomer 4 | |
| | Kind | mol % | Kind | mol % | Kind | mol % | Kind | mol % |
| P-1 | PAG-1 | 5 | — | — | B-1 | 50 | C-1 | 45 |
| P-2 | PAG-2 | 5 | — | — | B-1 | 50 | C-1 | 45 |
| P-3 | PAG-1 | 5 | A-1 | 20 | B-1 | 40 | C-1 | 35 |
| P-4 | PAG-1 | 5 | A-2 | 25 | B-1 | 40 | C-1 | 30 |
| P-5 | PAG-1 | 5 | A-3 | 20 | B-1 | 40 | C-1 | 35 |
| P-6 | PAG-1 | 5 | A-4 | 10 | B-1 | 40 | C-1 | 45 |
| P-7 | PAG-1 | 5 | A-1 | 20 | B-1 | 40 | C-2 | 35 |
| P-8 | PAG-2 | 5 | A-1 | 20 | B-1 | 40 | C-1 | 35 |
| P-9 | PAG-2 | 5 | A-2 | 25 | B-1 | 40 | C-1 | 30 |
| P-10 | PAG-2 | 5 | A-3 | 20 | B-1 | 40 | C-1 | 35 |
| P-11 | PAG-2 | 5 | A-4 | 10 | B-1 | 40 | C-1 | 45 |
| P-12 | PAG-2 | 5 | A-1 | 20 | B-1 | 40 | C-2 | 35 |
| P-13 | PAG-1 | 20 | A-5 | 30 | — | — | C-1 | 50 |
| P-14 | PAG-2 | 15 | A-5 | 30 | B-1 | 20 | C-1 | 45 |
| P-15 | PAG-2 | 5 | A-5 | 30 | B-1 | 30 | C-1 | 35 |
| P-16 | PAG-1 | 5 | A-5 | 30 | B-2 | 30 | C-1 | 35 |
| P-17 | PAG-1 | 20 | A-5 | 20 | B-2 | 20 | C-2 | 45 |
| P-18 | PAG-1 | 20 | — | — | B-1 | 30 | C-1 | 50 |
| P-19 | PAG-2 | 10 | — | — | B-1 | 35 | C-1 | 55 |

| Production Example Resin | Mole ratio of repeating units in resin | | | | Molecular weight Mw |
|---|---|---|---|---|---|
| | Monomer 1 | Monomer 2 | Monomer 3 | Monomer 4 | |
| P-1 | 5 | — | 49 | 51 | 8,800 |
| P-2 | 5 | — | 51 | 49 | 8,400 |
| P-3 | 5 | 21 | 39 | 35 | 7,600 |
| P-4 | 5 | 26 | 39 | 30 | 8,800 |
| P-5 | 5 | 21 | 39 | 35 | 8,100 |
| P-6 | 5 | 11 | 40 | 44 | 7,800 |
| P-7 | 5 | 20 | 39 | 35 | 7,500 |
| P-8 | 5 | 21 | 39 | 35 | 7,400 |
| P-9 | 5 | 26 | 39 | 30 | 8,700 |
| P-10 | 5 | 21 | 40 | 35 | 8,000 |
| P-11 | 5 | 10 | 40 | 45 | 7,700 |
| P-12 | 5 | 21 | 39 | 35 | 7,400 |
| P-13 | 18 | 31 | — | 51 | 9,500 |
| P-14 | 16 | 30 | 18 | 46 | 7,200 |
| P-15 | 6 | 31 | 27 | 36 | 9,900 |
| P-16 | 5 | 31 | 28 | 36 | 9,700 |
| P-17 | 14 | 21 | 19 | 46 | 6,600 |
| P-18 | 17 | — | 34 | 49 | 8,500 |
| P-19 | 9 | — | 37 | 54 | 5,300 |

Monomer 1: Polymerizable fluorine-containing monomer
Monomer 2, 3: Auxiliary monomer
Monomer 3: Monomer with acid labile group or cross-linking site

TABLE 2

| Production Example Resin | Raw material composition | | | | | | | |
|---|---|---|---|---|---|---|---|---|
| | Monomer 1 | | Monomer 2 | | Monomer 3 | | Monomer 4 | |
| | Kind | mol % | Kind | mol % | Kind | mol % | Kind | mol % |
| X-1 | PAG-1 | 100 | — | — | — | — | — | — |
| X-2 | PAG-2 | 100 | — | — | — | — | — | — |
| X-3 | PAG-1 | 30 | A-5 | 70 | — | — | — | — |
| X-4 | PAG-1 | 30 | A-1 | 50 | B-1 | 20 | — | — |
| X-5 | PAG-2 | 50 | A-1 | 20 | B-1 | 30 | — | — |
| X-6 | PAG-1 | 10 | A-5 | 50 | B-1 | 40 | — | — |
| N-1 | PAG-1 | 5 | — | — | B-1 | 10 | A-6 | 45 |
| | | | | | | | D-1 | 40 |
| N-2 | PAG-2 | 7 | A-2 | 68 | B-2 | 5 | A-5 | 20 |
| N-3 | PAG-1 | 5 | A-4 | 25 | B-3 | 50 | D-1 | 20 |
| N-4 | PAG-2 | 10 | — | 30 | B-3 | 60 | A-5 | — |

| Production Example Resin | Mole ratio of repeating units in resin | | | | Molecular weight Mw |
|---|---|---|---|---|---|
| | Monomer 1 | Monomer 2 | Monomer 3 | Monomer 4 | |
| X-1 | 100 | — | — | — | 3,400 |
| X-2 | 100 | — | — | — | 5,100 |
| X-3 | 28 | 72 | — | — | 8,700 |
| X-4 | 29 | 53 | 17 | — | 9,200 |
| X-5 | 48 | 21 | 31 | — | 6,900 |
| X-6 | 11 | 54 | 35 | — | 11,000 |
| N-1 | 5 | 43 | 8 | 43 | 9,200 |
| | | | | 44 | |
| N-2 | 7 | 69 | 6 | 18 | 8,900 |
| N-3 | 6 | 25 | 46 | 23 | 8,100 |
| N-4 | 12 | — | 58 | 29 | 10,500 |

Monomer 1: Polymerizable fluorine-containing monomer
Monomer 2, 3: Auxiliary monomer
Monomer 3: Monomer with acid labile group or cross-linking site Examples 1 to 33

Preparation of Resist Solutions

Resist compositions were each prepared by mixing the above-produced resin with a solvent and other additives. The component ratios of the prepared resist compositions are indicated in TABLES 3 and 4. The resist compositions were filtrated with 0.2-μm membrane filters, respectively, thereby obtaining resist solutions.

The kinds of the solvent, the basic compound and the cross-linking agent used in each example are indicated below.
S-1: Propylene glycol monomethyl ether acetate (PGMEA)
S-2: γ-Butyrolactone
S-3: Ethyl lactate
S-4: Cyclohexanone
O-1: N,N-Dibutylaniline
O-2: 2,6-Diisopropylaniline
O-3: Diazabicyclo[4.3.0]nonene
O-4: 2,4,5-Triphenylimidazole
O-5: Ttrioctylamine
Cross-linking agent: NIKALAC MX-270 (glycoluril cross-linking agent, manufactured by Sanwa Chemical Co., Ltd.)

[Chem. 88]

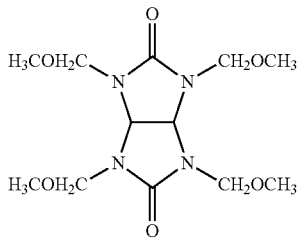

[Pattern Formation]

Each of the obtained resist solutions was spin-coated on a silicon wafer substrate to form a resist film of 250 nm thickness. The resist film was prebaked at 110° C., exposed to a 248-nm ultraviolet radiation through a photomask, and then, subjected to post exposure baking treatment at 120° C. After that, the resist film was developed with 2.38 mass % aqueous tetramethylammoniumhydroxide solution for 1 minute at 23° C. It was possible to obtain a pattern shape with high resolution from each of the resist compositions. There were seen no failures such as poor adhesion of the resist film to the substrate, poor film formation, development failure and poor etching resistance. The resist compositions and evaluation results are indicated in TABLES 3 and 4.

TABLE 3

| Example | Resin 1 Kind | Resin 1 Parts by mass | Resin 2 Kind | Resin 2 Parts by mass |
|---|---|---|---|---|
| 1 | P-1 | 40 | None | — |
| 2 | P-3 | 40 | None | — |
| 3 | P-4 | 40 | None | — |
| 4 | P-5 | 14 | P'-3 | 26 |
| 5 | P-6 | 40 | None | — |
| 6 | P-7 | 40 | None | — |
| 7 | P-2 | 40 | None | — |
| 8 | P-8 | 40 | None | — |
| 9 | P-9 | 14 | P'-2 | 26 |
| 10 | P-10 | 40 | None | — |
| 11 | P-11 | 40 | None | — |
| 12 | P-12 | 40 | None | — |

| Example | Additive | Solvent Kind | Solvent Parts by mass | Pattern shape |
|---|---|---|---|---|
| 1 | O-1 | S-1 | 400 | Clean rectangular shape |
| 2 | O-1 | S-2 | 400 | Clean rectangular shape |
| 3 | O-2 | S-1 | 400 | Clean rectangular shape |
| 4 | O-3 | S-1 | 400 | Clean rectangular shape |
| 5 | O-3 | S-1 | 400 | Clean rectangular shape |
| 6 | O-1 | S-1 | 400 | Clean rectangular shape |
| 7 | O-1 | S-1 | 400 | Clean rectangular shape |
| 8 | O-1 | S-3 | 400 | Clean rectangular shape |
| 9 | O-4 | S-4 | 400 | Clean rectangular shape |
| 10 | O-5 | S-1 | 400 | Clean rectangular shape |
| 11 | O-5 | S-1 | 400 | Clean rectangular shape |
| 12 | O-5 | S-1 | 400 | Clean rectangular shape |

Basic compound: Added amount (0.15 parts by mass)
O-1: N,N-Dibutylaniline
O-2: 2,6-Diisopropylaniline
O-3: Diazabicyclo[4.3.0]nonene
O-4: 2,4,5-Triphenylimidazole
O-5: Trioctylamine
Solvent
S-1: Propylene glycol monomethyl ether acetate (PGMEA)
S-2: γ-Butyrolactone
S-3: Ethyl lactate
S-4: Cyclohexanone

TABLE 4

| Example | Resin 1 Kind | Resin 1 Parts by mass | Resin 2 Kind | Resin 2 Parts by mass |
|---|---|---|---|---|
| 13 | P-13 | 20 | P'-1 | 20 |
| 14 | P-14 | 20 | P'-2 | 20 |
| 15 | P-15 | 20 | P'-1 | 20 |
| 16 | P-16 | 20 | P'-2 | 20 |
| 17 | P-17 | 20 | P'-2 | 20 |
| 18 | P-18 | 40 | None | — |
| 19 | P-19 | 40 | None | — |
| 20 | X-1 | 2 | P'-1 | 40 |
| 21 | X-1 | 4 | P'-2 | 40 |
| 22 | X-2 | 6 | P'-1 | 40 |
| 23 | X-2 | 1 | P'-2 | 40 |
| 24 | X-3 | 12 | P'-3 | 32 |
| 25 | X-4 | 30 | P'-4 | 19 |
| 26 | X-5 | 30 | P'-5 | 25 |
| 27 | X-6 | 30 | P'-1 | 13 |
| 28 | X-2 | 6 | P'-6 | 40 |
| 29 | N-1 | 40 | None | — |
| 30 | N-1 | 20 | P'-4 | 20 |
| 31 | N-2 | 40 | None | — |
| 32 | N-3 | 40 | None | — |
| 33 | N-4 | 40 | None | — |

| Example | Additive | Solvent Kind | Solvent Parts by mass | Pattern shape |
|---|---|---|---|---|
| 13 | O-1 | S-1 | 400 | Clean rectangular shape |
| 14 | O-1 | S-1 | 400 | Clean rectangular shape |
| 15 | O-5 | S-1 | 400 | Clean rectangular shape |
| 16 | O-3 | S-2 | 400 | Clean rectangular shape |
| 17 | O-5 | S-1 | 400 | Clean rectangular shape |
| 18 | O-5 | S-3 | 400 | Clean rectangular shape |
| 19 | O-2 | S-1 | 400 | Clean rectangular shape |
| 20 | O-5 | S-1 | 400 | Clean rectangular shape |
| 21 | O-5 | S-1 | 400 | Clean rectangular shape |
| 22 | O-5 | S-4 | 400 | Clean rectangular shape |
| 23 | O-5 | S-1 | 400 | Clean rectangular shape |
| 24 | O-1 | S-1 | 400 | Clean rectangular shape |
| 25 | O-1 | S-1 | 400 | Clean rectangular shape |
| 26 | O-5 | S-1 | 400 | Clean rectangular shape |
| 27 | O-5 | S-1 | 400 | Clean rectangular shape |
| 28 | Cross-linking agent O-5 | S-1 | 400 | Clean rectangular shape |
| 29 | Cross-linking agent O-5 | S-1 | 400 | Clean rectangular shape |
| 30 | Cross-linking agent O-5 | S-1 | 400 | Clean rectangular shape |
| 31 | Cross-linking agent O-1 | S-1 | 400 | Clean rectangular shape |
| 32 | Cross-linking agent O-4 | S-2 | 400 | Clean rectangular shape |
| 33 | Cross-linking agent O-5 | S-3 | 400 | Clean rectangular shape |

Cross-linking agent: NIKALAC MX-270 (glycoluril cross-linking agent, manufactured by Sanwa Chemical Co., Ltd.) added in amount of 3 parts by mass
O-1: N,N-Dibutylaniline
O-2: 2,6-Diisopropylaniline
O-3: Diazabicyclo[4.3.0]nonene
O-4: 2,4,5-Triphenylimidazole
O-5: Trioctylamine
Solvent
S-1: Propylene glycol monomethyl ether acetate (PGMEA)
S-2: γ-Butyrolactone
S-3: Ethyl lactate
S-4: Cyclohexanone Reference Production Examples Using various monomers shown in TABLE 5, resins each containing no sulfonate (P-1' to P-5') were produced in the same manner as in Production Examples 1 and 2. The mole ratio of the repeating units and the average molecular weight (Mw) of each of the obtained resins are indicated in TABLE 5.

TABLE 5

| Production Example Resin | Monomer R1 Kind | Monomer R1 mol % | Monomer R2 Kind | Monomer R2 mol % | Monomer R3 Kind | Monomer R3 mol % |
|---|---|---|---|---|---|---|
| P-1' | A-1 | 20 | B-1 | 45 | C-1 | 35 |
| P-2' | A-2 | 25 | B-1 | 45 | C-1 | 30 |
| P-3' | A-3 | 20 | B-1 | 45 | C-1 | 35 |
| P-4' | A-4 | 10 | B-1 | 45 | C-1 | 45 |
| P-5' | A-1 | 20 | B-1 | 45 | C-2 | 35 |

| Production Example Resin | Monomer R1 | Monomer R2 | Monomer R3 | Molecular weight Mw |
|---|---|---|---|---|
| P-1' | 21 | 45 | 34 | 8,300 |
| P-2' | 26 | 43 | 31 | 8,900 |
| P-3' | 19 | 45 | 36 | 8,500 |
| P-4' | 10 | 46 | 44 | 7,800 |
| P-5' | 20 | 44 | 36 | 8,600 |

TABLE 6

| Reference Example | Resin Kind | Resin Parts by mass | Additive | Solvent Kind | Solvent Parts by mass | Pattern shape |
|---|---|---|---|---|---|---|
| 1 | P'-1 | 40 | PAG-3 O-1 | S-1 | 400 | Slightly distorted rectangular shape |
| 2 | P'-2 | 40 | PAG-3 O-2 | S-4 | 400 | Slightly distorted rectangular shape |
| 3 | P'-3 | 40 | PAG-3 O-1 | S-1 | 400 | Slightly distorted rectangular shape |
| 4 | P'-4 | 40 | PAG-3 O-1 | S-1 | 400 | Slightly distorted rectangular shape |
| 5 | P'-5 | 40 | PAG-3 O-3 | S-1 | 400 | Distorted rectangular shape |
| 6 | P'-1 | 40 | PAG-4 O-1 | S-2 | 400 | Distorted rectangular shape |
| 7 | P'-2 | 40 | PAG-4 O-4 | S-3 | 400 | Distorted rectangular shape |
| 8 | P'-3 | 40 | PAG-4 O-1 | S-1 | 400 | Distorted rectangular shape |
| 9 | P'-4 | 40 | PAG-4 O-1 | S-1 | 400 | Distorted rectangular shape |
| 10 | P'-5 | 40 | PAG-4 O-5 | S-1 | 400 | Distorted rectangular shape |

Photoacid generator added in amount of 4 parts by mass
Basic compound: Added amount (0.15 parts by mass)
O-1: N,N-Dibutylaniline
O-2: 2,6-Diisopropylaniline
O-3: Diazabicyclo[4.3.0]nonene
O-4: 2,4,5-Triphenylimidazole
O-5: Trioctylamine
Solvent
S-1: Propylene glycol monomethyl ether acetate (PGMEA)
S-2: γ-Butyrolactone
S-3: Ethyl lactate
S-4: Cyclohexanone

Reference Examples

Resist compositions and resist solutions were prepared using the above produced resins P-1' to P-5', each of which did not have the sulfonate structure of the present invention, in the same manner as in Examples 1 to 33. Resist patterns were formed from the respective prepared resist solutions in the same manner as in the above pattern formation test. The shapes of the resist patterns were then observed. In contrast to the above examples, there were observed pattern distortions in the reference examples. The results are indicated in TABLE 6. Further, the chemical structures of conventional photoacid generators, triphenylsulfonium trifluoromethanesulfonate (PAG-3) and triphenylsulfonium nonafluorobutanesulfonate (PAG-4) are indicated below.

[Chem. 89]

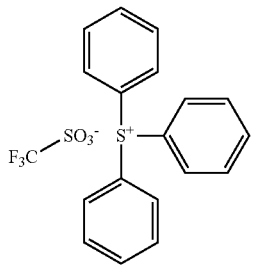

(PAG-3)

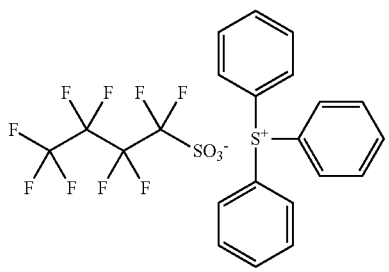

(PAG-4)

As described above, the resin having its side chain formed with the fluorine-containing sulfonic acid onium salt of the present invention functions as the photoacid generator effectively when used in the resist composition containing at least either the positive resist resin having the acid labile group or the negative resist resin having the cross-linking site, the acid generator and solvent (and additionally a cross-linking agent in the case of the negative resist type). It is therefore possible by the use of such a resin that the resist composition can attain high resolution, broad depth of focus tolerance (DOF), small line edge roughness (LER) and high sensitivity. It is also possible in the present invention to provide the specific monomer suitable for preparation of such a photoacid generator and the production method thereof as well as the pattern formation method suitable for use with the resist composition.

INDUSTRIAL APPLICABILITY

The sulfonate resin of the present invention can be used as a photoacid generator of a photoresist material and as a positive or negative resist resin. The monomer and intermediate thereof for production of this resin are also useful as a raw material for production of other compounds.

The invention claimed is:
1. A polymerizable fluorine-containing sulfonic acid or sulfonate having a structure of the following general formula (1):

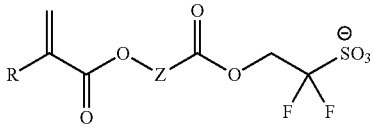
(1)

where Z represents a substituted or unsubstituted $C_1$-$C_6$ straight or branched alkylene group, or a divalent moiety in which substituted or unsubstituted $C_1$-$C_6$ straight or branched alkylene groups are bonded in series to a divalent group obtained by elimination of two hydrogen atoms from an alicyclic or aromatic hydrocarbon; and R represents a hydrogen atom, a halogen atom, or a $C_1$-$C_3$ alkyl or fluorine-containing alkyl group.

2. The polymerizable fluorine-containing sulfonic acid or sulfonate according claim 1, wherein said sulfonic acid or sulfonate is a polymerizable fluorine-containing sulfonic acid onium salt of the following general formula (2):

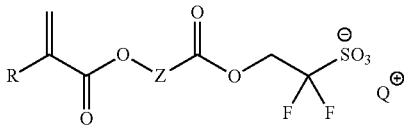
(2)

where Z and R have the same definition as in the general formula (1); and $Q^+$ represents a sulfonium cation of the following general formula (a) or the following general formula (b), or an iodonium cation of the following general formula (c),

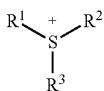
(a)

where $R^1$, $R^2$ and $R^3$ each independently represents a substituted or unsubstituted $C_1$-$C_{20}$ straight, branched or cyclic alkyl, alkenyl or oxoalkyl group, or a substituted or unsubstituted $C_6$-$C_{18}$ aryl, aralkyl or aryloxoalkyl group; and two or more of $R^1$, $R^2$ and $R^3$ may be bonded to each other to form a ring with a sulfur atom in the formula,

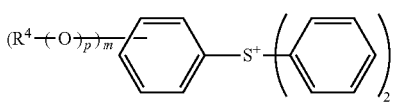
(b)

where $R^4$—$(O)_p$— are independent of each other; $R^4$ represents a substituted or unsubstituted $C_1$-$C_{20}$ straight, branched or cyclic alkyl or alkenyl group, or a substituted or unsubstituted $C_6$-$C_{14}$ aryl group; m represents an integer of 1 to 5; p represents 0 or 1; and $R^4$ may contain a carbonyl group, a hydroxyl group, an ester bond, a lactone ring, an amino group, an amide group or an ether bond as a substituent group,

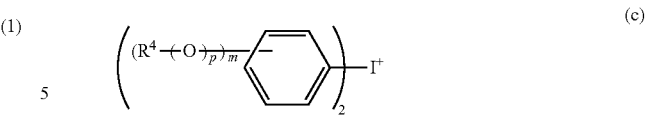
(c)

where $R^4$—$(O)_p$— are independent of each other; $R^4$ represents a substituted or unsubstituted $C_1$-$C_{20}$ straight, branched or cyclic alkyl or alkenyl group, or a substituted or unsubstituted $C_6$-$C_{14}$ aryl group; m represents an integer of 1 to 5; p represents 0 or 1; and $R^4$ may contain a carbonyl group, a hydroxyl group, an ester bond, a lactone ring, an amino group, an amide group or an ether bond as a substituent group.

3. A polymerizable fluorine-containing sulfonate compound of the following general formula (3):

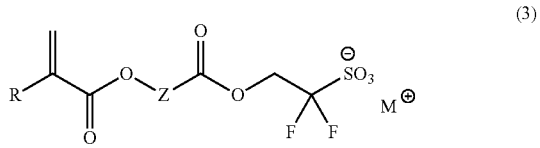
(3)

where Z represents a substituted or unsubstituted $C_1$-$C_6$ straight or branched alkylene group, or a divalent moiety in which substituted or unsubstituted $C_1$-$C_6$ straight or branched alkylene groups are bonded in series to a divalent group obtained by elimination of two hydrogen atoms from an alicyclic or aromatic hydrocarbon; and R represents a hydrogen atom, a halogen atom, or a $C_1$-$C_3$ alkyl or fluorine-containing alkyl group; and $M^+$ represents one of a lithium ion, a sodium ion, a potassium ion and ammonium ions.

4. A resin having either one of repeating units of the following general formulas (4) and (5):

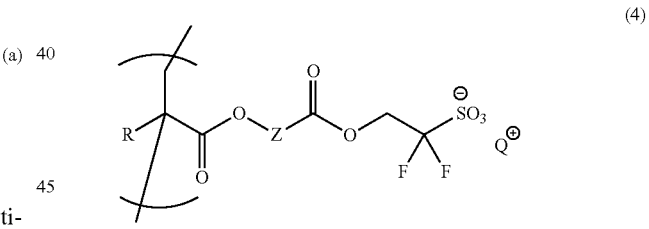
(4)

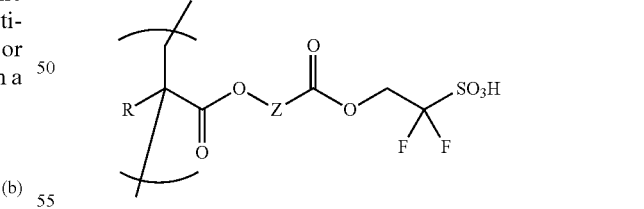
(5)

where Z represents a substituted or unsubstituted $C_1$-$C_6$ straight or branched alkylene group, or a divalent moiety in which substituted or unsubstituted $C_1$-$C_6$ straight or branched alkylene groups are bonded in series to a divalent group obtained by elimination of two hydrogen atoms from an alicyclic or aromatic hydrocarbon; R represents a hydrogen atom, a halogen atom, or a $C_1$-$C_3$ alkyl or fluorine-containing alkyl group; and $Q^+$ represents a sulfonium cation of the following general formula (a) or the following general formula (b), or an iodonium cation of the following general formula (c), (a)

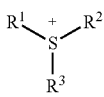

where $R^1$, $R^2$ and $R^3$ each independently represents a substituted or unsubstituted $C_1$-$C_{20}$ straight, branched or cyclic alkyl, alkenyl or oxoalkyl group, or a substituted or unsubstituted $C_6$-$C_{18}$ aryl, aralkyl or aryloxoalkyl group; and two or more of $R^1$, $R^2$ and $R^3$ may be bonded to each other to form a ring with a sulfur atom in the formula, (b)

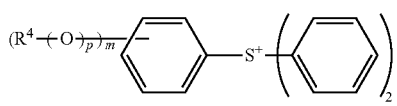

where $R^4$—$(O)_p$— are independent of each other; $R^4$ represents a substituted or unsubstituted $C_1$-$C_{20}$ straight, branched or cyclic alkyl or alkenyl group, or a substituted or unsubstituted $C_6$-$C_{14}$ aryl group; m represents an integer of 1 to 5; p represents 0 or 1; and $R^4$ may contain a carbonyl group, a hydroxyl group, an ester bond, a lactone ring, an amino group, an amide group or an ether bond as a substituent group, (c)

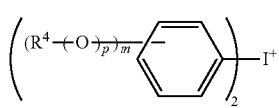

where $R^4$—$(O)_p$— are independent of each other; $R^4$ represents a substituted or unsubstituted $C_1$-$C_{20}$ straight, branched or cyclic alkyl or alkenyl group, or a substituted or unsubstituted $C_6$-$C_{14}$ aryl group; m represents an integer of 1 to 5; p represents 0 or 1; and $R^4$ may contain a carbonyl group, a hydroxyl group, an ester bond, a lactone ring, an amino group, an amide group or an ether bond as a substituent group.

5. The resin according to claim 4, further having at least one selected from the group consisting of repeating units formed by cleavage of polymerizable double bonds of olefins, fluorine-containing olefins, acrylic esters, methacrylic esters, fluorine-containing acrylic esters, fluorine-containing methacrylic esters, norbornene compounds, fluorine-containing norbornene compounds, styrenic compounds, fluorine-containing styrenic compounds, vinyl ethers and fluorine-containing vinyl ethers.

6. The resin according to claim 4, further having a repeating unit of the following general formula (6):

(6)

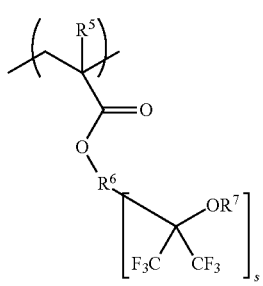

where $R^5$ represents a hydrogen atom, a halogen atom, or a $C_1$-$C_3$ alkyl or fluorine-containing alkyl group; $R^6$ represents a substituted or unsubstituted, straight, branched or cyclic structure-containing alkylene group, a substituted or unsubstituted divalent aromatic group, or a divalent organic moiety in which a plurality of substituted or unsubstituted, straight, branched or cyclic structure-containing alkylene and/or substituted or unsubstituted divalent aromatic groups are bonded to each other, and may be partially fluorinated; $R^7$ represents a hydrogen atom, a substituted or unsubstituted $C_1$-$C_{25}$ straight, branched or cyclic aliphatic hydrocarbon group, or a substituted or unsubstituted $C_1$-$C_{25}$ aromatic hydrocarbon group, a part of which may contain a fluorine atom, an ether bond or a carbonyl group; and s represents an integer of 1 or 2.

7. The resin according to claim 4, further having a repeating unit of the following general formula (7):

(7)

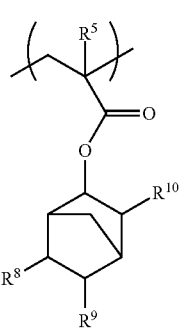

where $R^5$ represents a hydrogen atom, a halogen atom, or a $C_1$-$C_3$ alkyl or fluorine-containing alkyl group; either one of $R^8$, $R^9$ and $R^{10}$ represents a $CF_3C(CF_3)(OH)CH_2$— group; and the other two of $R^8$, $R^9$ and $R^{19}$ each represent a hydrogen atom.

8. The resin according to claim 4, further having a repeating unit of the following general formula (8):

(8)

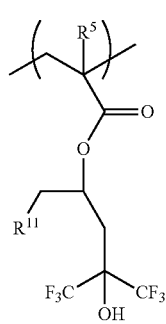

where $R^5$ represents a hydrogen atom, a halogen atom, or a $C_1$-$C_3$ alkyl or fluorine-containing alkyl group; and $R^{11}$ represents a $C_1$-$C_4$ alkyl or fluorine-containing alkyl group.

9. The resin according to claim 4, further having a repeating unit of the following general formula (9):

(9)

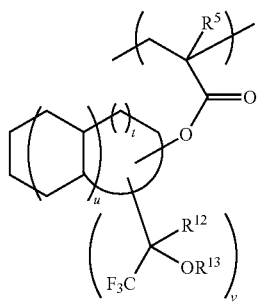

where $R^5$ represents a hydrogen atom, a halogen atom, or a $C_1$-$C_3$ alkyl or fluorine-containing alkyl group; $R^{12}$ represents a methyl group or a trifluoromethyl group; $R^{13}$ represents a hydrogen atom, a substituted or unsubstituted $C_1$-$C_{25}$ straight, branched or cyclic aliphatic hydrocarbon group, or a substituted or unsubstituted $C_1$-$C_{25}$ aromatic hydrocarbon group, a part of which may contain a fluorine atom, an ether bond or a carbonyl group; u represents an integer of 0 to 2; t and v each independently represent an integer of 1 to 8 and satisfy a relationship of $v \leq t+2$; and, when v is 2 to 8, $R^{12}$ and $R^{13}$ may be the same or different.

10. The resin according to claim 4, further having a repeating unit of the following general formula (10):

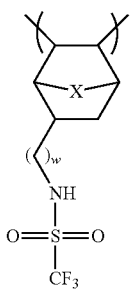

(10)

where X represents either of —$CH_2$—, —O— and —S—; and w represents an integer of 2 to 6.

11. The resin according to claim 4, further having a repeating unit of the following general formula (11):

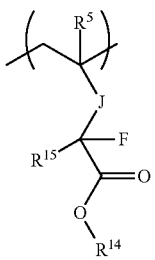

(11)

where $R^5$ represents a hydrogen atom, a halogen atom, or a $C_1$-$C_3$ alkyl or fluorine-containing alkyl group; $R^{15}$ represents a fluorine atom, or a fluorine-containing alkyl group; J represents a divalent linking group; and $R^{14}$ represents a hydrogen atom, a substituted or unsubstituted $C_1$-$C_{25}$ straight, branched or cyclic aliphatic hydrocarbon group, or a substituted or unsubstituted $C_1$-$C_{25}$ aromatic hydrocarbon group, a part of which may contain a fluorine atom, an ether bond or a carbonyl group.

12. A resist material, comprising:
at least the resin according to claim 4; and
a solvent.

13. The resist material according to claim 12, wherein the resin has an acid labile group so that the resist material functions as a chemically amplified positive resist material.

14. The resist material according to claim 12, wherein the resist material further comprises a resin having an acid labile group and functions as a chemically amplified positive resist material.

15. The resist material according to claim 12, wherein the resin has an alcoholic hydroxyl group or a carboxyl group so that the resist material functions as a chemically amplified negative resist material.

16. The resist material according to claim 12, wherein the resist material further comprises a resin having an alcoholic hydroxyl group or a carboxyl group and functions as a chemically amplified negative resist material.

17. A pattern forming method, comprising:
applying the resist material according to claim 12 to a substrate;
after heat treating the applied resist material, exposing the applied resist material to high energy radiation of 300 nm or less wavelength through a photomask; and
after heat treating the exposed resist material as needed, developing the exposed resist material with a developer.

18. The pattern formation method according to claim 17, wherein the exposing is performed by immersion lithography using ArF excimer laser radiation of 193 nm wavelength and allowing insertion of water or any other liquid of higher refractive index than that of the air between the substrate to which the resist material is applied and projector lens.

19. The polymerizable fluorine-containing sulfonic acid or sulfonate according claim 2, wherein the polymerizable fluorine-containing sulfonic acid onium salt is a compound of the following formula (12):

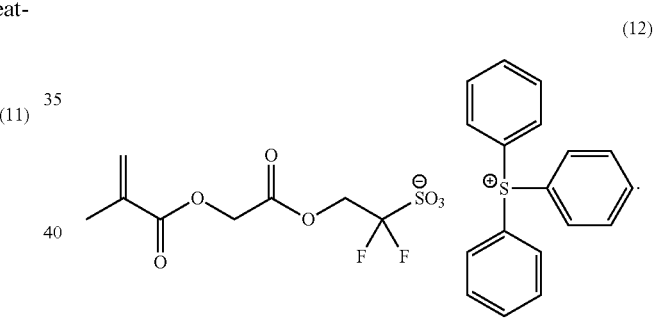

(12)

20. The polymerizable fluorine-containing sulfonic acid or sulfonate according claim 2, wherein the polymerizable fluorine-containing sulfonic acid onium salt is a compound of the following formula (13):

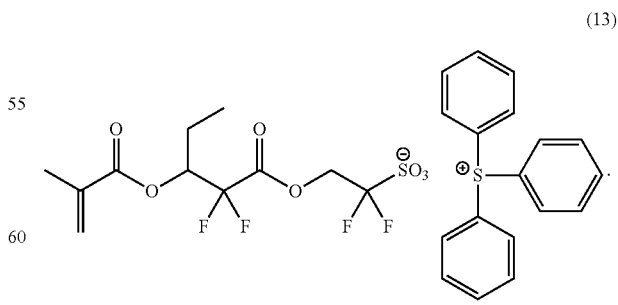

(13)

21. The polymerizable fluorine-containing sulfonate compound according to claim 3, wherein said sulfonate compound is a compound of the following formula (14):

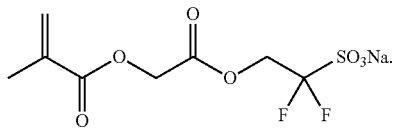
(14)

22. The polymerizable fluorine-containing sulfonate compound according to claim 3, wherein said sulfonate compound is a compound of the following formula (15):

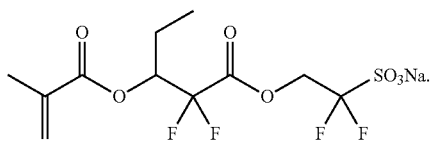
(15)

23. A method for producing a polymerizable fluorine-containing sulfonate compound of the following general formula (3), comprising performing esterification of a carboxylic acid derivative of the following general formula (16) and a 1,1-difluoro-2-hydroxyethanesulfonate of the following general formula (17):

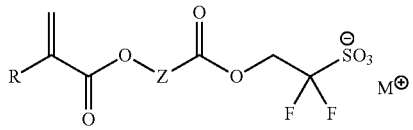
(3)

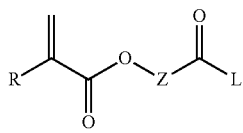
(16)

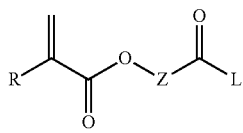
(17)

where Z represents a substituted or unsubstituted $C_1$-$C_6$ straight or branched alkylene group, or a divalent moiety in which substituted or unsubstituted $C_1$-$C_6$ straight or branched alkylene groups are bonded in series to a divalent group obtained by elimination of two hydrogen atoms from an alicyclic or aromatic hydrocarbon; R represents a hydrogen atom, a halogen atom, or a $C_1$-$C_3$ alkyl or fluorine-containing alkyl group; L represents a hydroxyl group or a halogen atom; and $M^+$ represents one of a lithium ion, a sodium ion, a potassium ion and ammonium ions.

24. A method for producing a polymerizable fluorine-containing sulfonic acid onium salt of the following general formula (2), comprising performing onium salt exchange reaction of a polymerizable fluorine-containing sulfonate compound of the following general formula (3) with a monovalent onium salt of the following general formula (18):

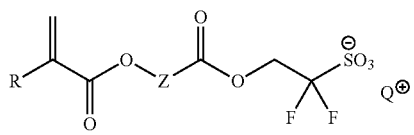
(2)

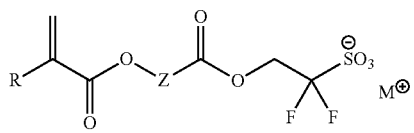
(3)

$Q^+Y^-$ (18)

where Z represents a substituted or unsubstituted $C_1$-$C_6$ straight or branched alkylene group, or a divalent moiety in which substituted or unsubstituted $C_1$-$C_6$ straight or branched alkylene groups are bonded in series to a divalent group obtained by elimination of two hydrogen atoms from an alicyclic or aromatic hydrocarbon; R represents a hydrogen atom, a halogen atom, or a $C_1$-$C_3$ alkyl or fluorine-containing alkyl group; $M^+$ represents one of a lithium ion, a sodium ion, a potassium ion and ammonium ions; $Y^-$ represents a monovalent anion; and $Q^+$ represents a sulfonium cation of the following general formula (a) or the following general formula (b), or an iodonium cation of the following general formula (c),

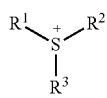
(a)

where $R^1$, $R^2$ and $R^3$ each independently represents a substituted or unsubstituted $C_1$-$C_{20}$ straight, branched or cyclic alkyl, alkenyl or oxoalkyl group, or a substituted or unsubstituted $C_6$-$C_{18}$ aryl, aralkyl or aryloxoalkyl group; and two or more of $R^1$, $R^2$ and $R^3$ may be bonded to each other to form a ring with a sulfur atom in the formula,

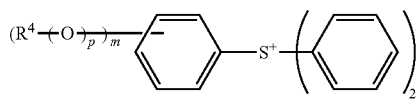
(b)

where $R^4$—$(O)_p$— are independent of each other; $R^4$ represents a substituted or unsubstituted $C_1$-$C_{20}$ straight, branched or cyclic alkyl or alkenyl group, or a substituted or unsubstituted $C_6$-$C_{14}$ aryl group; m represents an integer of 1 to 5; p represents 0 or 1; and $R^4$ may contain a carbonyl group, a hydroxyl group, an ester bond, a lactone ring, an amino group, an amide group or an ether bond as a substituent group,

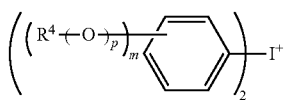
(c)

where $R^4$—$(O)_p$— are independent of each other; $R^4$ represents a substituted or unsubstituted $C_1$-$C_{20}$ straight, branched or cyclic alkyl or alkenyl group, or a substituted or unsubstituted $C_6$-$C_{14}$ aryl group; m represents an integer of 1 to 5; p represents 0 or 1; and $R^4$ may contain a carbonyl group, a hydroxyl group, an ester bond, a lactone ring, an amino group, an amide group or an ether bond as a substituent group.

* * * * *